United States Patent
Cameron et al.

(10) Patent No.: US 6,852,863 B2
(45) Date of Patent: Feb. 8, 2005

(54) METABOLITES OF (3-{[4-TERT-BUTYL-BENZYL)-(PYRIDINE-3-SULFONYL)-AMINO]-METHYL}-PHENOXY)-ACETIC ACID

(75) Inventors: Kimberly O. Cameron, East Lyme, CT (US); Kim A. Johnson, East Haven, CT (US); Bruce A. Lefker, Gales Ferry, CT (US); Chandra A. Prakash, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/353,671

(22) Filed: Jan. 29, 2003

(65) Prior Publication Data

US 2003/0216445 A1 Nov. 20, 2003

Related U.S. Application Data

(60) Provisional application No. 60/353,748, filed on Jan. 31, 2002.

(51) Int. Cl.[7] .................... A61K 31/54; C07D 213/52
(52) U.S. Cl. ........................... 546/313; 514/357
(58) Field of Search ................... 546/313; 514/357

(56) References Cited

U.S. PATENT DOCUMENTS 6,498,172 B1    12/2002    Cameron et al. ............ 514/347
2003/0078261 A1   4/2003   Cameron et al.

FOREIGN PATENT DOCUMENTS

WO         9919300     *   4/1999

OTHER PUBLICATIONS

K. Johnson, et al., Poster, "Metabolism, Excretion and Pharmacokinetics of an EP–2 Receptor Selective PGE2 Agonist, CP–533,536 in male and female rats.", International Society for the Study of Xenobiotics, ISSX, Orlando, FL, Oct. 27–31, 2002.

* cited by examiner

*Primary Examiner*—Rita Desai
(74) *Attorney, Agent, or Firm*—Peter C. Richardson; Gregg C. Benson; Lyman H. Smith

(57) ABSTRACT

The present invention relates to metabolites of (3-{[4-tert-butyl-benzyl)-(pyridine-3-sulfonyl)-amino]-methyl}-phenoxy)-acetic acid.

8 Claims, 14 Drawing Sheets

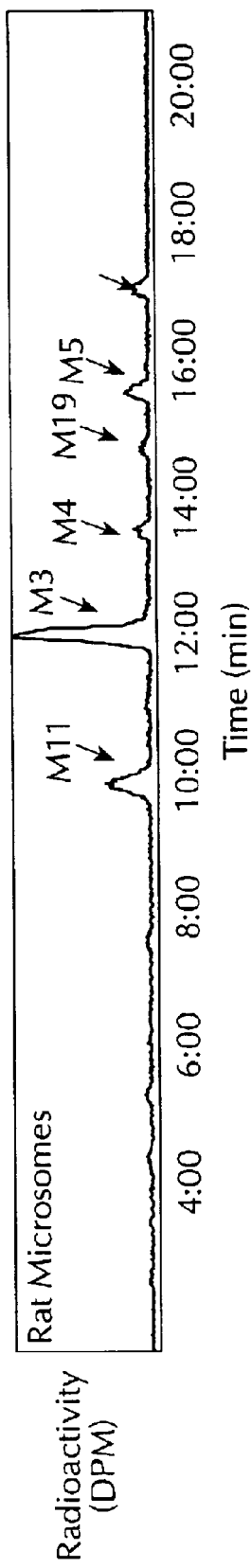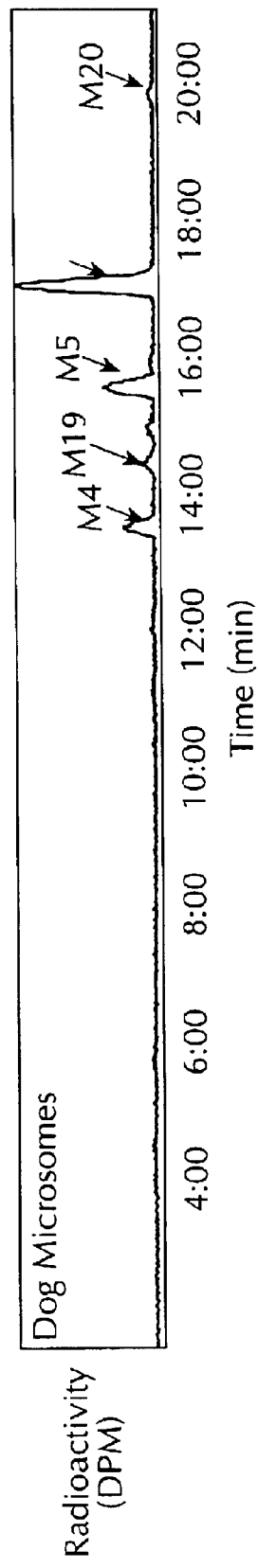

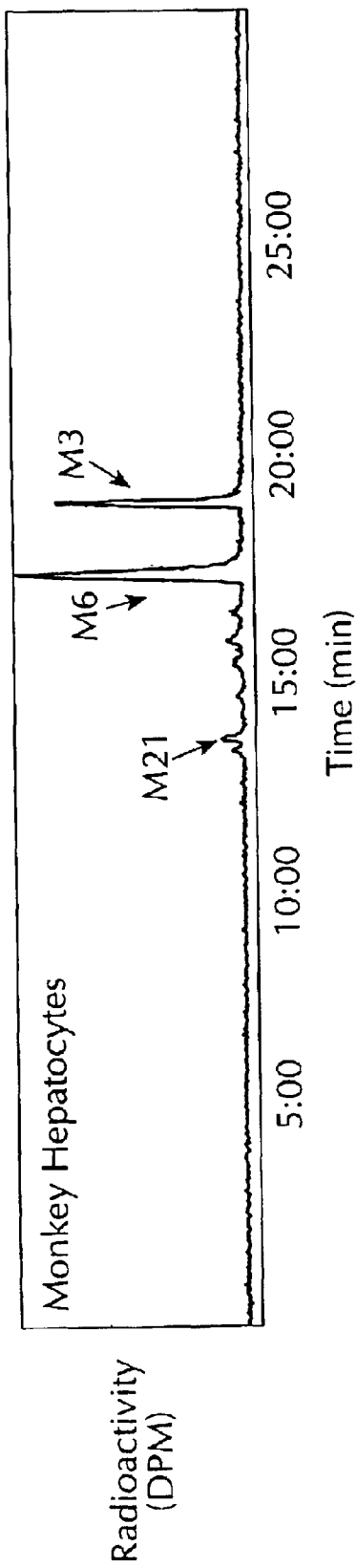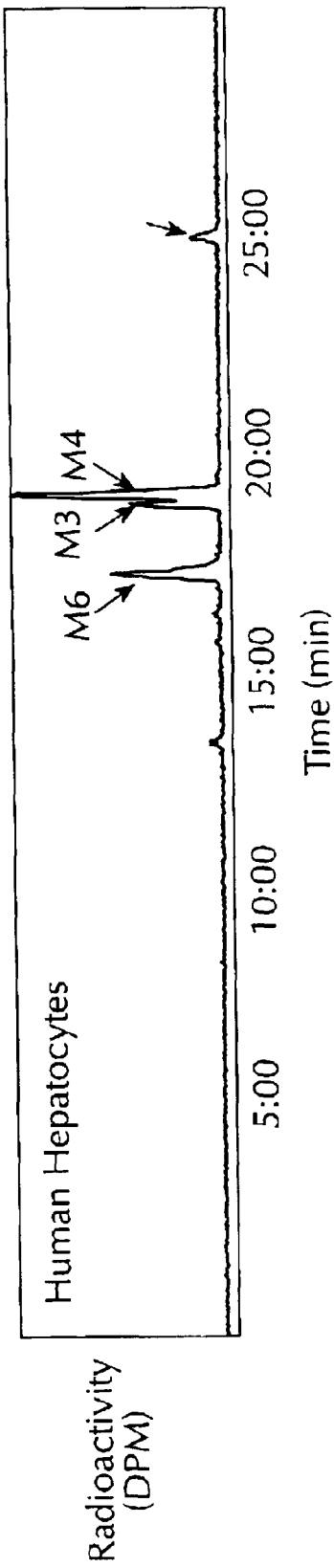

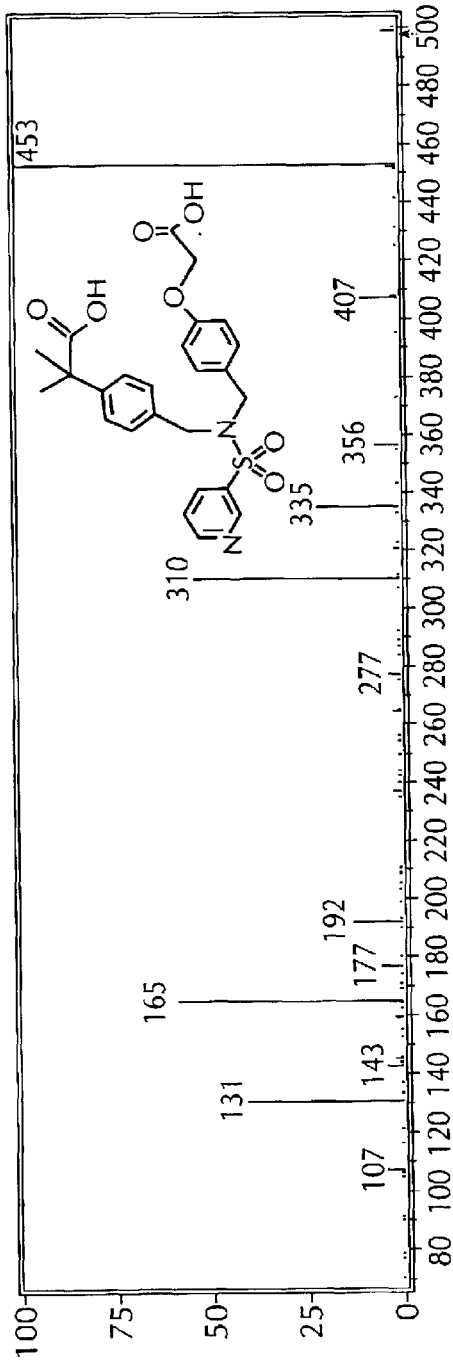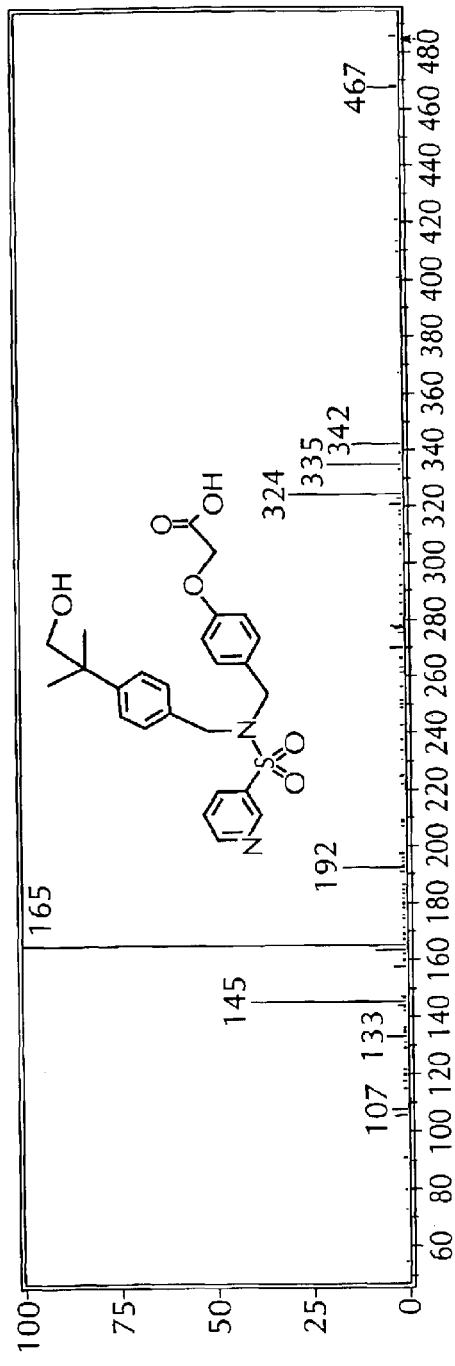

METABOLITES OF (3-{[4-TERT-BUTYL-BENZYL)-(PYRIDINE-3-SULFONYL)-AMINO]-METHYL}-PHENOXY)-ACETIC ACID

CROSS REFERENCE TO RELATED APPLICATION

This application claims priority from U.S. provisional application No. 60/353,748, filed Jan. 31, 2002.

FIELD OF THE INVENTION

The present invention relates to metabolites of (3-{[4-tert-butyl-benzyl)-(pyridine-3-sulfonyl)-amino]-methyl}-phenoxy)-acetic acid. The present invention also relates to methods of treating osteoporosis and aiding in healing bone fractures using a metabolite of (3-{[4-tert-butyl-benzyl)-(pyridine-3-sulfonyl)-amino]-methyl}-phenoxy)-acetic acid. In addition, the present invention relates to methods of determining if a patient has been administered (3-{[4-tert-butyl-benzyl)-(pyridine-3-sulfonyl)-amino]-methyl}-phenoxy)-acetic acid.

BACKGROUND OF THE INVENTION

The compound (3-{[4-tert-butyl-benzyl)-(pyridine-3-sulfonyl)-amino]-methyl}-phenoxy)-acetic acid is a selective $EP_2$ agonist that can be used to treat osteoporosis, aid in healing bone fractures, and treat other conditions presenting with bone loss. The compound (3-{[4-tert-butyl-benzyl)-(pyridine-3-sulfonyl)-amino]-methyl}-phenoxy)-acetic acid is disclosed in WO 99/19300 (PCT/IB98/01540). This compound can also be used to treat osteotomy, childhood idiopathic bone loss, bone loss associated with periodontitis, glucocorticoid-induced osteoporosis, hyperthyroidism-induced osteoporosis, immobilization-induced osteoporosis, heparin-induced osteoporosis immunosuppressive-induced osteoporosis, and for augmenting and maintaining bone mass, bone healing following facial reconstruction, bone healing following maxillary reconstruction, bone healing following mandibular reconstruction, induction of vertebral synostosis, long bone extension enhancement, healing rate of bone graft enhancement and prosthetic ingrowth enhancement.

The present invention provides metabolites of (3-{[4-tert-butyl-benzyl)-(pyridine-3-sulfonyl)-amino]-methyl}-phenoxy)-acetic acid or pharmaceutically acceptable salts or prodrugs of the metabolites, or salts of the prodrugs. The metabolites can be used to treat the same conditions as (3-{[4-tert-butyl-benzyl)-(pyridine-3-sulfonyl)-amino]-methyl}-phenoxy)-acetic acid or can be used to determine if the compound (3-{[4-tert-butyl-benzyl)-(pyridine-3-sulfonyl)-amino]-methyl}-phenoxy)-acetic acid has been administered to a patient.

SUMMARY OF THE INVENTION

The present invention provides the compounds 2-(4-{[(3-carboxymethoxy-benzyl)-(pyridine-3-sulfonyl)-amino]-methyl}-phenyl)-2-methyl-propionic acid;
(3-{[[4-(2-hydroxy-1,1-dimethyl-ethyl)-benzyl]-(pyridine-3-sulfonyl)-amino]-methyl}-phenoxy)-acetic acid;
(3-{[(4-tert-butyl-benzyl)-(pyridine-N-oxide-3-sulfonyl)-amino]-methyl}-phenoxy)-acetic acid;
(5-{[(4-tert-butyl-benzyl)-(pyridine-3-sulfonyl)-amino]-methyl}-hydroxy-phenoxy)-acetic acid;
2-{4-[pyridine-N-oxide-3-sulfonylamino)-methyl]-phenyl}-2-methyl-propionic acid;
(3-{[[4-(2-hydroxy-1,1-dimethyl-ethyl)-benzyl]-(pyridine-3-sulfonyl)-amino]-methyl}-phenoxy)-acetic acid glucuronide;
the sulfate conjugate of pyridine-N-oxide-3-sulfonic acid 4-(2-hydroxy-1,1-dimethyl-ethyl)-benzylamide;
the sulfate conjugate of (3-{[[4-(2-hydroxy-1,1-dimethyl-ethyl)-benzyl]-(pyridine-3-sulfonyl)-amino]-methyl}-phenoxy)-acetic acid;
the sulfate conjugate of pyridine-3-sulfonic acid 4-(2-hydroxy-1,1-dimethyl-ethyl)-benzylamide;
2-methyl-2-{4-[(pyridine-3-sulfonylamino)-methyl]-phenyl}-propionic acid;
(3-{[[4-(1,2-dihydroxy-1-methyl-ethyl)-benzyl]-(pyridine-3-sulfonyl)-amino]-methyl}-phenoxy)-acetic acid;
(3-{[[4-(1-hydroxy-1-methyl-ethyl)-benzyl]-(pyridine-3-sulfonyl)-amino]-methyl}-phenoxy)-acetic acid;
(3-{[[4-(1,1-dimethyl-2-oxo-ethyl)-benzyl]-(pyridine-3-sulfonyl)-amino]-methyl}-phenoxy)-acetic acid; and
(3-{[(4-isopropenyl-benzyl)-(pyridine-3-sulfonyl)-amino]-methyl}-phenoxy)-acetic acid; or the pharmaceutically acceptable salts thereof.

Also provided are methods of determining if a patient has been administered (3-{[4-tert-butyl-benzyl)-(pyridine-3-sulfonyl)-amino]-methyl}-phenoxy)-acetic acid, the methods comprising the step of determining if a plasma, urine, bile or fecal sample obtained from the patient shows the presence of one or more of a compound selected from the group consisting of 2-(4-{[(3-carboxymethoxy-benzyl)-(pyridine-3-sulfonyl)-amino]-methyl}-phenyl)-2-methyl-propionic acid;
(3-{[[4-(2-hydroxy-1,1-dimethyl-ethyl)-benzyl]-(pyridine-3-sulfonyl)-amino]-methyl}-phenoxy)-acetic acid;
2-{4-[pyridine-N-oxide-3-sulfonylamino)-methyl]-phenyl}-2-methyl-propionic acid;
(3-{[[4-(2-hydroxy-1,1-dimethyl-ethyl)-benzyl]-(pyridine-3-sulfonyl)-amino]-methyl}-phenoxy)-acetic acid glucuronide;
the sulfate conjugate of pyridine-N-oxide-3-sulfonic acid 4-(2-hydroxy-1,1-dimethyl-ethyl)-benzylamide;
the sulfate conjugate of (3-{[[4-(2-hydroxy-1,1-dimethyl-ethyl)-benzyl]-(pyridine-3-sulfonyl)-amino]-methyl}-phenoxy)-acetic acid;
the sulfate conjugate of pyridine-3-sulfonic acid 4-(2-hydroxy-1,1-dimethyl-ethyl)-benzylamide;
2-methyl-2-{4-[(pyridine-3-sulfonylamino)-methyl]-phenyl}-propionic acid;
(3-{[(4-tert-butyl-benzyl)-(pyridine-N-oxide-3-sulfonyl)-amino]-methyl}-phenoxy)-acetic acid;
(5-{[(4-tert-butyl-benzyl)-(pyridine-3-sulfonyl)-amino]-methyl}-hydroxy-phenoxy)-acetic acid;
(3-{[[4-(1,2-dihydroxy-1-methyl-ethyl)-benzyl]-(pyridine-3-sulfonyl)-amino]-methyl}-phenoxy)-acetic acid;
(3-{[[4-(1-hydroxy-1-methyl-ethyl)-benzyl]-(pyridine-3-sulfonyl)-amino]-methyl}-phenoxy)-acetic acid;
(3-{[[4-(1,1-dimethyl-2-oxo-ethyl)-benzyl]-(pyridine-3-sulfonyl)-amino]-methyl}-phenoxy)-acetic acid; and
(3-{[(4-isopropenyl-benzyl)-(pyridine-3-sulfonyl)-amino]-methyl}-phenoxy)-acetic acid.

Also provided are methods of treating osteoporosis or aiding in healing a bone fracture, the methods comprising administering to a patient in need thereof a therapeutically effective amount of a compound selected from:
2-(4-{[(3-carboxymethoxy-benzyl)-(pyridine-3-sulfonyl)-amino]-methyl}-phenyl)-2-methyl-propionic acid;
(3-{[[4-(2-hydroxy-1,1-dimethyl-ethyl)-benzyl]-(pyridine-3-sulfonyl)-amino]-methyl}-phenoxy)-acetic acid;
(3-{[(4-tert-butyl-benzyl)-(pyridine-N-oxide-3-sulfonyl)-amino]-methyl}-phenoxy)-acetic acid;

(5-{[(4-tert-butyl-benzyl)-(pyridine-3-sulfonyl)-amino]-methyl}-hydroxy-phenoxy)-acetic acid;
(3-{[[4-(1,2-dihydroxy-1-methyl-ethyl)-benzyl]-(pyridine-3-sulfonyl)-amino]-methyl}-phenoxy)-acetic acid;
(3-{[[4-(1-hydroxy-1-methyl-ethyl)-benzyl]-(pyridine-3-sulfonyl)-amino]-methyl}-phenoxy)-acetic acid;
(3-{[[4-(1,1-dimethyl-2-oxo-ethyl)-benzyl]-(pyridine-3-sulfonyl)-amino]-methyl}-phenoxy)-acetic acid; or
(3-{[(4-isopropenyl-benzyl)-(pyridine-3-sulfonyl)-amino]-methyl}-phenoxy)-acetic acid; or a pharmaceutically acceptable salt thereof.

Also provided are pharmaceutical compositions comprising one or more compound selected from 2-(4-{[(3-carboxymethoxy-benzyl)-(pyridine-3-sulfonyl)-amino]-methyl}-phenyl)-2-methyl-propionic acid;
(3-{[[4-(2-hydroxy-1,1-dimethyl-ethyl)-benzyl]-(pyridine-3-sulfonyl)-amino]-methyl}-phenoxy)-acetic acid;
2-{4-[pyridine-N-oxide-3-sulfonylamino)-methyl]-phenyl}-2-methyl-propionic acid;
(3-{[[4-(2-hydroxy-1,1-dimethyl-ethyl)-benzyl]-(pyridine-3-sulfonyl)-amino]-methyl}-phenoxy)-acetic acid glucuronide;
the sulfate conjugate of pyridine-N-oxide-3-sulfonic acid 4-(2-hydroxy-1,1-dimethyl-ethyl)-benzylamide;
the sulfate conjugate of (3-{[[4-(2-hydroxy-1,1-dimethyl-ethyl)-benzyl]-(pyridine-3-sulfonyl)-amino]-methyl}-phenoxy)-acetic acid;
the sulfate conjugate of pyridine-3-sulfonic acid 4-(2-hydroxy-1,1-dimethyl-ethyl)-benzylamide;
2-methyl-2-{4-[(pyridine-3-sulfonylamino)-methyl]-phenyl}-propionic acid;
(3-{[(4-tert-butyl-benzyl)-(pyridine-N-oxide-3-sulfonyl)-amino]-methyl}-phenoxy)-acetic acid;
(5-{[(4-tert-butyl-benzyl)-(pyridine-3-sulfonyl)-amino]-methyl}-hydroxy-phenoxy)-acetic acid;
(3-{[[4-(1,2-dihydroxy-1-methyl-ethyl)-benzyl]-(pyridine-3-sulfonyl)-amino]-methyl}-phenoxy)-acetic acid;
(3-{[[4-(1-hydroxy-1-methyl-ethyl)-benzyl]-(pyridine-3-sulfonyl)-amino]-methyl}-phenoxy)-acetic acid;
(3-{[[4-(1,1-dimethyl-2-oxo-ethyl)-benzyl]-(pyridine-3-sulfonyl)-amino]-methyl}-phenoxy)-acetic acid; or
(3-{[(4-isopropenyl-benzyl)-(pyridine-3-sulfonyl)-amino]-methyl}-phenoxy)-acetic acid; or a pharmaceutically acceptable salt thereof.

BRIEF DESCRIPTION OF THE FIGURES

FIG. 7. CID product ion spectrum of metabolite M3 (m/z 499).

FIG. 8. CID product ion spectrum of metabolite M4 (m/z 485).

DETAILED DESCRIPTION OF THE INVENTION

Figure 1C:
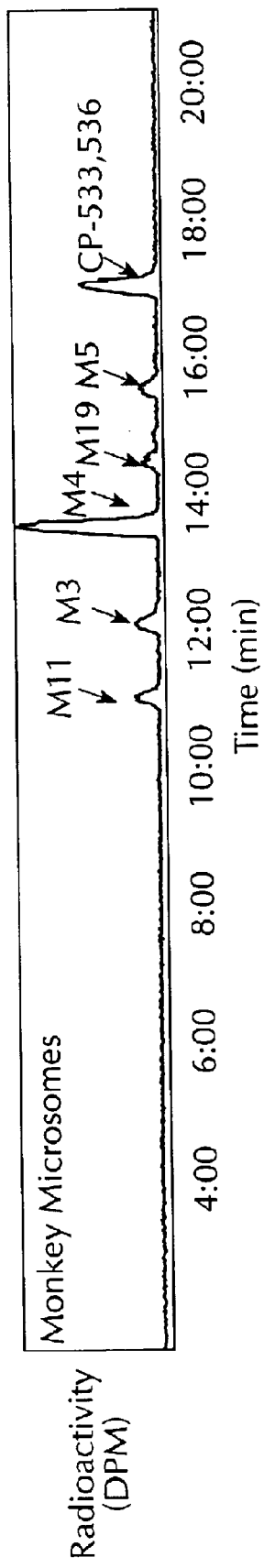
FIG. 1. Representative HPLC radiochromatograms of metabolites of (3-{[4-tert-butyl-benzyl)-(pyridine-3-sulfonyl)-amino]-methyl}-phenoxy)-acetic acid in rat, dog, monkey and human liver microsomes.

The compounds 2-(4-{[(3-carboxymethoxy-benzyl)-(pyridine-3-sulfonyl)-amino]-methyl}-phenyl)-2-methyl-propionic acid; (3-{[[4-(2-hydroxy-1,1-dimethyl-ethyl)-benzyl]-(pyridine-3-sulfonyl)-amino]-methyl}-phenoxy)-acetic acid; 2-{4-[pyridine-N-oxide-3-sulfonylamino)-methyl]-phenyl}-2-methyl-propionic acid; (3-{[[4-(2-hydroxy-1,1-dimethyl-ethyl)-benzyl]-(pyridine-3-sulfonyl)-amino]-methyl}-phenoxy)-acetic acid glucuronide; the sulfate conjugate of pyridine-N-oxide-3-sulfonic acid 4-(2-hydroxy-1,1-dimethyl-ethyl)-benzylamide; the sulfate conjugate of (3-{[[4-(2-hydroxy-1,1-dimethyl-ethyl)-benzyl]—(pyridine-3-sulfonyl)-amino]-methyl}-phenoxy)-acetic acid; the sulfate conjugate of pyridine-3-sulfonic acid 4-(2-hydroxy-1,1-dimethyl-ethyl)-benzylamide; 2-methyl-2-{4-[(pyridine-3-sulfonylamino)-methyl]-phenyl}-propionic acid; (3-{[(4-tert-butyl-benzyl)-(pyridine-N-oxide-3-sulfonyl)-amino]-methyl}-phenoxy)-acetic acid; (5-{[(4-tert-butyl-benzyl)-(pyridine-3-sulfonyl)-amino]-methyl}-hydroxy-phenoxy)-acetic acid; (3-{[[4-(1,2-dihydroxy-1-methyl-ethyl)-benzyl]-(pyridine-3-sulfonyl)-amino]-methyl}-phenoxy)-acetic acid; (3-{[[4-(1-hydroxy-1-methyl-ethyl)-benzyl]-(pyridine-3-sulfonyl)-amino]-methyl}-phenoxy)-acetic acid; (3-{[[4-(1,1-dimethyl-2-oxo-ethyl)-benzyl]-(pyridine-3-sulfonyl)-amino]-methyl}-phenoxy)-acetic acid; and (3-{[(4-isopropenyl-benzyl)-(pyridine-3-sulfonyl)-amino]-methyl}-phenoxy)-acetic acid are metabolites of (3-{[4-tert-butyl-benzyl)-(pyridine-3-sulfonyl)-amino]-methyl}-phenoxy)-acetic acid.

These metabolites or the pharmaceutically acceptable salts or prodrugs thereof, or salts of the prodrugs, can be used to treat the same diseases and conditions as other EP$_2$ agonists, and specifically (3-{[4-tert-butyl-benzyl)-(pyridine-3-sulfonyl)-amino]-methyl}-phenoxy)-acetic acid. Examples of diseases and conditions that can be treated with an EP$_2$ agonist are disclosed in International Patent application publication number WO 99/19300 and include osteotomy, childhood idiopathic bone loss, bone loss associated with periodontitis, glucocorticoid-induced osteoporosis, hyperthyroidism-induced osteoporosis, immobilization-induced osteoporosis, heparin-induced osteoporosis, immunosuppressive-induced osteoporosis, and for augmenting and maintaining bone mass, bone healing following facial reconstruction, bone healing following maxillary reconstruction, bone healing following mandibular reconstruction, induction of vertebral synostosis, long bone extension enhancement, healing rate of bone graft enhancement and prosthetic ingrowth enhancement. Preferred treatments include the treatment of osteoporosis and to aid in healing bone fractures Those skilled in the art will recognize that bone anti-resorptive agents, for example progestins, polyphosphonates, bisphosphonate(s), estrogen agonists/antagonists [also known as SERMs (selective estrogen receptor modulators)], estrogen, estrogen/progestin combinations, Premarin® (conjugated estrogens), estrone, estriol or 17α- or 17β-ethynyl estradiol may be used in combination with the compounds of this invention.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, ethynodiol diacetate, etonogestrel, flurogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol. Preferred progestins are medroxyprogestrone, norethindrone and norethynodrel.

Exemplary bone resorption inhibiting polyphosphonates include polyphosphonates of the type disclosed in U.S. Pat. No. 3,683,080. Preferred polyphosphonates are geminal diphosphonates (also referred to as bisphosphonates). Tiludronate disodium is an especially preferred polyphosphonate. Ibandronic acid is an especially preferred polyphosphonate. Alendronate is an especially preferred polyphosphonate. Zoledronic acid is an especially preferred polyphosphonate. Other preferred polyphosphonates are 6-amino-1-hydroxy-hexylidene-bisphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid,N,N-dimethylamino methane diphosphonic acid, N(2-hydroxyethyl) amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In another embodiment, the compounds of this invention may be combined with an estrogen agonist/antagonist. A preferred estrogen agonist/antagonist is droloxifene: (phenol, 3-(1-(4-(2-(dimethylamino)ethoxy)phenyl)-2-phenyl-1-butenyl)-, (E)-) and related compounds which are disclosed in U.S. Pat. No. 5,047,431.

Another preferred estrogen agonist/antagonist is 3-(4-(1, 2-diphenyl-but-1-enyl)-phenyl)-acrylic acid, which is disclosed in Willson et al., Endocrinology, 1997, 138, 3901–3911.

Another preferred estrogen agonist/antagonist is tamoxifen: (ethanamine,2-(4-(1,2-diphenyl-1-butenyl)phenoxy)-N,N-dimethyl, (Z)-2-, 2-hydroxy-1,2,3-propanetricarboxylate(1:1)) and related compounds, which are disclosed in U.S. Pat. No. 4,536,516.

Another related compound is 4-hydroxy tamoxifen, which is disclosed in U.S. Pat. No. 4,623,660.

A preferred estrogen agonist/antagonist is raloxifene: (methanone, (6-hydroxy-2-(4-hydroxyphenyl)benzo[b]thien-3-yl)(4-(2-(1-piperidinyl)ethoxy)phenyl)-hydrochloride) which is disclosed in U.S. Pat. No. 4,418,068.

Another preferred estrogen agonist/antagonist is toremifene: (ethanamine, 2-(4-(4-chloro-1,2-diphenyl-1-butenyl)phenoxy)-N,N-dimethyl-, (Z)-, 2-hydroxy-1,2,3-propanetricarboxylate (1:1) which is disclosed in U.S. Pat. No. 4,996,225.

Another preferred estrogen agonist/antagonist is centchroman: 1-(2-((4-(methoxy-2,2, dimethyl-3-phenyl-chroman-4-yl)-phenoxy)-ethyl))-pyrrolidine, which is disclosed in U.S. Pat. No. 3,822,287. Also preferred is levormeloxifene.

Another preferred estrogen agonist/antagonist is idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,155.

Another preferred estrogen agonist/antagonist is 2-(4-methoxy-phenyl)-3-[4-(2-piperidin-1-yl-ethoxy)-phenoxy]-benzo[b]thiophen-6-ol which is disclosed in U.S. Pat. No. 5,488,058.

Another preferred estrogen agonist/antagonist is 6-(4-hydroxy-phenyl)-5-(4-(2-piperidin-1-yl-ethoxy)-benzyl)-naphthalen-2-ol, which is disclosed in U.S. Pat. No. 5,484,795.

Another preferred estrogen agonist/antagonist is (4-(2-(2-aza-bicyclo[2.2.1]hept-2-yl)-ethoxy)-phenyl)-(6-hydroxy-2-(4-hydroxy-phenyl)-benzo[b]thiophen-3-yl)-methanone which is disclosed, along with methods of preparation, in PCT publication no. WO 95/10513.

Other preferred estrogen agonist/antagonists include compounds as described in commonly assigned U.S. Pat. No. 5,552,412. Especially preferred compounds described therein are:

cis-6-(4-fluoro-phenyl)-5-(4-(2-piperidin-1-yl-ethoxy)-phenyl)-5,6,7,8-tetrahydro-naphthalene-2-ol;

(−)-cis-6-phenyl-5-(4-(2-pyrrolidin-1-yl-ethoxy)-phenyl)-5,6,7,8-tetrahydro-naphthalene-2-ol;

cis-6-phenyl-5-(4-(2-pyrrolidin-1-yl-ethoxy)-phenyl)-5, 6,7,8-tetrahydro-naphthalene-2-ol;

cis-1-(6'-pyrrolodinoethoxy-3'-pyridyl)-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-(4-(2-piperidin-1-yl-ethoxy)-phenyl)-5,6,7,8-tetrahydro-naphthalene-2-ol; and 1-(4'-pyrrolidinolethoxyphenyl)-2-phenyl-6-hydroxy-1,2, 3,4-tetrahydroisoquinoline.

A particularly preferred compound is (−)-cis-6-phenyl-5-(4-(2-pyrrolidin-1-yl-ethoxy)-phenyl)-5,6,7,8-tetrahydro-naphthalene-2-ol, D-tartrate, which is disclosed in U.S. Pat. No. 5,948,809.

Other estrogen agonist/antagonists are described in U.S. Pat. No. 4,133,814. U.S. Pat. No. 4,133,814 discloses derivatives of 2-phenyl-3-aroyl-benzothiophene and 2-phenyl-3-aroylbenzothiophene-1-oxide.

Other preferred estrogen agonists/antagonists include TSE-424 (U.S. Pat. No. 5,998,402), arozoxifene (U.S. Pat. No. 5,723,474), EM-652, EM-800, GW 5638, and GW 7604, or an optical or geometric isomer thereof; pharmaceutically acceptable salt, N-oxide, ester, quaternary ammonium salt, or prodrug thereof.

Other preferred estrogen agonists/antagonists include compounds of formula V or VI:

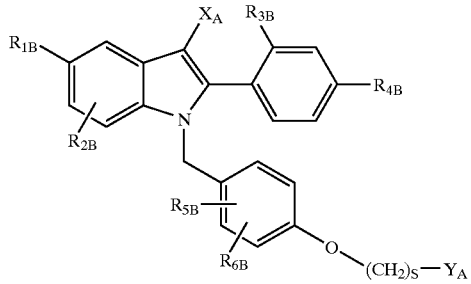

(V)

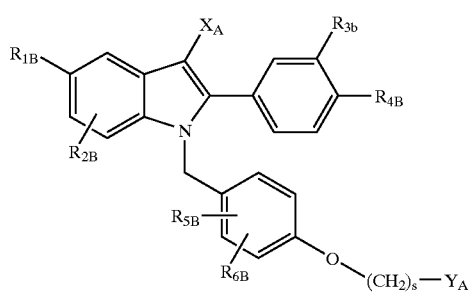

(VI)

wherein:

$R_{1B}$ is selected from H, OH, —O—C(O)—$C_1$–$C_{12}$ alkyl (straight chain or branched), —O—$C_1$–$C_{12}$ alkyl (straight chain or branched or cyclic), or halogens or $C_1$–$C_4$ halogenated ethers;

$R_{2B}$, $R_{3B}$, $R_{4B}$, $R_{5B}$, and $R_{6B}$ are independently selected from H, OH, —O—C(O)—$C_1$–$C_{12}$ (straight chain or branched), —O—$C_1$–$C_{12}$ (straight chain or branched or cyclic), halogens, or $C_1$–$C_4$ halogenated ethers, cyano, $C_1$–$C_6$ alkyl (straight chain or branched), or trifluoromethyl;

$X_A$ is selected from H, $C_1$–$C_6$ alkyl, cyano, nitro, trifluoromethyl, and halogen;

s is 2 or 3;

$Y_A$ is the moiety:

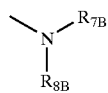

wherein:

a) $R_{7B}$ and $R_{8B}$ are independently selected from the group of H, $C_1$–$C_6$ alkyl, or phenyl optionally substituted by CN, $C_1$–$C_6$ alkyl (straight chain or branched), $C_1$–$C_6$ alkoxy (straight chain or branched), halogen, —OH, —$CF_3$, or —$OCF_3$; or b) $R_{7B}$ and $R_{8B}$ are concatenated to form a five-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$)alkyl; or c) $R_{7B}$ and $R_{8B}$ are concatenated to form a six-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2RIB$, —$NHCOR_{1B}$, —$NO_2$, or phenyl optionally substituted with 1–3 ($C_1$–$C_4$)alkyl; or d) $R_{7B}$ and $R_{8B}$ are concatenated to form a seven-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$)alkyl; or e) $R_{7B}$ and $R_{8B}$ are concatenated to form an eight-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$alkyl)$_2$, —$NHSO_2R_{1B}$, —$NHCOR_{1B}$, —$NO_2$, or phenyl optionally substituted with 1–3 ($C_1$–$C_4$)alkyl; or f) $R_{7B}$ and $R_{8B}$ are concatenated to form a saturated bicyclic heterocycle containing from 6–12 carbon atoms either bridged or fused and containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$) alkyl; or an optical or geometric isomer thereof; or a pharmaceutically acceptable salt, N-oxide, ester, quaternary ammonium salt or prodrug thereof.

An additional preferred estrogen agonist/antagonist is the compound of formula Va:

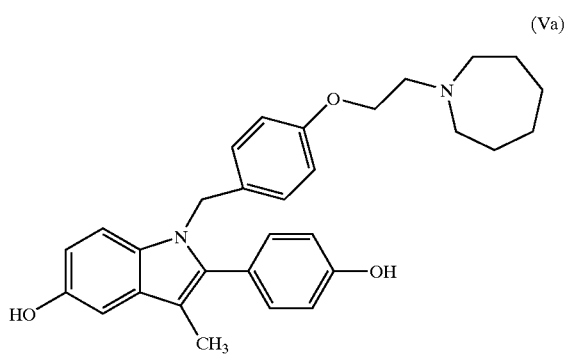

(Va)

or an optical or geometric isomer thereof; or a pharmaceutically acceptable salt, N-oxide, ester, quaternary ammonium salt or prodrug thereof.

Other preferred estrogen agonists/antagonists include the compounds of formula III (EM-652) or formula IV (EM-800) below:

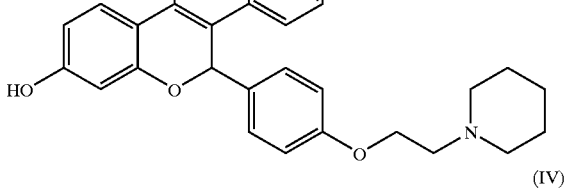

(III)

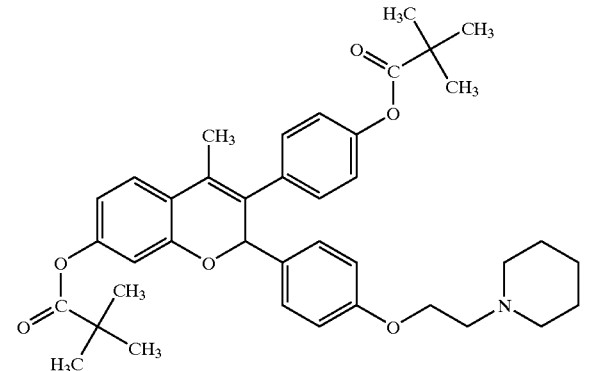

(IV)

or an optical or geometric isomer thereof; or a pharmaceutically acceptable salt, N-oxide, ester, quaternary ammonium salt or prodrug thereof.

Those skilled in the art will recognize that other bone anabolic agents, also referred to as bone mass augmenting agents, may be used in conjunction with the compounds of this invention. A bone mass augmenting agent is a compound that augments bone mass to a level which is above the bone fracture threshold as detailed in the World Health Organization Study World Health Organization, "Assessment of Fracture Risk and its Application to Screening for Postmenopausal Osteoporosis (1994). Report of a WHO Study Group. World Health Organization Technical Series 843."

It is also possible to use a compound of the present invention in combination with other $EP_2$ agonists. Preferred $EP_2$ agonists include 7-[(4-butyl-benzyl)-methanesulfonyl-amino]-heptanoic acid, monosodium salt or other compounds disclosed in U.S. Pat. No. 6,288,120.

Those skilled in the art will recognize that IGF-1, sodium fluoride, parathyroid hormone (PTH), active fragments of parathyroid hormone, growth hormone or growth hormone secretagogues may also be used in combination with the present compounds.

The compounds of the present invention can also be used in combination with prostaglandins. A variety of prostaglandins are described and referenced below. However, other prostaglandins will be known to those skilled in the art. Exemplary prostaglandins are disclosed in U.S. Pat. Nos. 4,171,331 and 3,927,197. Norrdin et al., *The Role of Prostaglandins in Bone In Vivo,* Prostaglandins Leukotriene Essential Fatty Acids 41, 139–150, 1990 is a review of bone anabolic prostaglandins.

Other compounds that can be used in combination with the compounds of the present invention include those compounds disclosed in U.S. Pat. No. 3,932,389, which discloses 2-descarboxy-2-(tetrazol-5-yl)-11-desoxy-15-substituted-omega-pentanorprostaglandins useful for bone formation activity; U.S. Pat. No. 4,018,892, which discloses 16-aryl-13,14-dihydro-$PGE_2$ p-biphenyl esters useful for bone formation activity; U.S. Pat. No. 4,219,483, which discloses 2,3,6-substituted-4-pyrones useful for bone formation activity; U.S. Pat. No. 4,132,847, which discloses 2,3,6-substituted-4-pyrones useful for bone formation activity; U.S. Pat. No. 4,000,309, which discloses 16-aryl-13,14-dihydro-$PGE_2$ p-biphenyl esters useful for bone formation activity; U.S. Pat. No. 3,982,016, which discloses 16-aryl-13,14-dihydro-$PGE_2$ p-biphenyl esters useful for bone formation activity; U.S. Pat. No. 4,621,100, which discloses substituted cyclopentanes useful for bone formation activity; and U.S. Pat. No. 5,216,183, which discloses cyclopentanones useful for bone formation activity.

Sodium fluoride may also be used in combination with the compounds of the present invention. The term "sodium fluoride" refers to sodium fluoride in all its forms (e.g., slow release sodium fluoride, sustained release sodium fluoride). Sustained release sodium fluoride is disclosed in U.S. Pat. No. 4,904,478, the disclosure of which is incorporated herein by reference. The activity of sodium fluoride is readily determined by those skilled in the art of biological protocols (e.g., see Eriksen E. F. et al., *Bone Histomorphometry,* Raven Press, New York, 1994, pages 1–74; Grier S. J. et al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296).

Bone morphogenetic proteins may also be used in combination with the compounds of the present invention (e.g., see Ono, et al., Promotion of the Osteogenetic Activity of Recombinant Human Bone Morphogenetic Protein by Prostaglandin E1, *Bone,* 1996, 19(6), 581–588).

Any parathyroid hormone (PTH) may also be used in combination with the compounds of the present invention. The term "parathyroid hormone" refers to parathyroid hormone, fragments or metabolites thereof and structural analogs thereof which can stimulate bone formation and increase bone mass. Also included are parathyroid hormone related peptides and active fragments and analogs of parathyroid related peptides (see PCT publication no. WO 94/01460). Such bone anabolic functional activity is readily determined by those skilled in the art of standard assays (e.g., see Eriksen E. F. et al., Bone Histomorphometry, Raven Press, New York, 1994, pages 1–74; Grier S. J. et al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below. However, other parathyroid hormones will be known to those skilled in the art. Exemplary parathyroid hormones are disclosed in the following references.

"Human Parathyroid Peptide Treatment of Vertebral Osteoporosis", Osteoporosis Int., 3, (Supp 1):199–203.

"PTH 1–34 Treatment of Osteoporosis with Added Hormone Replacement Therapy: Biochemical, Kinetic and Histological Responses" Osteoporosis Int. 1:162–170.

Any growth hormone or growth hormone secretagogue may also be used in combination with the compounds of the present invention. The term growth hormone secretagogue refers to a compound which stimulates the release of growth hormone or mimics the action of growth hormone (e.g., increases bone formation leading to increased bone mass). Such actions are readily determined by those skilled in the art of standard assays well known to those of skill in the art. A variety of these compounds are disclosed in the following published PCT patent applications: WO 95/14666; WO 95/13069; WO 94/19367; WO 94/13696; and WO 95/34311. However, other growth hormones or growth hormone secretagogues will be known to those skilled in the art.

In particular a preferred growth hormone secretagogue is N-[1(R)-[1,2-dihydro-1-methanesulfonylspiro[3H-indole-3, 4'-piperidin]-1'-yl)carbonyl]-2-(phenylmethyloxy)ethyl]-2-amino-2-methylpropanamide: MK-677.

Other preferred growth hormone secretagogues include:

2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide (U.S. Pat. No. 6,107,306) or its L-tartaric acid salt;

2-amino-N-{1(R)-benzyloxymethyl-2-[1,3-dioxo-8a-(S)-pyridin-2-ylmethyl-2-(2,2,2,-trifluoro-ethyl)-hexahydro-imidazo-[1,5a]pyrazin-7-yl]-2-oxo-ethyl}-2-methyl-propionamide (U.S. Pat. No. 6,251,902) or its hydrochloride salt;

2-amino-N-(1-(R)-benzyloxymethyl-2-(3a-(R)-(4-fluoro-benzyl)-2-methyl-3-oxo-2,3,3a,4,6,7-hexahydro-pyrazolo[4,3-c]pyridin-5-yl)-2-oxo-ethyl)isobutyramide;

2-amino-N-(2-(3a-(R)-benzyl-3-oxo-2,3,3a,4,6,7-hexahydro-pyrazolo[4,3-c]pyridin-5-yl)-1-(R) benzyloxymethyl-2-oxo-ethyl)isobutyramide; and 2-amino-N-(1-(2,4-difluoro-benzyloxymethyl)-2-oxo-2-(3-oxo-3a-pyridin-2-ylmethyl-2-(2,2,2-trifluoro-ethyl)-2,3,3a,4,6,7-hexahydro-pyrazolo[4,3-c]pyridin-5-yl)-ethyl)-2-methyl-propionamide (U.S. Pat. No. 6,110,932) or its L-tartaric acid salt.

The compounds of the present invention are generally administered in the form of a pharmaceutical composition comprising at least one compound of this invention together with a pharmaceutically acceptable vehicle or diluent. For oral administration, a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

Capsules are prepared by mixing the compound with a suitable diluent and filling the proper amount of the mixture in capsules. The usual diluents include inert powdered substances such as starch of many different kinds; powdered cellulose, especially crystalline and microcrystalline cellulose; sugars such as fructose, mannitol and sucrose; grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant may be necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances that facilitate the disintegration of a tablet to release a compound when the tablet becomes wet. They include starches, clays, celluloses, algins and gums, corn and potato starches, methylcellulose, agar, bentonite, wood cellulose, powdered natural sponge, cation-exchange resins, alginic acid, guar gum, citrus pulp and carboxymethylcellulose, for example, may be used as well as sodium lauryl sulfate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

When it is desired to administer a compound as a suppository, the typical bases may be used. Cocoa butter is a traditional suppository base, which may be modified by addition of waxes to raise its melting point slightly. Watermiscible suppository bases comprising, particularly, polyethylene glycols of various molecular weights are in wide use.

The effect of the compounds may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film which resists dissolution for a predictable period of time. Even the parenteral preparations may be made long-acting, by dissolving or suspending the compound in oily or emulsified vehicles which allow it to disperse only slowly in the serum.

Pharmaceutical compositions of the invention may contain 0.1%–95% of the compound(s) of this invention, preferably 1%–70%. In any event, the composition or formulation to be administered will contain a quantity of a compound of this invention in an amount effective to treat the disease/condition.

The following paragraphs describe exemplary formulations and dosages useful for non-human animals. The administration of a compound of the present invention can be effected orally or non-orally, for example by injection. An amount of a compound of the present invention is administered such that an effective dose is received, generally a daily dose which, when administered orally to an animal is usually between 0.01 and 100 mg/kg of body weight, preferably between 0.1 and 50 mg/kg of body weight. It is noted that more than one dose per day may be required and that a veterinarian can determine an effective dose taking into account the particular circumstances.

Conveniently, the compound can be carried in the drinking water so that a therapeutic dosage of the compound is ingested with the daily water supply. The compound can be directly metered into drinking water, preferably in the form of a liquid, water-soluble concentrate (such as an aqueous solution of a water soluble salt). Conveniently, the compound can also be added directly to the feed, as such, or in the form of an animal feed supplement, also referred to as a premix or concentrate. A premix or concentrate of the compound in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the compound in the finished feed with which the premix is blended. It is important that the compound be thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of active compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

For parenteral administration in animals, the compounds of the present invention may be prepared in the form of a paste or a pellet and administered as an implant, usually under the skin of the head or ear of the animal.

Paste formulations can be prepared by dispersing a compound of the present invention in pharmaceutically acceptable oil such as peanut oil, sesame oil, corn oil or the like.

Pellets containing an effective amount of a compound of the present invention can be prepared by admixing a compound of the present invention with a diluent such as carbowax, carnauba wax, and the like. A lubricant, such as magnesium or calcium stearate, can be added to improve the pelleting process.

It is, of course, recognized that more than one pellet may be administered to an animal to achieve the desired dose level. Moreover, it has been found that implants may also be made periodically during the animal treatment period in order to maintain the proper active agent level in the animal's body.

"Treatment" as used herein includes preventative (e.g., prophylactic) and palliative treatment and "treating" as used herein refers to the act of providing preventative and/or palliative treatment.

The term "therapeutically effective amount" means an amount of a compound of the present invention or a combination of a compound of the present invention with additional compounds that ameliorates one or more symptom or prevents or delays the onset of one of more symptom of a disease or condition.

"Patient" as used herein means mammals, particularly humans.

"Glucuronic acid" is the substituent that is transferred to a metabolite or transferred to a parent compound to form a metabolite from the phase II conjugation reaction of glucuronidation. Glucuronic acid reacts with an acid or alcohol or phenol moiety on the metabolite or parent compound to form the "glucuronide." The glucoronide substituent is abbreviated in the formulae herein as "Glu" or "Glucuronide".

"Sulfuric acid" is the substituent that is transferred to a metabolite or transferred to a parent compound to form a metabolite from the conjugation reaction of sulfation. Sulfuric acid reacts with an alcohol or phenol moiety on the metabolite or parent compound to form the "sulfate" or the "sulfate conjugate."

Administration a combination of a compound of the present invention and an additional compound or additional compounds means that these compounds can be administered together as a composition or as part of the same unitary dosage form or in separate dosage forms, administered at the same time or at different times.

The chemist of ordinary skill will recognize that certain compounds of this invention will contain one or more atoms that may be in a particular stereochemical, tautomeric, or geometric configuration, giving rise to stereoisomers, tautomers, regio and configurational isomers. All such isomers and mixtures thereof are included in this invention. Hydrates and solvates of the compounds of this invention are also included.

The present invention also includes isotopically-labeled compounds, which are identical to the compounds of the present invention, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out the procedures exemplified below or those known in the art.

The compounds of the present invention may be used as analytical standards for in vitro or in vivo metabolism studies or as intermediates for the chemical synthesis or biosynthesis of new chemical entities. The metabolites may be isolated as solids or in solution. The compounds of the present invention can also be used to identify patients who have been administered (3-{[4-tert-butyl-benzyl)-(pyridine-3-sulfonyl)-amino]-methyl}-phenoxy)-acetic acid or a pharmaceutically acceptable salt or prodrug thereof, or salt of a prodrug. To identify a patient that has been administered (3-{[4-tert-butyl-benzyl)-(pyridine-3-sulfonyl)-amino]-methyl}-phenoxy)-acetic acid or a pharmaceutically acceptable salt or prodrug thereof or salt of a prodrug, a serum, urine, fecal or bile sample is taken from the patient and the sample is analyzed for the presence of one or more compound of the present invention. One method of analyzing for the compounds of the present invention is by using chromatography and mass spectroscopy. Other analysis methods are well known to those skilled in the art. The presence of one or more compound of the present invention in a serum, urine, fecal or bile sample indicates that the patient has been administered (3-{[4-tert-butyl-benzyl)-(pyridine-3-sulfonyl)-amino]-methyl}-phenoxy)-acetic acid or a pharmaceutically acceptable salt or prodrug thereof, or salt of a prodrug.

In the methods of treatment of the present invention, a compound of the present invention can be administered to a patient directly, such as in a tablet, or the compound can be administered by being produced in the patient's body through metabolism. Moreover, the administration route and dosage of the compound that gives rise to a compound of the present invention by metabolism can be varied, as desired, to obtain desired in vivo concentration and rate of production of a compound of the present invention.

The pharmaceutically acceptable acid addition salts of the compounds of this invention may be formed of the compound itself, or of any of its esters, and include the pharmaceutically acceptable salts which are often used in pharmaceutical chemistry. For example, salts may be formed with inorganic or organic acids such as hydrochloric acid, hydrobromic acid, hydroiodic acid, sulfonic acids including such agents as naphthalenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, most preferable with hydrochloric acid, citric acid, benzoic acid, maleic acid, acetic acid and propionic acid.

When used as a medicine, the dose of a compound of this invention to be administered to a human or other patient is rather widely variable and subject to the judgment of the attending physician or veterinarian. It should be noted that it may be necessary to adjust the dose of a compound when it is administered in the form of a salt, such as a laureate, the salt forming moiety of which has an appreciable molecular weight. The general range of effective administration rates of the compounds is from about 0.001 mg/day to about 200 mg/day. A preferred range is from about 0.01 mg/day to 100 mg/day. Of course, it is often practical to administer the daily dose of compound in portions, at various hours of the day. However, in any given case, the amount of compound administered will depend on such factors as the solubility of the active component, the formulation used and the route of administration.

A prodrug is a compound that is transformed in vivo to yield a compound of the present invention. The transformation may occur by various mechanisms, such as through hydrolysis in blood. A good discussion of the use of prodrugs is provided by T. Higuchi and W. Stella, "Pro-drugs as Novel Delivery Systems," Vol. 14 of the *A.C.S. Symposium Series*, and in *Bioreversible Carriers in Drug Design*, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as ($C_1$–$C_8$) alkyl, ($C_2$–$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-($C_1$–$C_2$)alkylamino($C_2$–$C_3$)alkyl (such as α-dimethylaminoethyl), carbamoyl-($C_1$–$C_2$)alkyl, N,N-di ($C_1$–$C_2$)alkylcarbamoyl-($C_1$–$C_2$)alkyl and piperidino-, pyrrolidino- or morpholino($C_2$–$C_3$)alkyl.

Similarly, if a compound of the present invention comprises an alcohol functional group, a prodrug can be formed by the replacement of the hydrogen atom of the alcohol group with a group such as ($C_1$–$C_6$)alkanoyloxymethyl, 1-(($C_1$–$C_6$)alkanoyloxy)ethyl, 1-methyl-1-(($C_1$–$C_6$) alkanoyloxy)ethyl, ($C_1$–$C_6$)alkoxycarbonyloxymethyl, N-($C_1$–$C_6$)alkoxycarbonylaminomethyl, succinoyl, ($C_1$–$C_6$) alkanoyl, α-amino($C_1$–$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O ($C_1$–$C_6$)alkyl)$_2$ or glycosyl (the radical resulting from the removal of a hydroxyl group of the hemiacetal form of a carbohydrate).

If a compound of the present invention comprises an amine functional group, a prodrug can be formed by the replacement of a hydrogen atom in the amine group with a group such as $R^X$-carbonyl, $R^XO$-carbonyl, $NR^XR^{X'}$-carbonyl where $R^X$ and $R^{X'}$ are each independently $((C_1-C_{10})$alkyl, $(C_3-C_7)$cycloalkyl, benzyl, or $R^X$-carbonyl is a natural α-aminoacyl or natural α-aminoacyl-natural α-aminoacyl, —C(OH)C(O)OY$^X$ wherein (Y$^X$ is H, $(C_1-C_6)$ alkyl or benzyl), —C(OY$^{X0}$)Y$^{X1}$ wherein Y$^{X0}$ is $(C_1-C_4)$ alkyl and Y$^{X1}$ is $((C_1-C_6)$alkyl, carboxy$(C_1-C_6)$alkyl, amino $(C_1-C_4)$alkyl or mono-N- or di-N,N-$(C_1-C_6)$ alkylaminoalkyl, —C(Y$^{X2}$)Y$^{X3}$ wherein Y$^{X2}$ is H or methyl and Y$^{X3}$ is mono-N- or di-N,N-$(C_1-C_6)$alkylamino, morpholino, piperidin-1-yl or pyrrolidin-1-yl.

Advantageously, the present invention also provides kits for use by a consumer for treating disease. The kits comprise a) a pharmaceutical composition comprising a compound of the present invention and a pharmaceutically acceptable carrier, vehicle or diluent; and b) instructions describing a method of using the pharmaceutical composition for treating the specific disease.

A "kit" as used in the instant application includes a container for containing the separate unit dosage forms such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It maybe desirable to provide a written memory aid, where the written memory aid is of the type containing information and/or instructions for the physician, pharmacist or subject, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday," . . . etc. . . . . "Second Week, Monday, Tuesday, . . . " etc. Other variations of memory aids will be readily apparent. A "daily dose" can be a single tablet or capsule or several tablets or capsules to be taken on a given day.

Another specific embodiment of a kit is a dispenser designed to dispense the daily doses one at a time. Preferably, the dispenser is equipped with a memory-aid, so as to further facilitate compliance with the regimen. An example of such a memory-aid is a mechanical counter, which indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds the patient when the next dose is to be taken.

In still another embodiment of the kits, the pharmaceutical composition may also comprise an additional compound that can be used in combination with a compound of the present invention, or the kit may comprise two pharmaceutical compositions: one containing a compound of the present invention and another containing an additional compound that can be used in combination with a compound of the present invention.

The documents cited herein, including any patents and patent applications, are hereby incorporated by reference.

The examples presented herein are intended to illustrate particular embodiments of the invention, and are not intended to limit the specification or the claims in any manner.

EXAMPLES

Radiolabelled Mass Balance and Metabolic Profiles of $^{14}$C-(3-{[4-tert-butyl-benzyl)-(pyridine-3-sulfonyl)-amino]-methyl}-phenoxy)-acetic acid in Sprague Dawley Rats Objective To determine the radiolabelled mass balance and metabolic profiles of (3-{[4-tert-butyl-benzyl)-(pyridine-3-sulfonyl)-amino]-methyl}-phenoxy)-acetic acid in urine, feces, bile and plasma of Sprague-Dawley rats after I.V. administration of a single 15 mg/kg dose of $^{14}$C-(3-{[4-tert-butyl-benzyl)-(pyridine-3-sulfonyl)-amino]-methyl}-phenoxy)-acetic acid.

Materials and Methods

Radiolabelled Compound

The $^{14}$C-(3-{[4-tert-butyl-benzyl)-(pyridine-3-sulfonyl)-amino]-methyl}-phenoxy)-acetic acid (specific activity 4.36 mCi/mmol) showed a radio purity of >99%.

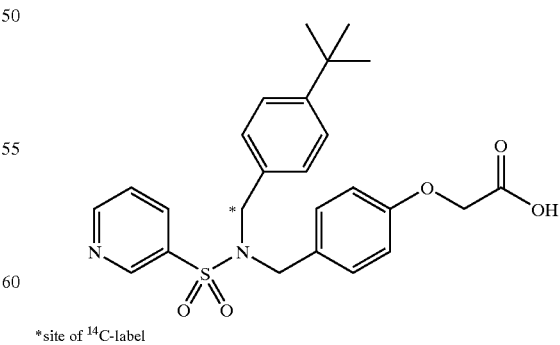

*site of $^{14}$C-label $^{14}$C-(3-{[4-tert-butyl-benzyl)-(pyridine-3-sulfonyl)-amino]-methyl}-phenoxy)-acetic acid can be made in accordance with the scheme set forth below.

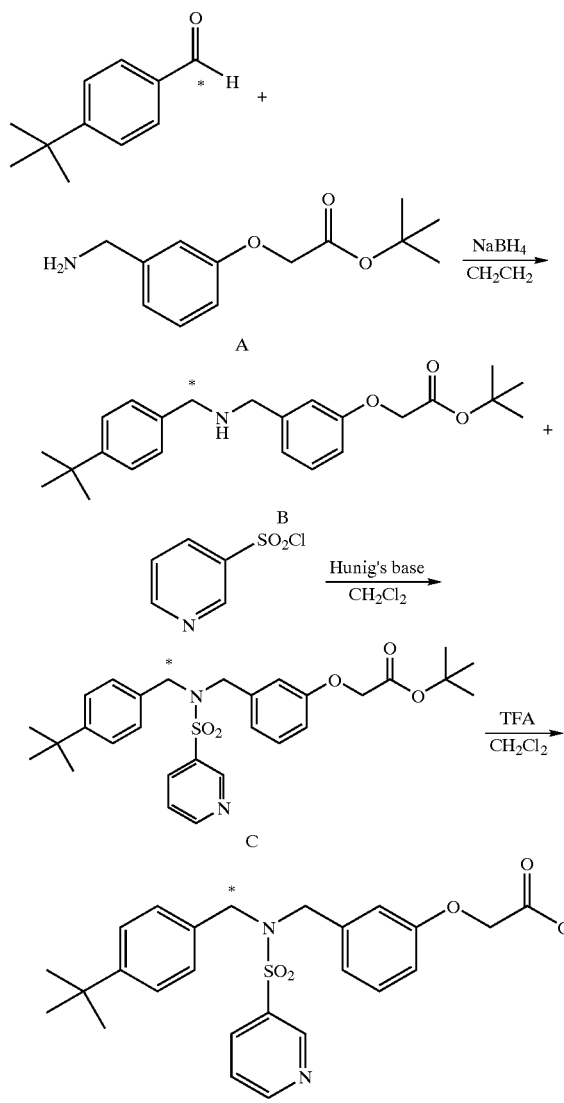

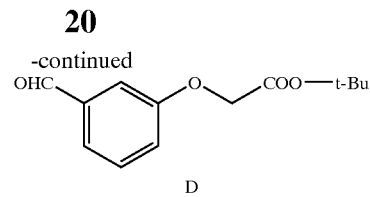

1 eq (equivalent) aldehyde, 1 eq carbonate, 1.25 eq t-butylbromoacetate in acetone
reflux 20–24 hours
quench with water
extract into ethyl acetate, displace with 2-propanol (IPO) for next step Step 2

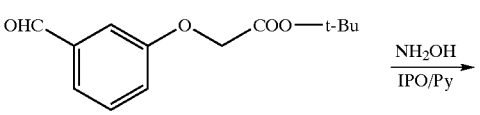

1 eq compound D, 2 eq hydroxylamine.HCl, 2 eq pyridine (Py), in IPO
heat at reflux 3–4 hours
work-up with ethyl acetate & aqueous HCl
replace with 2B ethanol (denatured with toluene) for next step Step 3

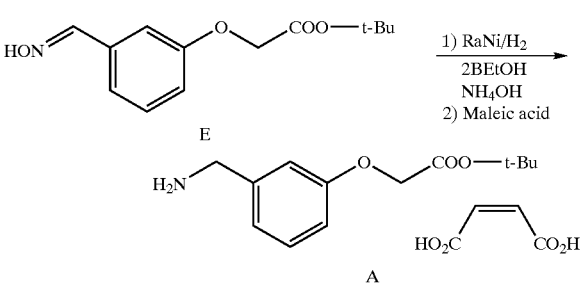

The radiolabeled aldehyde (ChemSyn Laboratories, Lenexa, Kans.) and amine A were stirred overnight at room temperature in methylene chloride (with imine formation monitored by aliquot quenched in to NaBH$_4$ and HPLC analysis) and treated with NaBH$_4$ to give compound B, which was then treated with excess pyridine-3-sulfonyl chloride and Hunig's base (diisopropyl ethylamine) in methylene chloride to form compound C, which is reacted with tifluoroacetic acid in methylene chloride to form $^{14}$C-(3-{[4-tert-butyl-benzyl)-(pyridine-3-sulfonyl)-amino]-methyl}-phenoxy)-acetic acid.

Compound A can be made as follows:

Step 1

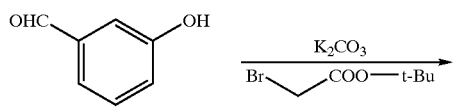

Compound E in 2B ethanol, 30% RaNi (Rainey Nickel) charge, 28% ammonium
extract isoproyl ether; concentrate to oil
dissolve oil in IPO and add maleic acid in IPO
add isopropyl ether to crash out the salt Animal Models A group of three male and three female jugular-vein cannulated Sprague-Dawley rats (230–240 g) was housed individually in stainless steel metabolic cages designed to collect urine and feces and administered intravenously a single, 15 mg/kg, dose of $^{14}$C-(3-{[4-tert-butyl-benzyl)-(pyridine-3-sulfonyl)-amino]-methyl}-phenoxy)-acetic acid.

For pharmacokinetic and plasma identification, two groups of animals were dosed (three males and three females for pharmacokinetic and 2 males and 2 females for plasma identification) intravenously with 15 mg/kg dose of $^{14}$C-(3-{[4-tert-butyl-benzyl)-(pyridine-3-sulfonyl)-amino]-methyl}-phenoxy)-acetic acid.

A fourth group of animals (bile duct and jugular vein cannulated, n=2 per sex) was dosed for the collection of bile and urine to assess routes of excretion and biliary metabolites.

Sample Collection

Urine and feces were collected from group I animals for 7 days at 0–24, 24–48, 48–72, 72–96, 96–120, 120–144 and 144–168 hours post dose. Whole blood was taken at 5 min, 15 min, 1, 2, 4, 6, 8, 24, and 48 hours post dose for pharmacokinetic analysis and 1 and 4 hours post dose for identification of circulating metabolites. Plasma was separated from whole blood by centrifugation. Bile and urine were collected from bile duct cannulated animals at 0–8, 8–24 and 24–48 hours post-dose.

Sample Analysis

Determination of Radioactivity

The radioactivity in urine, bile and plasma was determined by liquid scintillation counting. Aliquots of urine (0.1 g), bile (0.025 g) or plasma (0.025 g) were mixed with 5 ml of Ecolite (+) scintillation cocktail and counted in a Wallac #1409 liquid scintillation counter (Gaithersburg, Md.). Fecal samples at each time point were homogenized with water, and the total weights of the fecal homogenate were recorded. Aliquots (0.1–0.3 g) of the homogenates were oxidized with a Packard oxidizer (Packard Instrument Co., Downer's Grove, Ill.) prior to scintillation counting.

The radioactivity in the dose was established as 100% of the total radioactivity. The radioactivity at each sampling time for urine and feces was defined as the percentage of dose excreted in the respective matrices.

The radioactivity measured in plasma was converted to ng equivalents of (3-{[4-tert-butyl-benzyl)-(pyridine-3-sulfonyl)-amino]-methyl}-phenoxy)-acetic acid based on the specific activity of the dosing vehicle of 19.75 dpm/ng.

Quantitative Assessment of Metabolite Excretion

Metabolite quantification was performed by measuring the areas of individually separated HPLC peaks using the β-RAM (IN/US, Win-flow). The β-RAM provided integrated peak representation printouts in CPM as well as the percentage of the radiolabelled material. The β-RAM was operated using a solid scintillation cell.

Extraction of Metabolites from Biological Samples

Urine samples (about 10 ml) were evaporated under nitrogen overnight. Sample residues were reconstituted in 1 ml of 0.1% formic acid/acetonitrile (50:50). These solutions were vortexed for about 1 min, transferred to 1.5 ml eppendorf tubes and then centrifuged at 14,000 rpm for about 2 min. Aliquots (10–20 µl) of the supernatants were injected onto the HPLC column without further purification.

Fecal homogenates containing the highest levels of excreted radioactivity (0–48 hours) were pooled. From the pooled samples (about 80–135 g), aliquots (about 5 g) were suspended in 15 ml of acetonitrile. Suspensions were sonicated (about 30 min.), vortexed and centrifuged at 3200 rpm for 10 min. Following supernatant transfer to clean 15 ml conical tubes, the residues were further extracted 2 times with 15 ml of acetonitrile as described above. Aliquots (200 µl) from each extraction were counted in a liquid scintillation counter. The recovery of radioactivity extracted ranged from 92–96%. The supernatants were evaporated to dryness under nitrogen in a Turbo Vap LV evaporator (Zymark, Hopkinton, Mass.) and the residues were reconstituted in 2 ml of mobile phase. Aliquots (10–20 µl) of concentrated fecal extracts were injected onto the HPLC column.

Plasma for the identification of circulating metabolites was precipitated using 2 volumes of acetonitrile. Suspensions were sonicated (about 30 min.), vortexed and centrifuged at 3200 rpm for 10 min. Following supernatant transfer to clean 15 ml conical tubes, the residues were further extracted with 2×15 ml of acetonitrile as described above. The supernatants were combined and evaporated to dryness under nitrogen in a Turbo Vap LV evaporator and the residues were reconstituted in 0.5 ml of mobile phase. Aliquots (50–100 µl) of concentrated plasma extracts were injected onto the HPLC column.

Bile was directly injected into the HPLC/MS system for analysis without further purification.

High Performance Liquid Chromatography

The HPLC system consisted of a HP-1100 solvent delivery system, a HP-1100 membrane degasser, a HP-1100 autoinjector (Hewlett Packard) and an IN/US radioactive monitor (β—RAM). Chromatography was performed on a YMC AQ (C-18) column (4.6 mm×150 mm, 3 µm) (Waters, Milford, Mass.). The mobile phase was initially composed of 10 mM ammonium formate pH 5.0 (solvent A) and acetonitrile (solvent B). The solvent delivery step gradient program was as follows:

| Time (min) | % Solvent A | % Solvent B |
|---|---|---|
| 0–3 | 90 | 10 |
| 3–25 | 35 | 65 |
| 25–26 | 10 | 90 |
| 26–29 | 10 | 90 |
| 29–31 | 90 | 10 |
| 31–35 | 90 | 10 |

The system was allowed to equilibrate for 10 minutes prior to the next injection. A flow rate of 1.0 ml/min was maintained throughout the analysis. For the quantification of plasma metabolites, the HPLC effluent was directed into the flow cell of a β-ram radioactivity detector. The β-ram and HPLC was externally controlled using an ARC (Accurate radioisotope counting) system, for low-level radioactivity counting.

Mass Spectrometry

Identification of the metabolites was performed using a Finnigan TSQ 7000 triple quadrupole mass spectrometer equipped with an API-2 electrospray interface (Finnigan, San Jose, Calif.). The HPLC column effluent was split so that approximately 50 µl/min was introduced into the API interface. The remaining effluent was directed to the flow cell of β-RAM. The β-RAM response was recorded as a real time analog signal by the MS data collection system. The collected data from the radioactivity and MS detectors were separated by the dwell volume of flow from the MS to the radioactivity detector (corresponding to a dwell time of about 0.2 min.). The electrospray voltage operated at −4.5 eV as the mass spectrometer collected data in the positive ion mode. Collision induced dissociation (CID) studies were performed with argon gas in Q2 (Q2 is second quadrupole) using collision energy of 30–35 eV and a collision gas thickness of approximately 2.1 mTorr.

Results and Discussion

Identification of Metabolites

Metabolite M8

Metabolite M8 had a retention time of 10:26–11:35 (min:sec) and showed a protonated molecular ion at m/z 351. It was detected in urine (males) and bile. The CID fragmentation pattern of M8 had prominent fragments at m/z 305, 146 and 131. The ion at m/z 305, a 46 amu loss from the molecular ion, suggested the presence of a carboxylic acid moiety. The ions at m/z 131 and 146 may have resulted from the carboxy isopropyl benzyl and carboxy isopropyl benylamine moieties, respectively, with the concomitant loss of the formic acid. Based on its fragmentation pattern and molecular ion, it is suggested that M8 was formed from N-debenzylation of the phenoxy acetic acid moiety, followed by oxidation of the t-butyl moiety to the carboxylic acid and hydroxylation of the pyridine ring. Reaction of this metabolite with titanium trichloride (20% solution in phosphoric acid) caused the retention time of this metabolite to increase by approximately 1 minute, and the resulting M+H$^+$ ion to decrease by 16 amu, suggesting that this metabolite is an N-oxide. Based on this data, M8 was identified as 2-{4-[pyridine-N-oxide-3-sulfonylamino)-methyl]-phenyl}-2-methyl-propionic acid.

a molecule of water and sulfate from the molecule. The ion at m/z 145, two amu lower than that of the parent compound at m/z 147, suggested that the t-butyl benzyl had been hydroxylated and a molecule of water had been lost during the fragmentation. Additionally, reaction of this metabolite with titanium trichloride (20% solution in phosphoric acid) caused the retention time of this metabolite to increase by approximately 2 minutes, and the resulting M+H$^+$ ion to decrease by 16 amu, suggesting that this metabolite is an N-oxide. Based on these data, the structure of M9 was proposed as the sulfate conjugate of pyridine-N-oxide-3-sulfonic acid 4-(2-hydroxy-1,1-dimethyl-ethyl)-benzylamide.

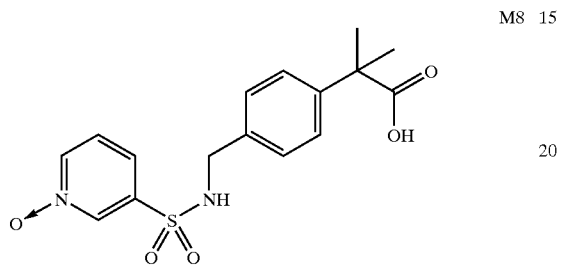

M8

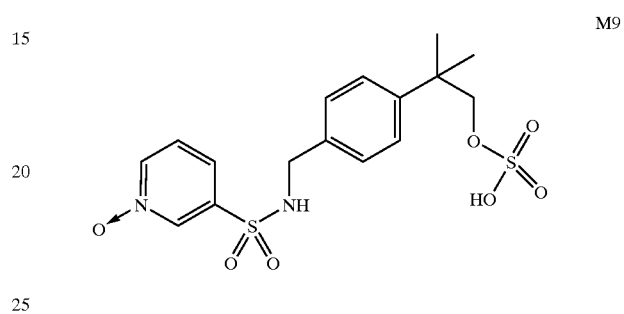

M9

Metabolite M13

Metabolite M13 had a retention time of about 10:47 (min:sec) on HPLC and was detected only in bile (males). It showed a protonated molecular ion at m/z 661, 192 amu higher than the parent compound. Its CID product ion spectrum showed prominent fragment ions at m/z 485, 467, 342, 324, 165, and 145. The ion at m/z 485 was due to the loss of glucuronic acid from the molecular ion. The ion at m/z 467 occurred from the loss of water from the ion at m/z 485. The ions at m/z 342 and 324 resulted from the subsequent losses of a sulfonyl pyridine moiety and water. The ion at m/z 165, similar to that of the parent compound, was due to a protonated methyl phenoxy acetic acid moiety. The ion at m/z 145 indicated a loss of water from the hydroxy t-butyl benzyl moiety. Based on these data, M13 was identified as (3-{[[4-(2-hydroxy-1,1-dimethyl-ethyl)-benzyl]-(pyridine-3-sulfonyl)-amino]-methyl}-phenoxy)-acetic acid glucuronide.

Metabolite M6

Metabolite M6 had a retention time of about 11:23–12:37 (min:sec) on HPLC and was found in feces, bile and plasma. It showed a protonated molecular ion at m/z 565 (96 amu higher than the parent compound), suggesting the addition of an atom of oxygen and a sulfate group. The CID product ion spectrum of M6 showed prominent fragments at m/z 485, 467, 342, 324, 165 and 145. The ions at m/z 485 and 467 were due to subsequent losses of sulfate and water from the protonated molecular ion. The ion at m/z 165 was similar to that of the parent compound indicating that the methyl phenoxy acetic acid moiety was not changed. The ion at m/z 342 (16 amu higher than that observed in the parent compound) indicated that the addition of an atom of oxygen had occurred on the t-butyl benzyl moiety. The ions at m/z 324 and 145 were 2 amu lower than those corresponding in the spectrum of the parent compound, again suggested an addition of oxygen to the t-butyl benzyl moiety, and upon fragmentation a molecule of water was lost. Based on this data, M6 was identified as the sulfate conjugate of (3-{[[4-(2-Hydroxy-1,1-dimethyl-ethyl)-benzyl]-(pyridine-3-sulfonyl)-amino]-methyl}-phenoxy)-acetic acid.

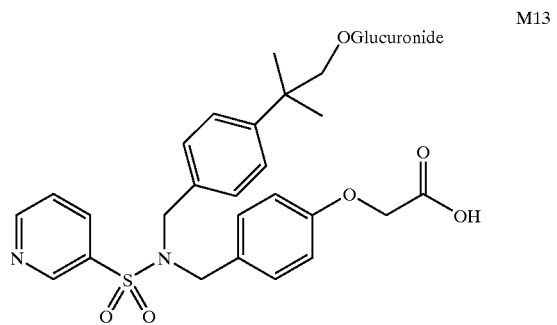

M13

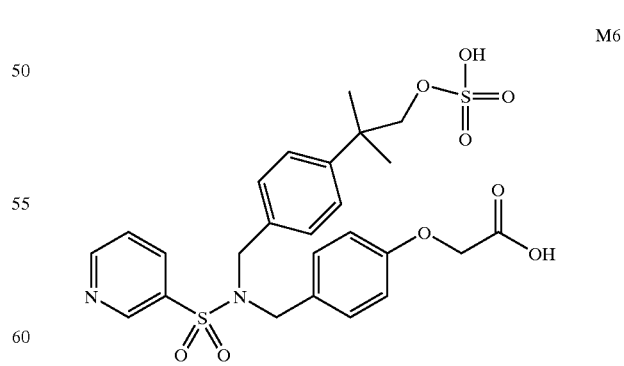

M6

Metabolite M9

Metabolite M9 had a protonated molecular ion at m/z 417 and was detected only in female rat urine. It had a retention time of about 11:35 (min:sec) on HPLC. The protonated molecular ion at m/z 417, 52 amu lower than the parent compound, suggested that the M9 was a cleaved product. The CID product ion spectrum of M9 showed prominent ions at m/z 319, 160 and 145. The ion at m/z 319, 98 amu lower than the protonated molecular ion, suggested a loss of Metabolite M10

Metabolite M10 had a protonated molecular ion at m/z 401 and was found only in feces and female urine. It had a retention time of about 13:26 (min:sec) on HPLC. The molecular ion at m/z 401, 68 daltons lower than the parent compound, suggested that it was a cleaved product. The CID product ion spectrum of M10 showed prominent ions at m/z 303, 160 and 145. The ion at m/z 303, 98 amu lower than the protonated molecular ion, suggested a loss of sulfuric acid from the molecule. The ion at m/z 145, two amu lower than that of the parent compound at m/z 147, suggested that the t-butyl benzyl had been hydroxylated and a molecule of water had been lost during the fragmentation. Based on these data, the structure of M10 was proposed as the sulfate conjugate of pyridine-3-sulfonic acid 4-(2-hydroxy-1,1-dimethyl-ethyl)-benzylamide.

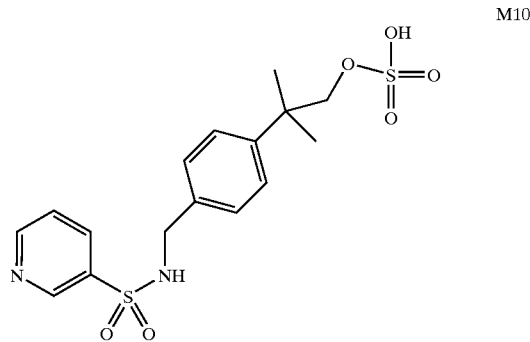

M10

Metabolite M11

Metabolite M11 had a retention time of about 12:04–14:20 (min:sec) and was found in urine and bile and showed a protonated molecular ion at m/z 335. The molecular ion at m/z 335, 134 daltons lower than the parent compound, suggested that it was a cleaved product. The CID fragmentation pattern of M11 had prominent fragments at m/z 289, 146 and 131. The ion at m/z 289, a 46 amu loss from the molecular ion, suggested the presence of a carboxylic acid moiety. The ions at m/z 131 and 146 may have resulted from the carboxy isopropyl benzyl and carboxy isopropyl benzylamine moieties, respectively, with the concomitant loss of the formic acid. Based on these data, the structure of M11 was proposed as 2-methyl-2-{4-[(pyridine-3-sulfonylamino)-methyl]-phenyl}-propionic acid.

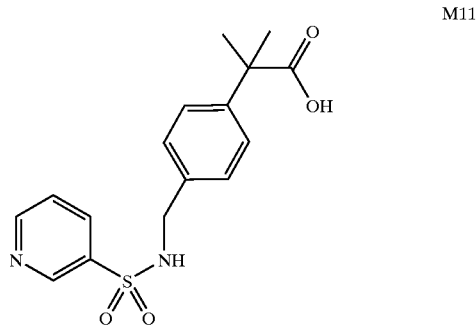

M11

Metabolite M3

Metabolite M3 had a retention time of about 12:33–14:21 (min:sec) on HPLC and was found in bile (male) and feces. It showed a protonated molecular ion at m/z 499 (30 amu higher than the parent compound). The CID product ion spectrum showed prominent fragments at m/z 453, 356, 310, 165 and 131. The ion at m/z 165 was similar to that of the parent compound, suggesting that the methylphenoxy acetic acid moiety was unchanged. The ion at m/z 356 was 30 amu higher than that observed in the parent compound, suggesting the addition of two atoms of oxygen and a loss of two hydrogen atoms. The ions at m/z 310 and 131 were due to a loss of 46 amu from the ions at m/z 356 and 177, respectively, suggesting the presence of a carboxylic acid moiety. Based on these data, metabolite M3 was identified as 2-(4-{[(3-carboxymethoxy-benzyl)-(pyridine-3-sulfonyl)-amino]-methyl}-phenyl)-2-methyl-propionic acid.

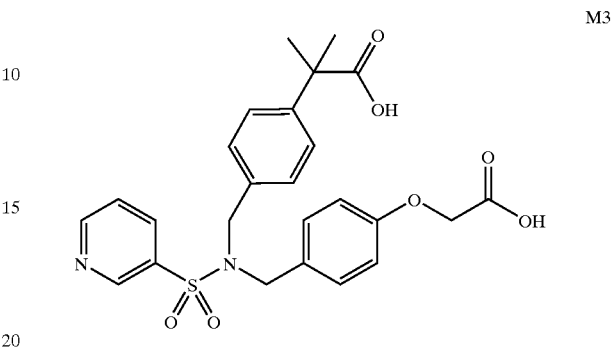

M3

Metabolite M4

Metabolite M4 had a retention time of about 13:20–15:00 (min:sec) on HPLC and was found in feces, bile, plasma and female urine. It showed a protonated molecular ion at m/z 485 (16 amu higher than the parent compound). CID product ion spectrum of m/z 485 showed prominent fragment ions at m/z 467, 342, 324, 165, and 145. The ion at m/z 467 occurred from the loss of water from the molecule. The ion at m/z 342 resulted from the loss of a sulfonyl pyridine moiety and followed by a loss of water to form the ion at m/z 324. The ion at m/z 165, similar to that of the parent compound, was due to a protonated methyl phenoxy acetic acid moiety. The ion at m/z 145 indicated a loss of water from the hydroxy t-butyl benzyl moiety. Based on these data, M4 was identified as (3-{[[4-(2-hydroxy-1,1-dimethyl-ethyl)-benzyl]-(pyridine-3-sulfonyl)-amino]-methyl}-phenoxy)-acetic acid.

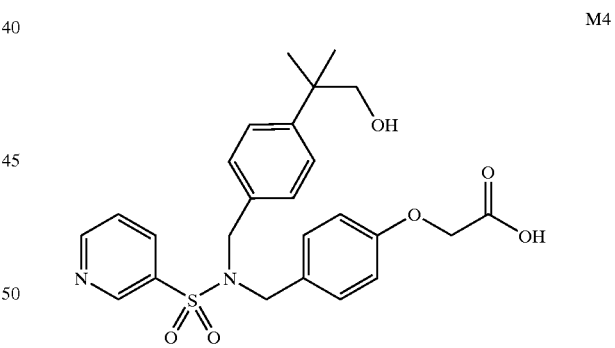

M4

Metabolite M5

Metabolite M5 had a retention time of about 15:23 (min:sec) on HPLC and was found in plasma and bile. It showed a protonated molecular ion at m/z 485 (16 amu higher than the parent compound). CID product ion spectrum of M5 showed prominent fragment ions at m/z 439, 326, 165, and 147. The ion at m/z 439 occurred from the loss of formic acid from the molecule. The ions at m/z 326, 165 and 147 were similar to those of the parent compound suggesting that the methylphenoxy acetic acid and the t-butyl benzyl moieties were unchanged. Based on these data, M5 was identified as (3-{[(4-tert-butyl-benzyl)-(pyridine-N-oxide-3-sulfonyl)-amino]-methyl}-phenoxy)-acetic acid.

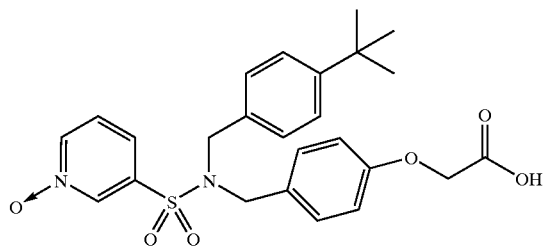

Metabolite M14

Metabolite M14 had a retention time of about 16:90 min on HPLC and was found only in bile. It showed a protonated molecular ion at m/z 645, 176 daltons higher than that of the parent compound, suggesting that it was a glucuronide conjugate. The CID product ion spectrum of m/z 645 showed prominent fragment ions at m/z 469, 423, 413, 326, 165, and 147. The ion at m/z 469 occurred from the loss of a glucuronic acid moiety from the molecule. The ion at m/z 423 occurred from the loss of formic acid from the molecule. The loss of the t-butyl group resulted in the ion at m/z 413. The ion at m/z 326 resulted from the loss of a sulfonyl pyridine moiety. The ion at m/z 165 was due to a protonated methyl phenoxy acetic acid moiety. Based on these data, this metabolite was identified as (3-{[4-tert-butyl-benzyl)-(pyridine-3-sulfonyl)-amino]-methyl}-phenoxy)-acetic acid glucuronide.

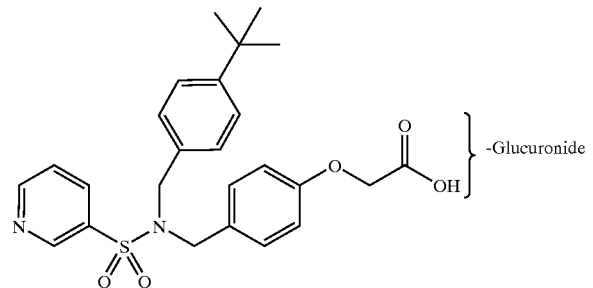

Metabolite M12

Metabolite M12 had a retention time of 15:50–17:50 (min:sec) on HPLC and was found in feces and bile. It showed a protonated molecular ion at m/z 485 (16 amu higher than the parent compound). The CID product ion spectrum of metabolite M12 showed prominent fragments at m/z 485, 342, 305, 181, 162 and 147. The ions at m/z 162 and 147 were similar to those seen in the parent compound, suggesting that the t-butyl benzyl moiety was unchanged. The ions at m/z 181 and 342 were 16 amu higher than those observed in the parent compound (m/z 165 and m/z 326, respectively), indicating the addition of an oxygen atom to the methylphenoxy acetic acid moiety. The ion at m/z 305 was due to loss of the hdroxy phenoxy acetic acid moiety. Based on these data, M12 was identified as (5-{[(4-tert-butyl-benzyl)-(pyridine-3-sulfonyl)-amino]-methyl}-hydroxy-phenoxy)-acetic acid. It is noted that when this chemical name is used in the application, the position of the hydroxyl group on the phenyl ring is not specified and the name is intended to encompass each of the possible positions of the hydroxyl group.

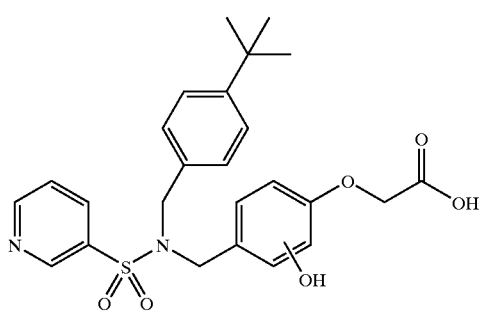

An overview of the metabolism pathways of (3-{[4-tert-butyl-benzyl)-(pyridine-3-sulfonyl)-amino]-methyl}-phenoxy)-acetic acid is given in Scheme 1. The major oxidative pathway was due to the oxidation of the t-butyl moiety to form hydroxy methyl metabolite, M4 (males 19.7%; females 6.5%). M4 was further oxidized to form carboxylic acid metabolite M3 (males 32.8%; females 1.66%) or conjugated with sulfuric acid to form metabolite M6 (males 12.7%; females 36.2%). Other minor metabolites were due to N-oxidation of the pyridine ring (M5) and hydroxylation and N-dealkylation of the methyl-phenoxyacetic acid moiety followed by phase 11 conjugation. In addition to the parent compound, circulating metabolites included M4, M5 and M6.

Scheme 1.
Metabolic pathways of (3-{[4-tert-butyl-benzyl)-(pyridine-3-sulfonyl)-amino]-methyl}-phenoxy)-acetic acid in Sprague-Dawley rats following a single 15 mg/kg intravenous dose of $^{14}$C-(3-{[4-tert-butyl)-(pyridine-3-sulfonyl)-amino]-methyl}-phenoxy)-acetic acid.

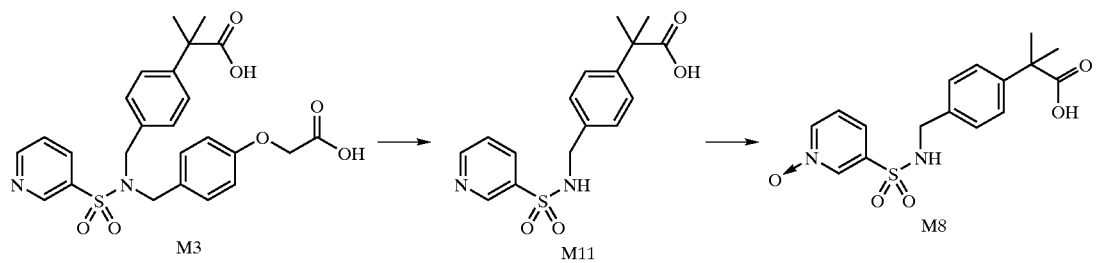

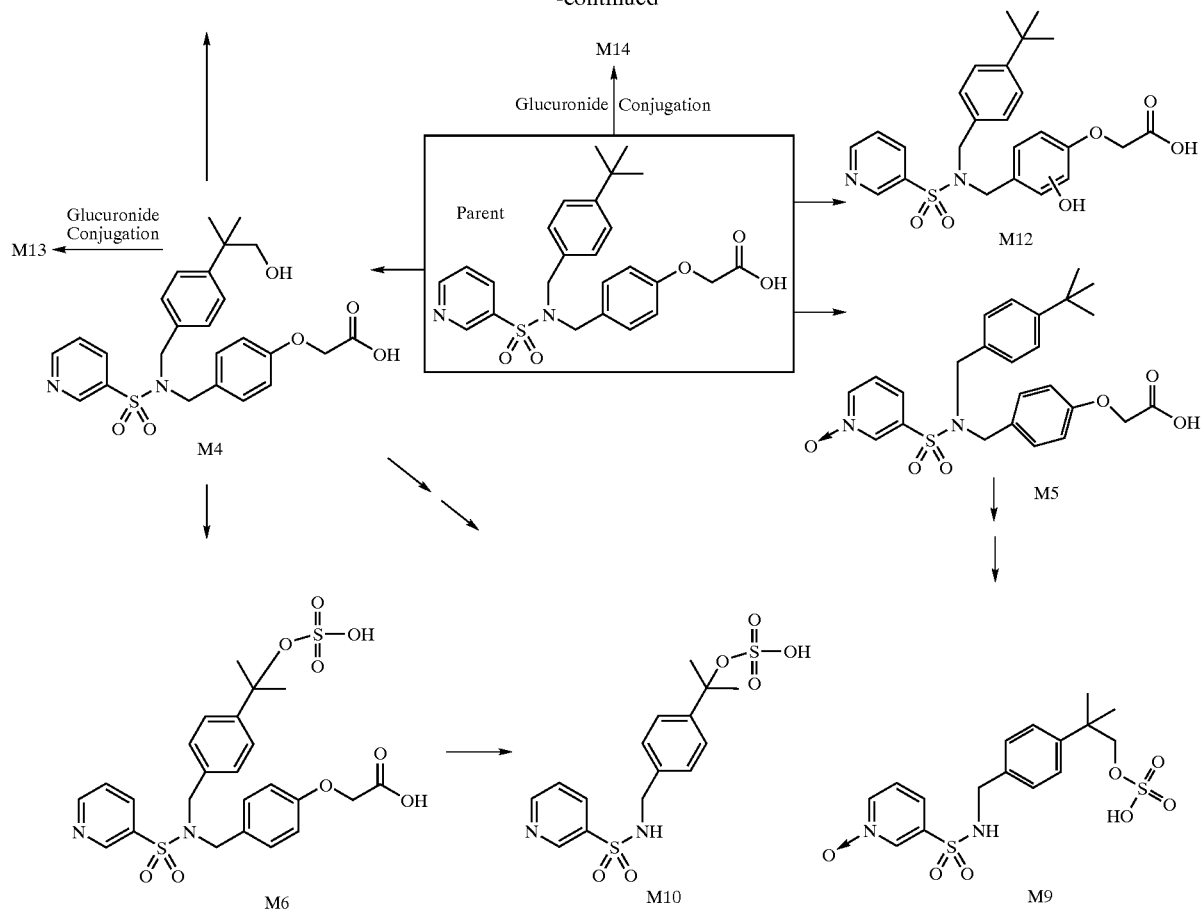

Identification of In-Vitro Metabolites of (3-{[4-tert-butyl-benzyl)-(pyridine-3-sulfonyl)-amino]-methyl}-phenoxy)-acetic acid in Liver Microsomes and Hepatocytes of Rats, Dogs, Monkeys and Humans (3-{[4-tert-butyl-benzyl)-(pyridine-3-sulfonyl)-amino]-methyl}-phenoxy)-acetic acid was extensively metabolized in rat, dog, monkey, and human liver microsomes and hepatocytes. The major metabolic pathways were due to oxidation of the t-butyl moiety to form an alcohol, oxidation of the pyridine moiety, and/or N-dealkylation of the methylphenoxy acetic acid moiety. The alcohol metabolite M4 was further oxidized to corresponding carboxylic acid M3. In hepatocytes, M4 was conjugated with sulfuric acid. In dog hepatocytes, one of the metabolite M12 was due to aromatic oxidation of the methylphenoxy acetic acid moiety.

Objectives

To determine the metabolic pathways of (3-{[4-tert-butyl-benzyl)-(pyridine-3-sulfonyl)-amino]-methyl}-phenoxy)-acetic acid in liver microsomes and hepatocytes from human, rat, dog and monkey.

Materials

Radiolabeled Compound $^{14}$C-(3-{[4-tert-butyl-benzyl)-(pyridine-3-sulfonyl)-amino]-methyl}-phenoxy)-acetic acid (specific activity 4.36 mCi/mmol) showed a radio purity of >99% and was synthesized as described above.

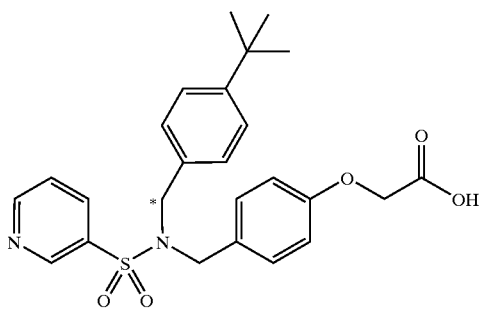

Microsomal Incubations

Human (HL-mix 12), rat, monkey and dog liver microsomes were prepared by differential centrifugation using standard procedures. Prior to use, liver microsomes were thawed on ice and reconstituted using 100 mM potassium phosphate pH 7.4. [$^{14}$C]-(3-{[4-tert-butyl-benzyl)-(pyridine-3-sulfonyl)-amino]-methyl}-phenoxy)-acetic acid was dissolved 100 mM potassium phosphate pH 7.4 at a final substrate concentration of 20 µM. Samples were pre-incubated for 3 min with microsomes (CYP 450; 0.5 µM) at 37° C. in a shaking water bath. Incubations were initiated with the addition of 100 µl cofactor (1.1 mM NADPH, 10 mM MgCl$_2$) per 1 ml of incubation mixture. Incubations were stopped after 30 minutes by the addition of an equal volume of cold acetonitrile.

Hepatocytes Incubations

Human hepatocytes were generated from a mix of 3 livers. Rat and monkey hepatocytes were generated using Sprague Dawley rats (12 livers), Cynomolgus monkey (1 liver) and Beagle dogs (2 livers). Cryopreserved hepatocytes were suspended in William's E media with 10% FBS to a viable count of 2 million cells per ml and gassed with 95/5 $O_2/CO_2$ initially and every hour of incubations. After the addition of 20 µM (3-{[4-tert-butyl-benzyl)-(pyridine-3-sulfonyl)-amino]-methyl}-phenoxy)-acetic acid to a 25 ml Erlenmeyer flask, 2.5 ml of hepatocytes suspension was added and incubated for 4 hours at 37° C. in a shaking water bath.

Sample Analysis
Quantitative Assessment

Metabolite quantification was performed by measuring the areas of individually separated HPLC peaks using the β-RAM (IN/US, Win-flow). The β-RAM provided integrated peak representation printouts in CPM as well as the percentage of the radiolabeled material. The β-RAM was operated using a solid scintillation cell.

Extraction of Metabolites from In-Vitro Matrices

Incubations were stopped by the addition of an equal volume of cold acetonitrile, sonicated and centrifuged at 3000 rpm for 10 minutes. The supernatants were removed and evaporated to dryness under nitrogen. Residues were reconstituted in 50:50 (acetonitrile: water) and aliquots (50–90 µl) were injected onto the HPLC system for analysis.

High Performance Liquid Chromatography

The HPLC system consisted of a HP-1100 solvent delivery system, a HP-1100 membrane degasser, a HP-1100 autoinjector (Hewlett Packard) and an IN/US radioactive monitor (β-RAM). Chromatography was performed on a YMC AQ (C-18) column (4.6 mm×150 mm, 3 µm) (Waters, Milford, Mass.). The mobile phase was initially composed of 10 mM ammonium acetate, pH 3.5 with formic acid (solvent A) and acetonitrile (solvent B). The solvent delivery step gradient program was as follows:

| Time (min) | % Solvent A | % Solvent B |
|---|---|---|
| 0–3 | 90 | 10 |
| 3–25 | 35 | 65 |
| 25–26 | 10 | 90 |
| 26–29 | 10 | 90 |
| 29–31 | 90 | 10 |
| 31–35 | 90 | 10 |

The system was allowed to equilibrate for 10 minutes prior to the next injection. A flow rate of 1.0 ml/min was maintained throughout the analysis.

Mass Spectrometry

Identification of the metabolites was performed using a Finnigan TSQ 7000 triple quadrupole mass spectrometer equipped with an API-2 electrospray interface. The HPLC column effluent was split so that approximately 50 µl/min was introduced into the API interface. The remaining effluent was directed to the flow cell of β-RAM. The β-RAM response was recorded as a real time analog signal by the MS data collection system. The collected data from the radioactivity and MS detectors were separated by the dwell volume of flow from the MS to the radioactivity detector (corresponding to a dwell time of about 0.2 min.). The electrospray voltage operated at −4.5 eV as the mass spectrometer collected data in the positive ion mode. Collision induced dissociation (CID) studies were performed with argon gas in Q2 using collision energy of 30–35 eV and a collision gas thickness of approximately 2.1 mTorr.

Results and Discussion
Turnover in Microsomes

Figure 1D:
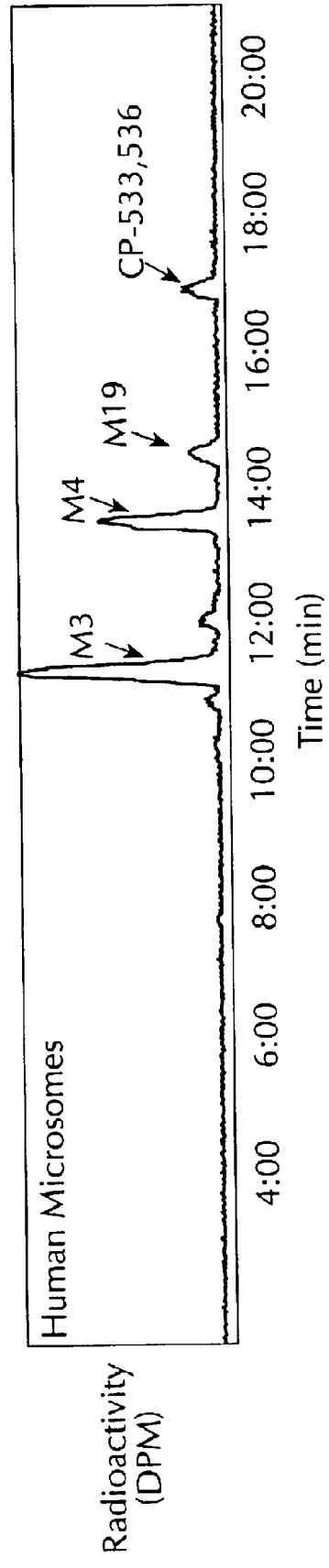

Turnover of (3-{[4-tert-butyl-benzyl)-(pyridine-3-sulfonyl)-amino]-methyl}-phenoxy)-acetic acid in liver microsomes was greatest in rat (94.3%), followed by human (92.8%), monkey (74.9%) and dog (41.6%). Representative HPLC radiochromatograms of microsomal incubations are shown in FIG. 1. Metabolites were quantitated by in-line radioactive counting and relative percentages are presented in Table 1.

Figure 2A:
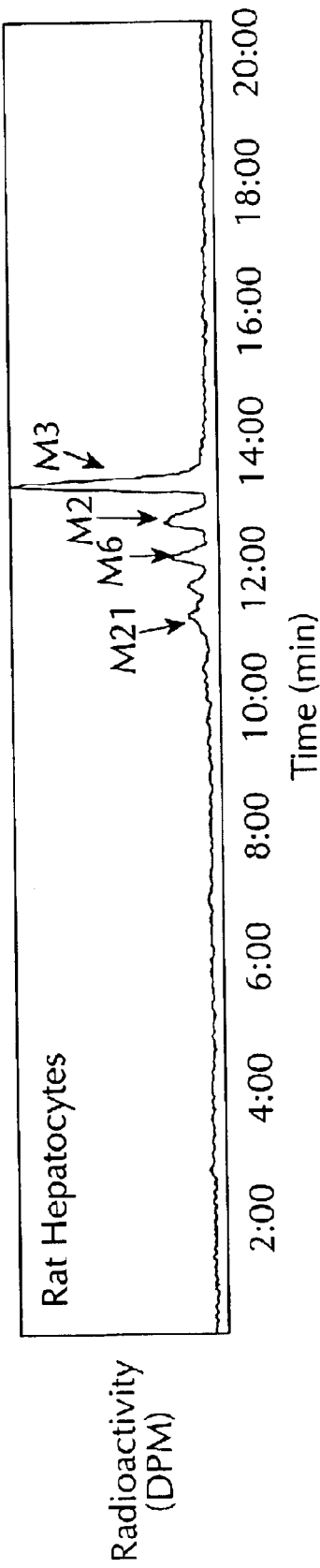
FIG. 2. Representative HPLC radiochromatograms of metabolites of (3-{[4-tert-butyl-benzyl)-(pyridine-3-sulfonyl)-amino]-methyl}-phenoxy)-acetic acid in rat, dog, monkey and human hepatocytes.
Figure 2B:
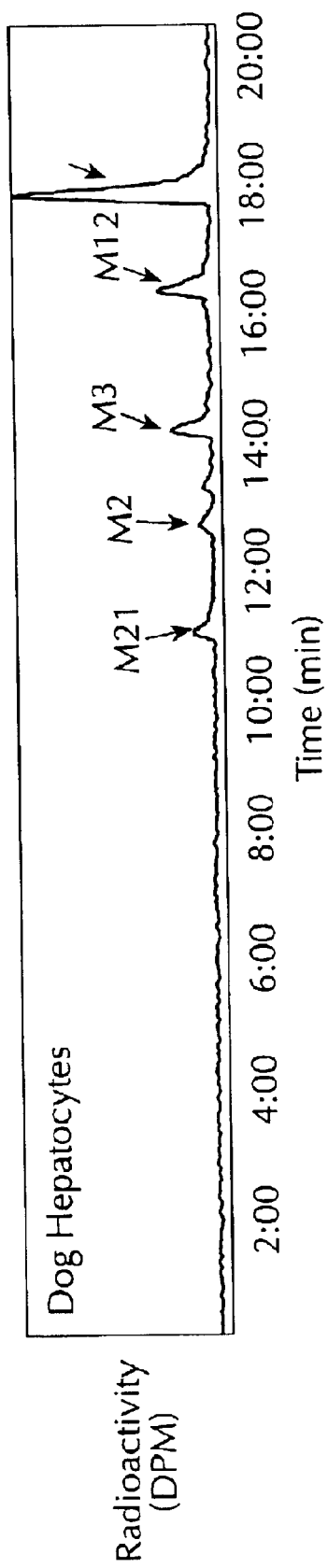

Turnover in Hepatocytes (3-{[4-Tert-butyl-benzyl)-(pyridine-3-sulfonyl)-amino]-methyl}-phenoxy)-acetic acid was incubated with rat, dog, monkey and human liver hepatocytes. Relative turnover rate for the four species was rat=monkey>human>dog. The relative percentages of metabolites in hepatocyte incubations are given in Table 2. Representative HPLC radiochromatograms for hepatocyte incubations are shown in FIG. 2.

Figure 3:
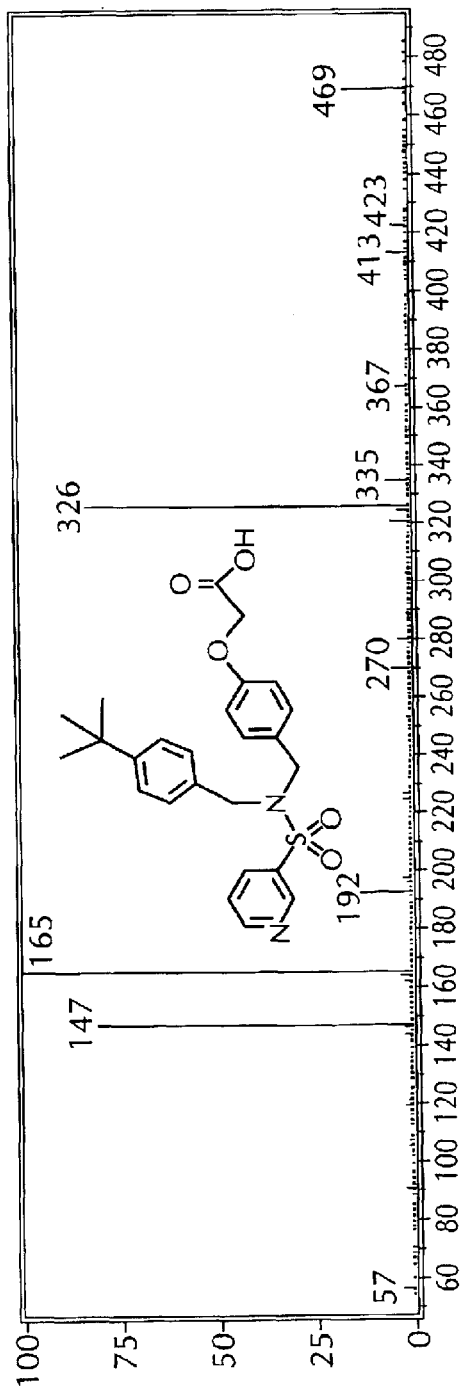
FIG. 3. CID product ion spectrum of (3-{[4-tert-butyl-benzyl)-(pyridine-3-sulfonyl)-amino]-methyl}-phenoxy)-acetic acid (m/z 469).

Fragmentation of (3-{[4-tert-butyl-benzyl)-(pyridine-3-sulfonyl)-amino]-methyl}-phenoxy)-acetic acid by LC/MS/MS (3-{[4-Tert-butyl-benzyl)-(pyridine-3-sulfonyl)-amino]-methyl}-phenoxy)-acetic acid had a retention time of 17–17:28 (min:sec) on HPLC and showed a protonated molecular ion at m/z 469. The CID product ion spectrum of m/z 469 showed prominent fragment ions at m/z 423, 413, 326, 165, and 147 (FIG. 3). The ion at m/z 423 occurred from the loss of formic acid from the molecule. The loss of the t-butyl group resulted in the ion at m/z 413. The ion at m/z 326 resulted from the loss of a sulfonyl pyridine moiety. The ion at m/z 165 was due to a protonated methyl phenoxyacetic acid moiety, and the ion at m/z 147 was due to t-butyl tropolium ion. A proposed fragmentation of (3-{[4-tert-butyl-benzyl)-(pyridine-3-sulfonyl)-amino]-methyl}-phenoxy)-acetic acid is shown below:

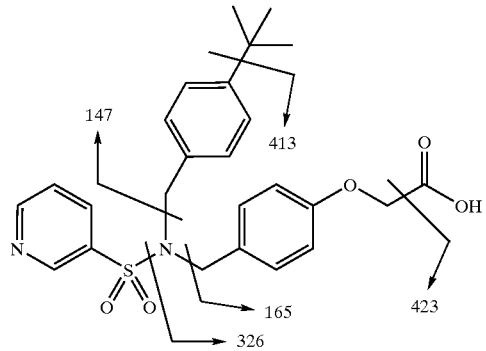

Identification of Metabolites
Metabolite M21

Figure 4:
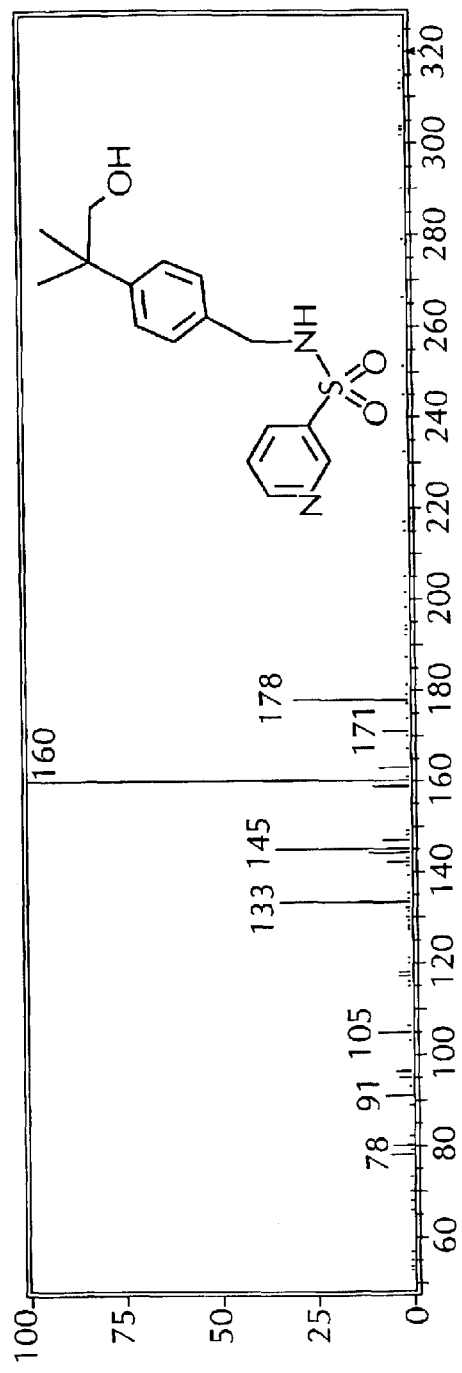
FIG. 4. CID product ion spectrum of metabolite M21 (m/z 321).

Metabolite M21 had a protonated molecular ion at m/z 321 and had a retention time of 10:58 (min:sec) on HPLC. It was found in rat, dog and monkey hepatocytes. The molecular ion at m/z 321 suggested that the parent compound was N-debenzylated and hydroxylated. The CID product ion spectrum of M21 showed prominent ions at m/z 178, 160, 145, 133 and 78 (FIG. 4). The ion at m/z 178 resulted from cleavage of the sulfonamide bond. A loss of water from the ion at m/z 178 resulted in the ion at m/z 160. The ion at m/z 145, two amu lower than that of the parent compound at m/z 147, suggesting that the molecule was hydroxylated on the t-butyl moiety. The ion at m/z 78 was due to charge stabilization on the pyridine ring. Based on these data, the structure of M21 was identified as pyridine-3-sulfonic acid 4-(2-hydroxy-1,1-dimethyl-ethyl)-benzylamide.

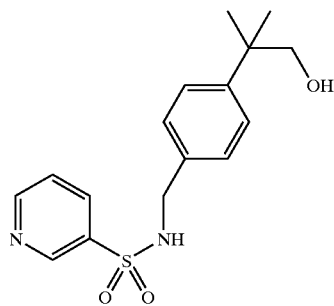

M21

Metabolite M11

Figure 5:
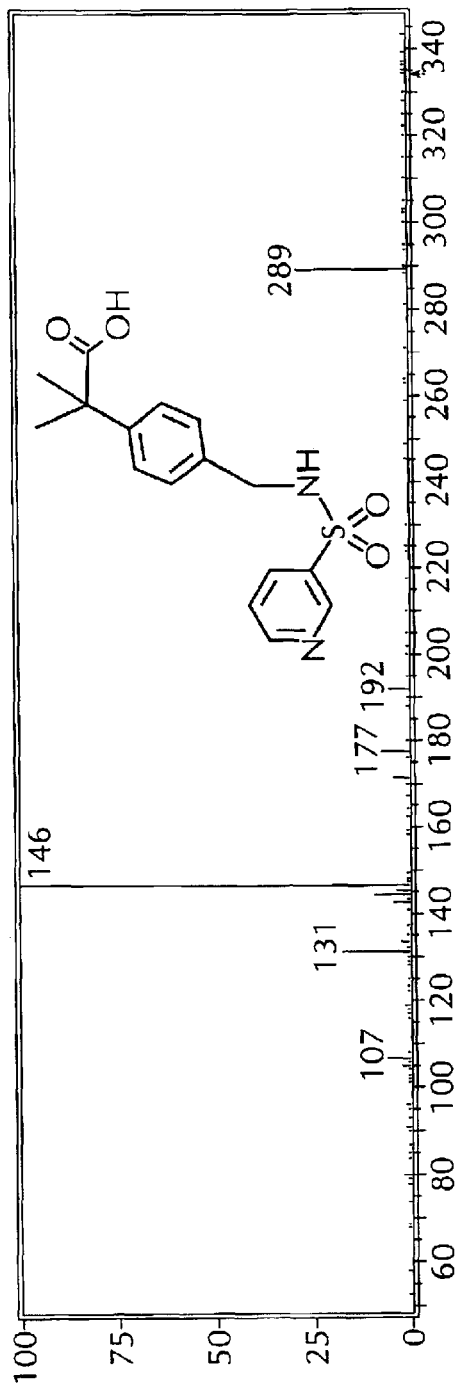
FIG. 5. CID product ion spectrum of metabolite M11 (m/z 335).

Metabolite M11 had a retention time of 9:48–10:48 (min:sec) on HPLC and showed a protonated molecular ion at m/z 335. It was found in rat and monkey liver microsomes. The molecular ion at m/z 335, 134 daltons lower than the parent compound, suggested that it was a cleaved product. The CID product ion spectrum of M11 showed fragments at m/z 289, 146 and 131 (FIG. 5). The ion at m/z 289, a 46 amu loss from the molecular ion, suggested the presence of a carboxylic acid moiety. The ions at m/z 131 and 146 may have resulted from the modified t-butyl benzyl and t-butylbenzylamine moieties with the concomitant loss of the formic acid. Based on its fragmentation pattern and molecular ion, it is suggested that M11 was formed from N-debenzylation of the phenoxyacetic acid moiety, followed by oxidation of the t-butyl moiety to form the carboxylic acid. Thus, it was identified as 2-methyl-2-{4-[(pyridine-3-sulfonylamino)-methyl]-phenyl}-propionic acid.

M11

Metabolite M2

Figure 6:
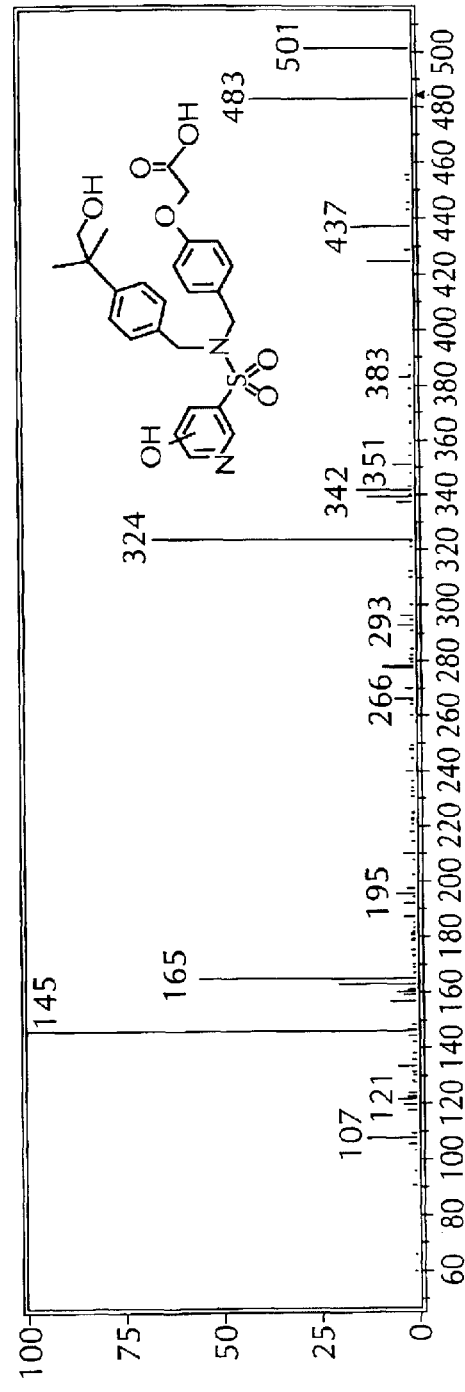
FIG. 6. CID product ion spectrum of metabolite M2 (m/z 501).

Metabolite M2 had a retention time of 12:24 (min:sec) on HPLC and showed a protonated molecular ion at m/z 501 (32 amu higher than the parent compound). M2 was found in rat and dog hepatocytes. It showed prominent fragment ions at m/z 483, 342, 324, 165, and 145 (FIG. 6). The ion at m/z 483 occurred from the loss of water from the molecule. The ion at m/z 342 resulted from the loss of a sulfonyl pyridine moiety, followed by a loss of water to form the ion at m/z 324. The ion at m/z 165, similar to that of the parent compound, was due to the methyl phenoxyacetic acid moiety. The ion at m/z 145 indicated a loss of water from the modified t-butylbenzyl moiety. Based on these data, M2 was identified as dihydroxy (3-{[4-tert-butyl-benzyl)-(pyridine-3-sulfonyl)-amino]-methyl}-phenoxy)-acetic acid. It is noted that when this chemical name is used in the application, the position of the hydroxyl group on the pyridyl ring is not specified and the name is intended to encompass each of the possible positions of the hydroxyl group.

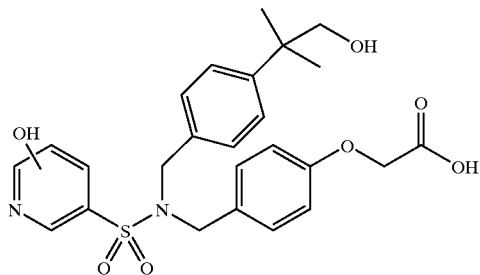

M2

Metabolite M3

Metabolite M3 had a retention time of 11:55–13:54 (min:sec) on HPLC and showed a protonated molecular ion at m/z 499 (30 amu higher than the parent compound). It was found in rat, monkey and human liver microsomes and hepatocytes of all species. The CID product ion spectrum of M3 showed prominent fragments at m/z 453, 356, 310, 177, 165 and 131 (FIG. 7). The ion at m/z 165 was similar to that of the parent compound, suggesting that the methylphenoxy acetic acid moiety was unchanged. The ion at m/z 356 was 30 amu higher than that observed in the parent compound, suggesting the addition of two atoms of oxygen and a loss of two hydrogen atoms. The ions at m/z 310 and 131 were due to a loss of 46 amu from the ions at m/z 356 and 177, respectively, suggesting the presence of a carboxylic acid moiety. Based on these data, metabolite M3 was identified as carboxy (3-{[4-tert-butyl-benzyl)-(pyridine-3-sulfonyl)-amino]-methyl}-phenoxy)-acetic acid.

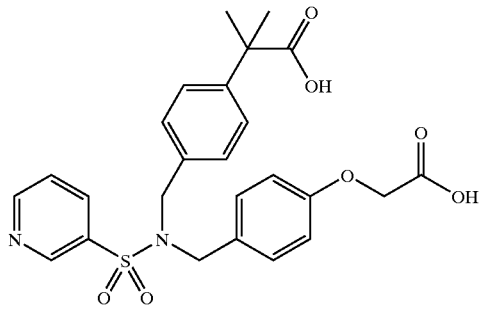

M3

Metabolite M4

Metabolite M4 had a retention time of 13:29 (min:sec) on HPLC and showed a protonated molecular ion at m/z 485 (16 amu higher than the parent compound). It was found in rat, monkey, dog and human liver microsomes and human hepatocytes. Its CID product ion spectrum showed prominent fragment ions at m/z 467, 342, 335, 324, 165, and 145 (FIG. 8). The ion at m/z 467 occurred from the loss of water from the molecule. The ion at m/z 342 resulted from the loss of a sulfonyl pyridine moiety, followed by a loss of water to form the ion at m/z 324. The ion at m/z 165, similar to that of the parent compound, was due to a protonated methylphenoxy acetic acid moiety. The ion at m/z 145 indicated a loss of water from the modified t-butyl benzyl moiety. Based on these data, M4 was identified as hydroxy (3-{[4-tert-butylbenzyl)-(pyridine-3-sulfonyl)-amino]-methyl}-phenoxy)-acetic acid.

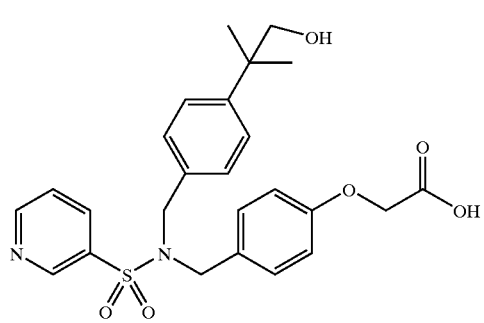

M4

Metabolite M19

Figure 9:
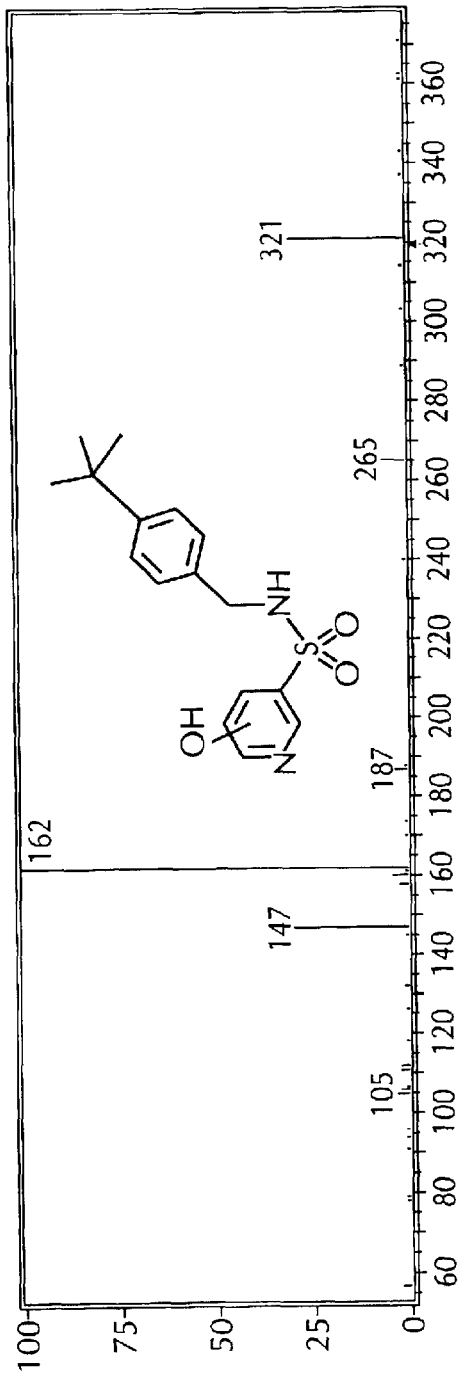
FIG. 9. CID product ion spectrum of metabolite M19 (m/z 321).

Metabolite M19 had a retention time of 14:40 on HPLC and showed a protonated molecular ion at m/z 321 (148 amu lower than the parent compound). It was found in all species of microsomes analyzed. The CID product ion spectrum of M19 showed prominent fragment ions at m/z 321, 265, 162 and 147 (FIG. 9). The ions at m/z at m/z 162 and 147 were observed in the CID product ion spectrum of the parent compound, suggesting that the phenyl t-butyl group was unchanged and the molecule had undergone N-dealkylation. The ion at m/z 265 resulted from the loss of the t-butyl moiety, suggesting that an oxidation had occurred on the pyridine moiety. Based on this data, M19 was identified as 5-hydroxy-pyridine-3-sulfonic acid 4-tert-butyl-benzylamide. It is noted that when this chemical name is used in the application, the position of the hydroxyl group on the pyridyl ring is not specified and the name is intended to encompass each of the possible positions of the hydroxyl group.

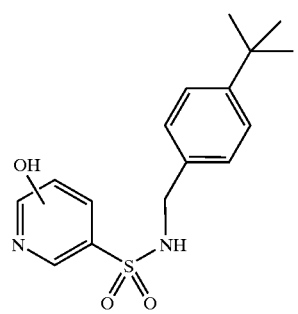

M19

Metabolite M6

Figure 10:
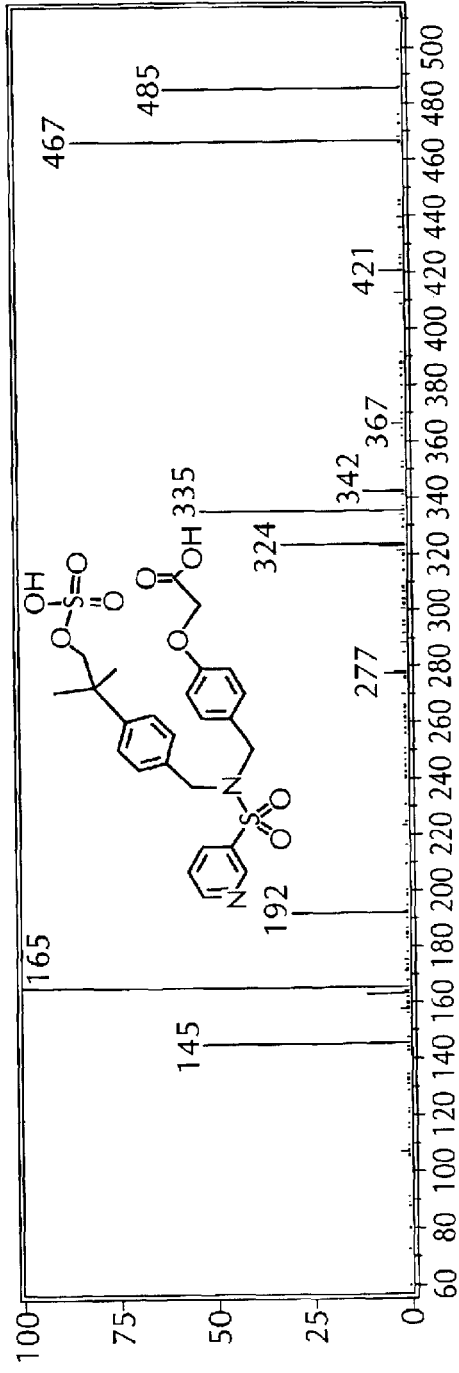
FIG. 10. CID product ion spectrum of metabolite M6 (m/z 565).

Metabolite M6 had a retention time of 11:52 (min:sec) on HPLC and showed a protonated molecular ion at m/z 565, 96 amu higher than the parent compound, suggesting the addition of an atom of oxygen and a sulfate group. M6 was found in rat, monkey and human hepatocytes. The CID product ion spectrum of M6 showed prominent fragments at m/z 485, 467, 342, 324, 165 and 145 (FIG. 10). The ions at m/z 485 and 467 were due to losses of sulfate and water from the protonated molecular ion. The ion at m/z 165 was similar to that of the parent compound indicating that the methyl-phenoxy acetic acid moiety was not changed. The ion at m/z 342 (16 amu higher than that observed in the parent compound) indicated that the addition of an oxygen atom had occurred on the t-butyl benzyl moiety. The ions at m/z 324 and 145 were 2 amu lower than those corresponding in the spectrum of the parent compound, again suggested an addition of oxygen to the t-butyl benzyl moiety, and upon fragmentation a molecule of water was lost. Based on these data, M6 was identified as the sulfate conjugate of hydroxy-(3-{[4-tert-butyl-benzyl)-(pyridine-3-sulfonyl)-amino]-methyl}-phenoxy)-acetic acid.

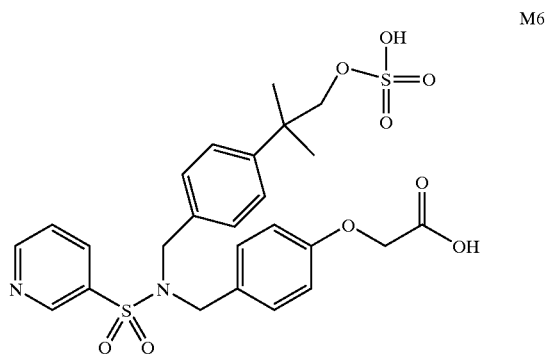

M6

Metabolite M5

Figure 11:
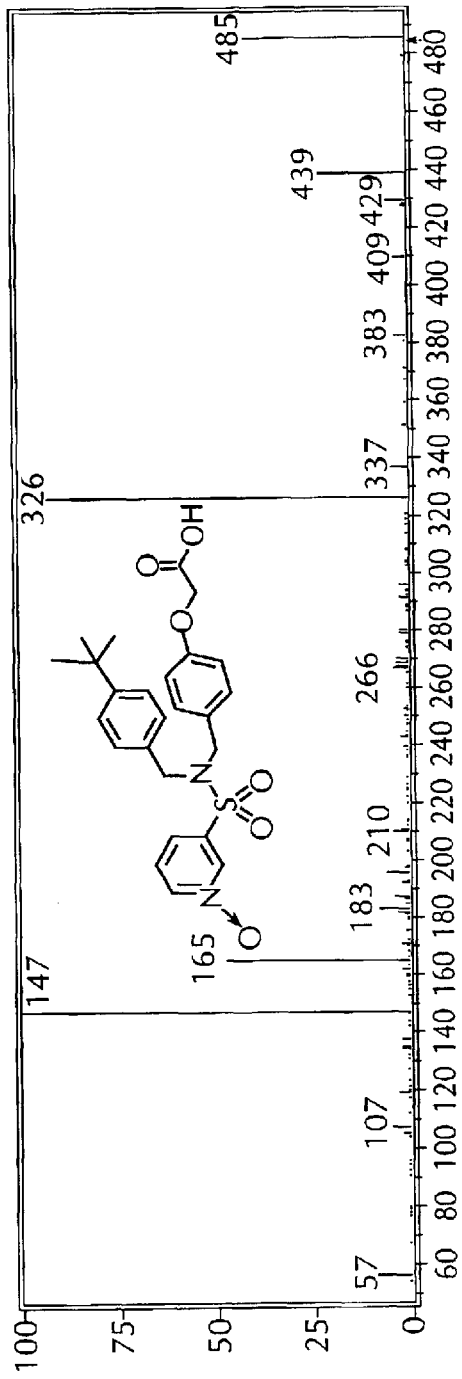
FIG. 11. CID product ion spectrum of metabolite M5 (m/z 485).

Metabolite M5 had a retention time of about 15:29 min on HPLC and showed a protonated molecular ion at m/z 485 (16 amu higher than the parent compound). M5 was present in rat, dog, monkey and human liver microsomes. The CID product ion spectrum of m/z 485 showed prominent fragment ions at m/z 439, 326, 165, and 147 (FIG. 11). The ions at m/z 326, 147 and 165 were all similar to those seen in the CID spectrum of the parent compound and suggested that the phenyl t-butyl and the phenoxy acetic acid moieties was unmodified. The ion at m/z 439 was 16 amu higher than that observed in the parent compound. This data suggested that the pyridine moiety was hydroxylated. Additionally, treatment of this metabolite with titanium trichloride resulted in disappearance of the peak at 15.3 min, and resulted in an increase of the relative area of (3-{[4-tert-butyl-benzyl)-(pyridine-3-sulfonyl)-amino]-methyl}-phenoxy)-acetic acid in the chromatogram, suggesting that M5 was the N-oxide of the parent compound. Based on these data M5 was identified as (3-{[4-tert-butyl-benzyl)-(pyridine-3-sulfonyl)-amino]-methyl}-phenoxy)-acetic acid N-oxide.

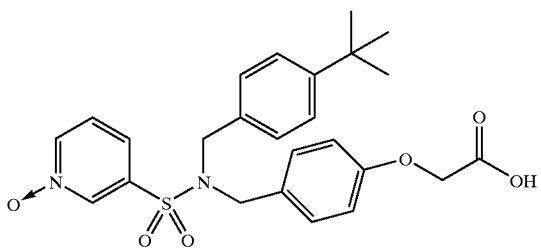

M5

Metabolite M12

Figure 12:
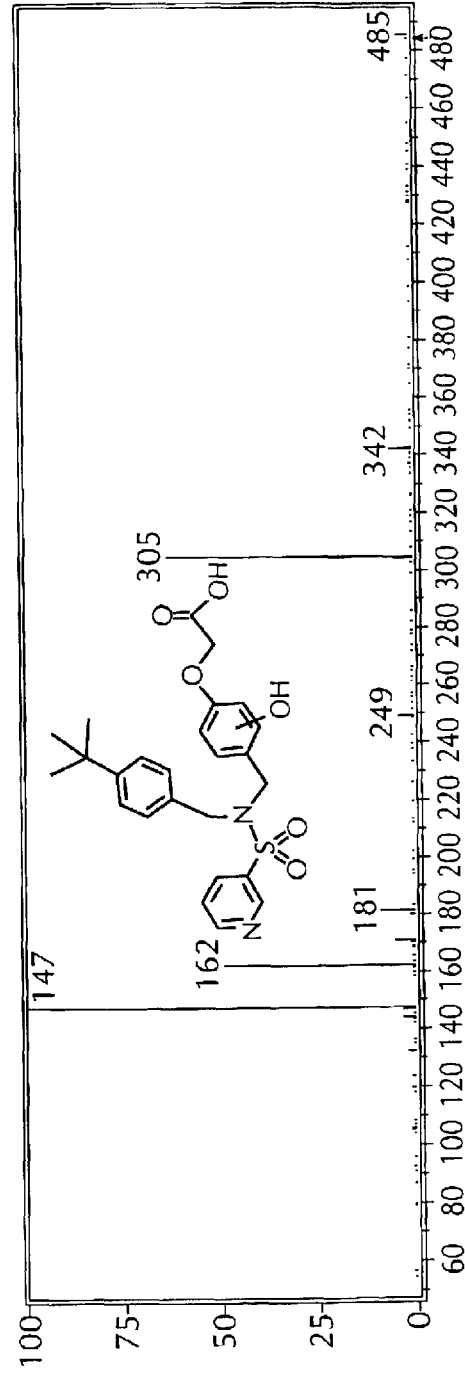
FIG. 12. CID product ion spectrum of metabolite M12 (m/z 485).

Metabolite M12 had a retention time of about 16:01 (min:sec) on HPLC and was found only in dog liver microsomes. It showed a protonated molecular ion at m/z 485 (16 amu higher than the parent compound). The CID product ion spectrum of metabolite M12 showed prominent fragments at m/z 485, 342, 305, 181, 162 and 147 (FIG. 12). The ions at m/z 162 and 147 were similar to those seen in the parent compound, suggesting that the t-butyl benzyl moiety was unchanged. The ions at m/z 181 and 342 were 16 amu higher than those observed in the parent compound (m/z 165 and 326, respectively), indicating the addition of an oxygen atom to the methyl-phenoxy acetic acid moiety. The ion at m/z 305 was due to loss of the phenoxy acetic acid moiety. Based on these data, M12 was identified as hydroxy (3-{[4-tert-butyl-benzyl)-(pyridine-3-sulfonyl)-amino]-methyl}-phenoxy)-acetic acid. It is again noted that when this chemical name is used in the application, the position of the hydroxyl group on the phenyl ring is not specified and the name is intended to encompass each of the possible positions of the hydroxyl group.

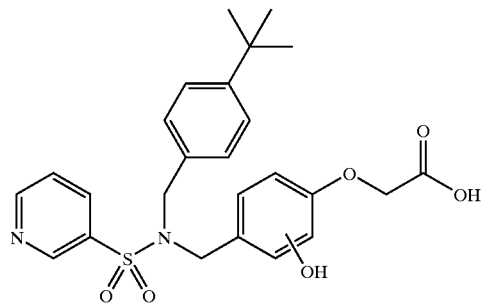

M12

Metabolite M20

Figure 13:
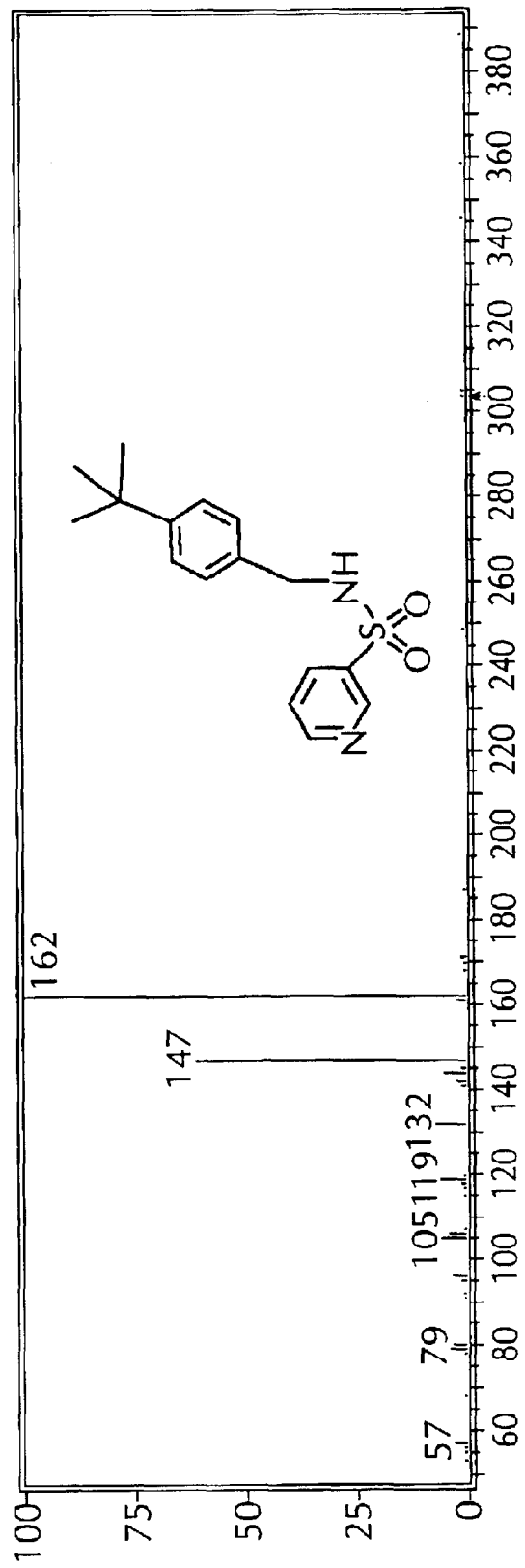
FIG. 13. CID product ion spectrum of metabolite M20 (m/z 305).

Metabolite M20 had a retention time of about 19:45 min on HPLC and showed a protonated molecular ion at m/z 305 (164 amu lower than the parent compound). The CID product ion spectrum of M20 showed prominent fragment ions at m/z 162 and 147 (FIG. 13). These ions were observed in the CID product ion spectrum of the parent compound, and therefore, suggested that the (3-{[4-tert-butyl-benzyl)-(pyridine-3-sulfonyl)-amino]-methyl}-phenoxy)-acetic acid had undergone N-dealkylation resulting in the cleaved metabolite at m/z 305. Based on these data M20 was identified as pyridine-3-sulfonic acid 4-tert-butyl-benzylamide.

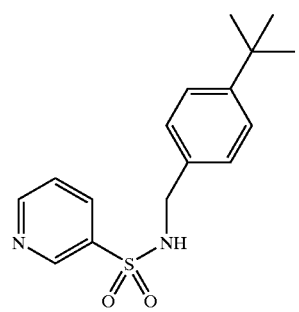

M20

(3-{[4-Tert-butyl-benzyl)-(pyridine-3-sulfonyl)-amino]-methyl}-phenoxy)-acetic acid was extensively metabolized in rat, dog, monkey, and human liver microsomes and hepatocytes. The proposed metabolic pathways are shown in Scheme 2. The major metabolic pathways were due to oxidation of the t-butyl moiety to form an alcohol, oxidation of the pyridine moiety, and/or N-dealkylation of the methylphenoxy acetic acid moiety. The alcohol metabolite M4 was further oxidized to corresponding carboxylic acid M3. In hepatocytes, M4 was conjugated with sulfuric acid. In dog hepatocytes, one of the metabolite M12 was due to aromatic oxidation of the methylphenoxy acetic acid moiety.

TABLE 1

Percentage of Metabolites of (3-{[4-tert-butyl-benzyl)-(pyridine-3-sulfonyl)-amino]-methyl}-phenoxy)-acetic acid in Rat, Dog, Monkey and Human Liver Microsomes

| Metabolite Number | RT | M/z | Percent of Radioactivity | | | |
|---|---|---|---|---|---|---|
| | | | Rat | Dog | Monkey | Human |
| M11 | 9:48 | 335 | 20.7 | — | 7.97 | — |
| M3 | 11:55 | 499 | 56.2 | — | 8.80 | 50.0 |
| M4 | 13:29 | 485 | 4.38 | 11.5 | 47.3 | 26.5 |
| M19 | 14:40 | 321 | 3.26 | 3.61 | 4.37 | 7.06 |
| M5 | 15:29 | 485 | 7.80 | 20.1 | 5.21 | — |
| parent | 17:00 | 469 | 5.70 | 58.4 | 25.2 | 7.16 |
| M20 | 19:45 | 305 | — | 1.96 | — | — | parent compound is (3-{[4-tert-butyl-benzyl)-(pyridine-3-sulfonyl)-amino]-methyl}-phenoxy)-acetic acid;
RT is retention time in minutes:seconds.

TABLE 2

Percentage of Metabolites of (3-{[4-tert-butyl-benzyl)-(pyridine-3-sulfonyl)-amino]-methyl}-phenoxy)-acetic acid in Rat, Dog, Monkey and Human Hepatocytes

| Metabolite Number | RT | M/z | Percent of Radioactivity | | | |
|---|---|---|---|---|---|---|
| | | | Rat | Dog | Monkey* | Human* |
| M21 | 10:58 | 321 | 8.91 | 7.92 | 4.53 | — |
| M6 | 11:52 | 565 | 9.55 | — | 52.9 | 29.6 |
| M2 | 12:24 | 501 | 15.1 | 6.59 | — | — |
| M3 | 13:54 | 499 | 57.3 | 12.3 | 29.9 | 17.8 |
| M4 | 13:29 | 485 | — | — | — | 41.2 |
| M12 | 16:01 | 485 | — | 15.0 | — | — |
| Parent | 17:28 | 469 | — | 51.4 | — | 5.68 |

*Monkey and Human hepatocytes samples were analyzed by HPLC using the same gradient and column, except the mobile phase contained ammonium acetate (10 mM), pH 5.0. Retention times given are specified for the gradient specified above.

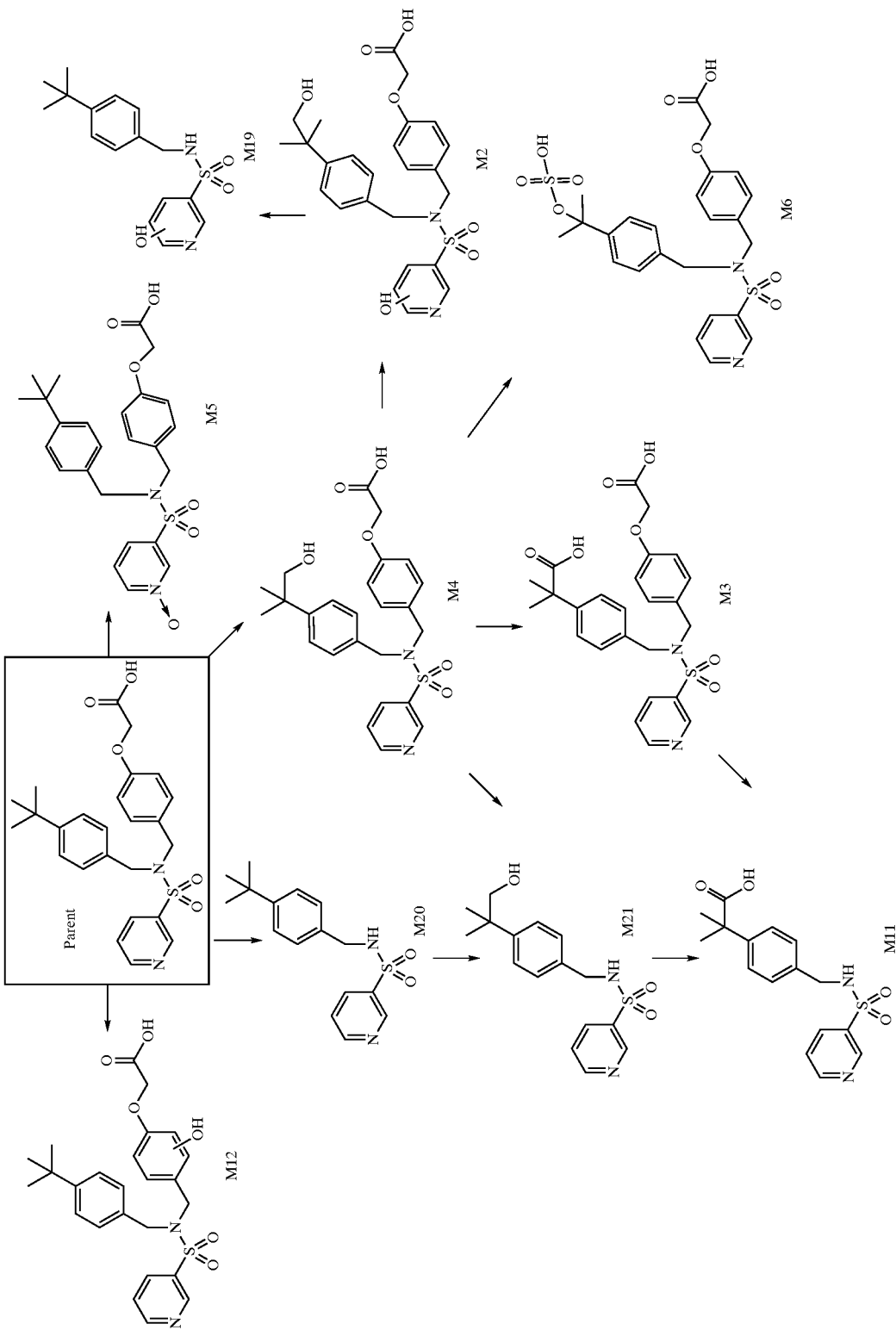
Scheme 2. Proposed metabolic pathways of $^{14}$C-(3-{[(4-tert-butyl-benzyl)-(pyridine-3-sulfonyl)-amino]-methyl}-phenoxy)-acetic acid following in-vitro incubation in liver microsomes and hepatocytes.

Generation of Metabolites using Recombinant Human P-450

Recombinant human cytochrome P-450 isoforms rCYP3A4, rCYP3A5 and rCYP2C8 were purchased from Gentest (Woburn, Mass). The quantities of expressed rCYP used in each incubation were approximately 1 mg protein/ml of incubation. Prior to use, microsomes were thawed on ice and reconstituted using 100 mM potassium phosphate pH 7.4 containing (3-{[[4-tert-butyl-benzyl)-(pyridine-3-sulfonyl)-amino]-methyl}-phenoxy)-acetic acid (50 μM). Samples were preincubated for 3 min with recombinant CYPs at 37° C. in a shaking water bath. Incubations were initiated with the addition of 100 μl cofactor (1.1 mM NADPH, 10 mM MgCl$_2$). After 60 minutes of incubations, the samples were acidified to pH 3.0 with acetic acid and extracted against an equal volume of methyl-tert-butyl ether (MTBE). The MTBE layer was evaporated under nitrogen gas until dryness and reconstituted in 10 mM ammonium acetate: acetonitrile (1:1) for analysis for LC/MS.

LC/MS Structure Characterization of P-450 Metabolites

The HPLC system consisted of a HP-1100 solvent delivery system, a HP-1100 membrane degasser, a HP-1100 autoinjector (Hewlett Packard) and an IN/US radioactive monitor (β-RAM). Chromatography was performed on a YMC ODS AQ (C-18) column (4.6 mm×150 mm, 3 μm). The mobile phase was initially composed of 10 mM ammonium acetate, pH 5.0 with acetic acid (solvent A) and acetonitrile (solvent B). Identification of the metabolites was performed using a Micromass Q-Tof 2 (Beverly, Mass.) mass spectrometer equipped with an electrospray interface. The HPLC column effluent was split so that approximately 50 μl/min was introduced into the API interface. The remaining effluent was directed to the flow cell of β-RAM. The β-RAM response was recorded as a real time analog signal by the MS data collection system. The collected data from the radioactivity and MS detectors were separated by the dwell volume of flow from the MS to the radioactivity detector (corresponding to a dwell time of ~0.1 min.). The electrospray voltage operated at −3 eV as the mass spectrometer collected data in the positive ion mode. Collision induced dissociation (CID) studies were performed with argon gas in Q2 using collision energy of 20–30 eV and a penning pressure of ~5×10−5 torr. An internal lock mass (quinidine, m/z 325.1916) was used throughout the analyses via an indexed Lockspray allowing for the calibrant to be introduced into the mass spectrometer every 5 seconds.

Figure 14A:
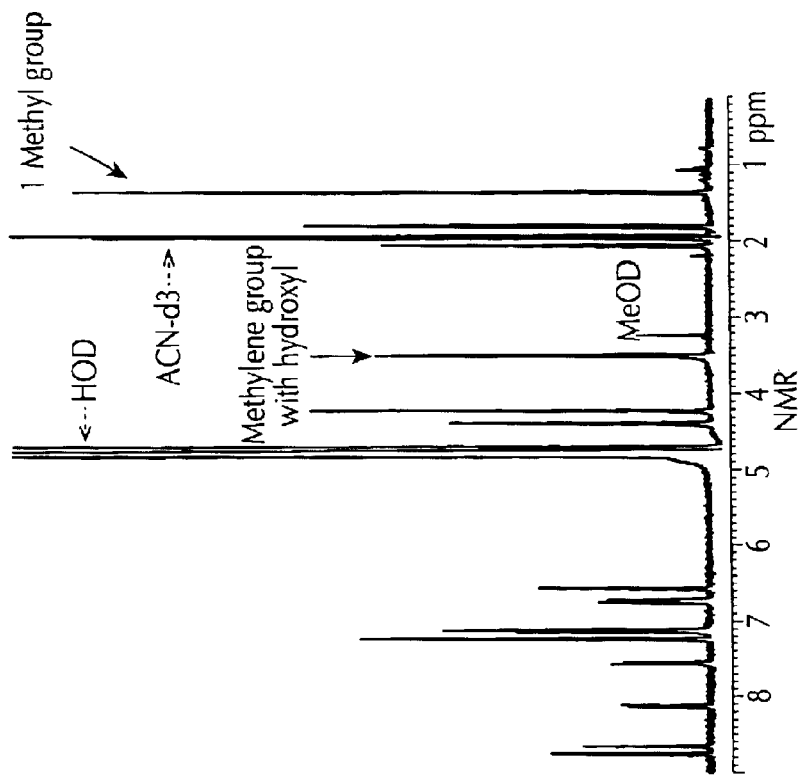
FIG. 14. CID product ion spectrum and $^1$H NMR of metabolite M22 (m/z 487).
Figure 14B:
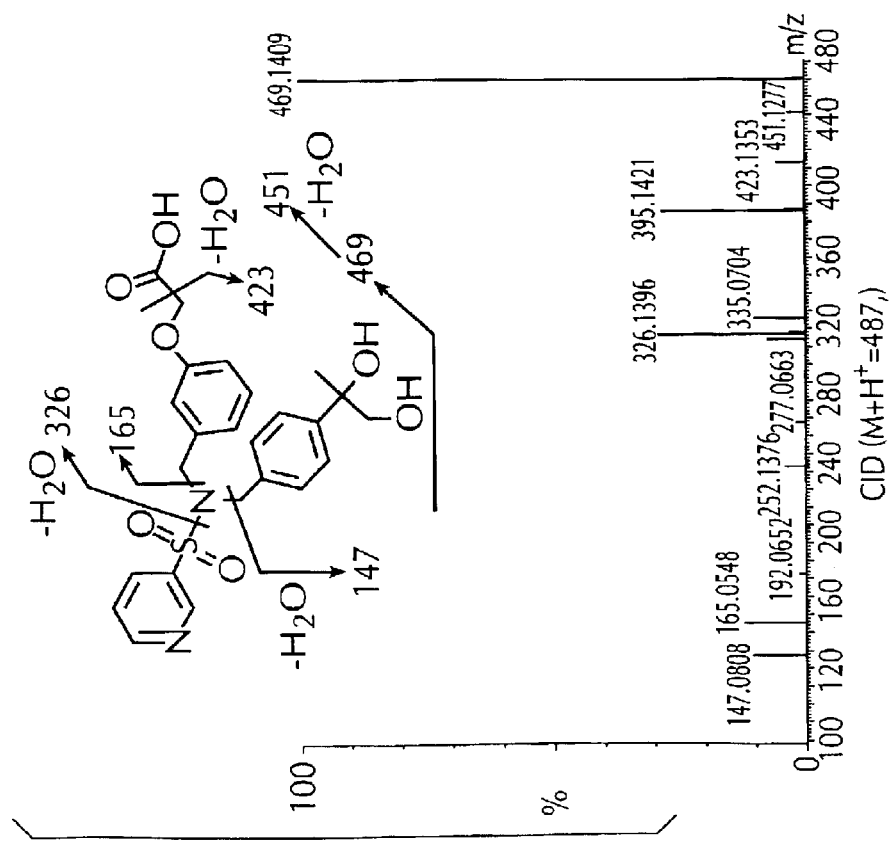

Metabolite M22; (3-{[[4-(1,2-dihydroxy-1-methyl-ethyl)-benzyl]-(pyridine-3-sulfonyl)-amino]-methyl}-phenoxy)-acetic acid Metabolite M22 had a retention time of 14 min on HPLC and a protonated molecular ion at m/z 487 (18 amu higher than the parent compound). The CID product ion spectrum of M2 showed prominent fragment ions at m/z 469, 451, 423, 395, 335, 326, 165, and 147 (FIG. 14).The ion at m/z 165 was similar to that observed in the parent drug, suggesting that the phenoxy acetic acid moiety was unchanged. The ions at m/z 469 and 451, two consecutive losses of 18 amu from the protonated molecular ion suggested that two molecules of water had been lost. Empirical formula information was obtained from high resolution mass spectrum (Q-Tof) suggested an empirical formula of $C_{24}H_{27}N_2O_7S$. Based on these data and supporting LC-NMR data, M22 was identified as (3-{[[4-(1,2-dihydroxy-1-methyl-ethyl)-benzyl]-(pyridine-3-sulfonyl)-amino]-methyl}-phenoxy)-acetic acid.

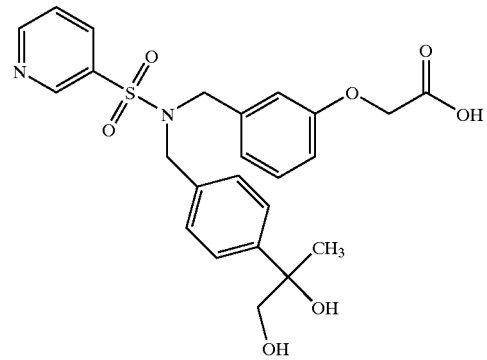

Figure 15B:
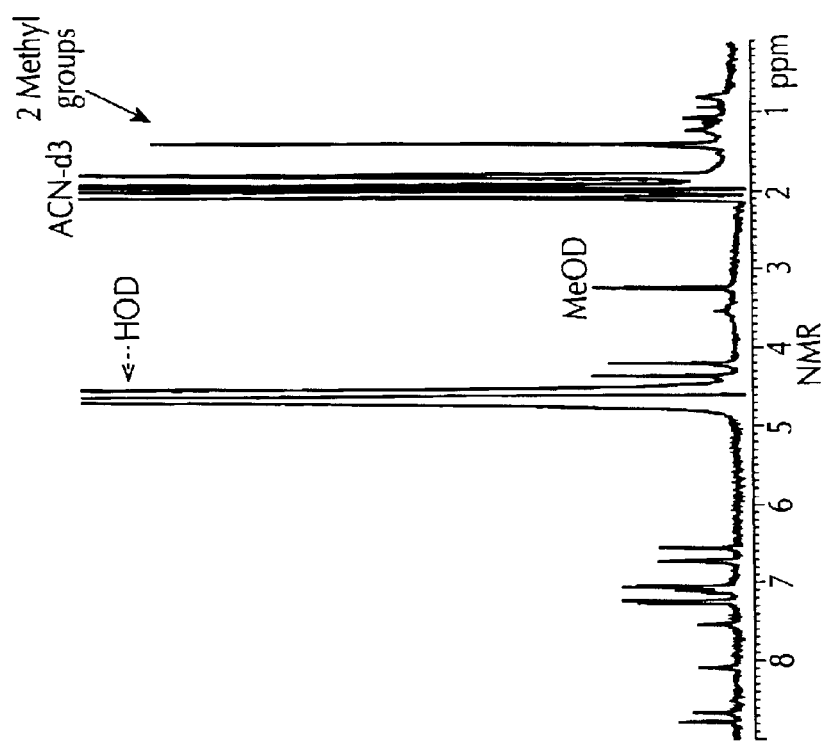
FIG. 15. CID product ion spectrum and $^1$H NMR of metabolite M23 (m/z 471).
Figure 15A:
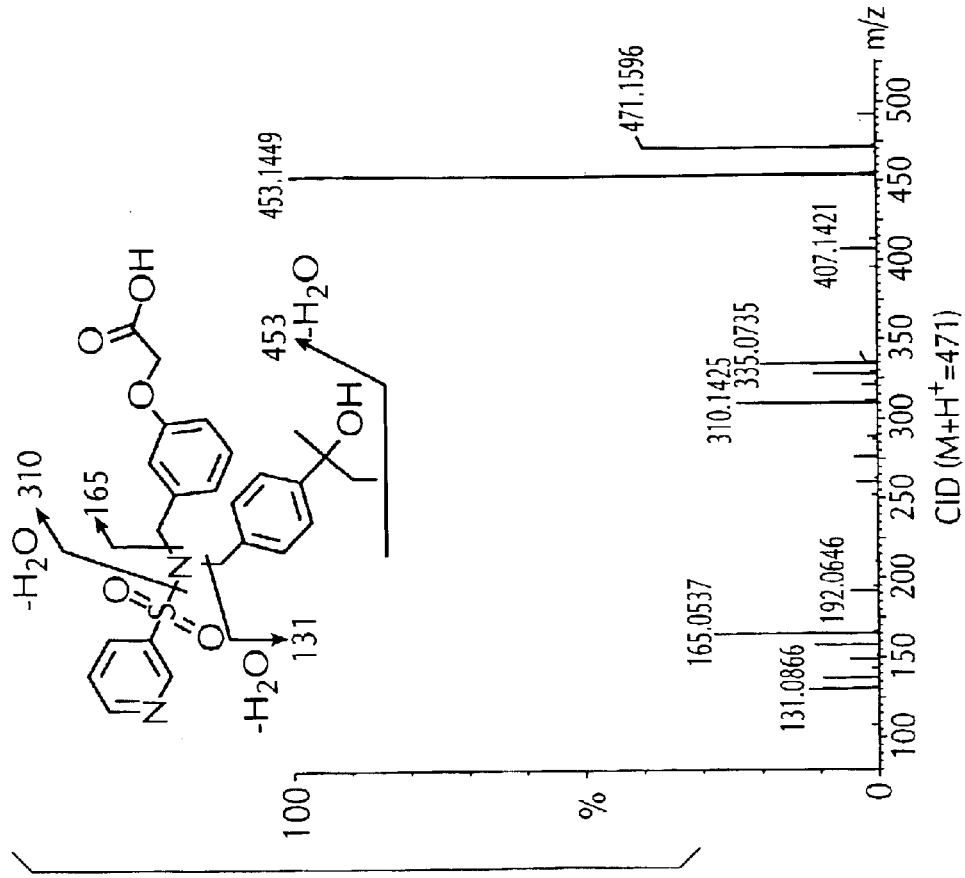

Metabolite M23; (3-{[[4-(1-hydroxy-1-methyl-ethyl)-benzyl]-(pyridine-3-sulfonyl)-amino]-methyl}-phenoxy)-acetic acid Metabolite M23 had a retention time of 16.9 on HPLC and a protonated molecular ion at m/z 471 (2 amu higher than the parent compound). The CID product ion spectrum of M23 showed prominent fragment ions at m/z 453, 335, 310, 165, and 131 (FIG. 15). The ion at m/z 165 was similar to that observed in the parent compound, suggesting that the phenoxy acetic acid moiety was unchanged. The ion at m/z 453, a loss of 18 amu from the protonated molecular ion suggested that a molecule of water had been lost. The ions at m/z 310 and 131 (16 amu lower than those observed in the parent compound) suggested that a methyl group was replaced by a molecule of water then lost during fragmentation. Based on these data and supporting LC-N MR data, M23 was identified as (3-{[[4-(1-hydroxy-1-methyl-ethyl)-benzyl]-(pyridine-3-sulfonyl)-amino]-methyl}-phenoxy)-acetic acid.

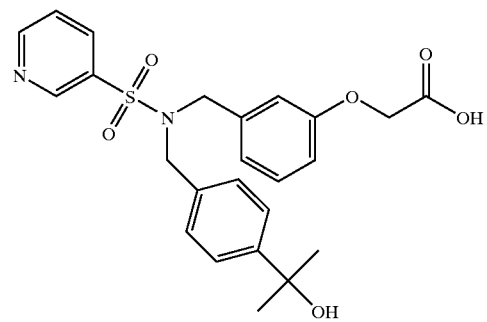

Figure 16B:
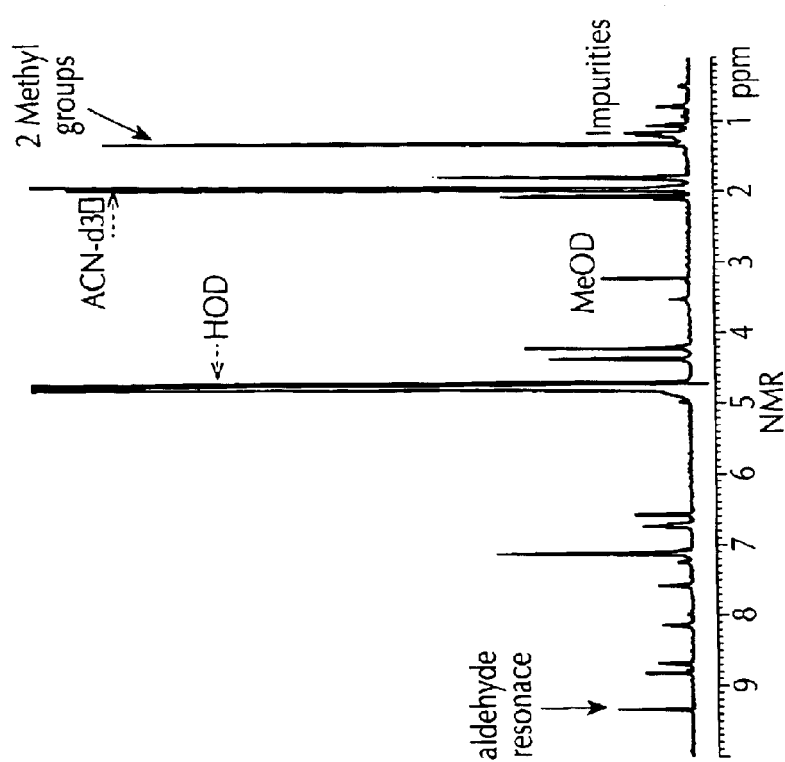
FIG. 16. CID product ion spectrum and $^1$H NMR of metabolite M24 (m/z 483).
Figure 16A:
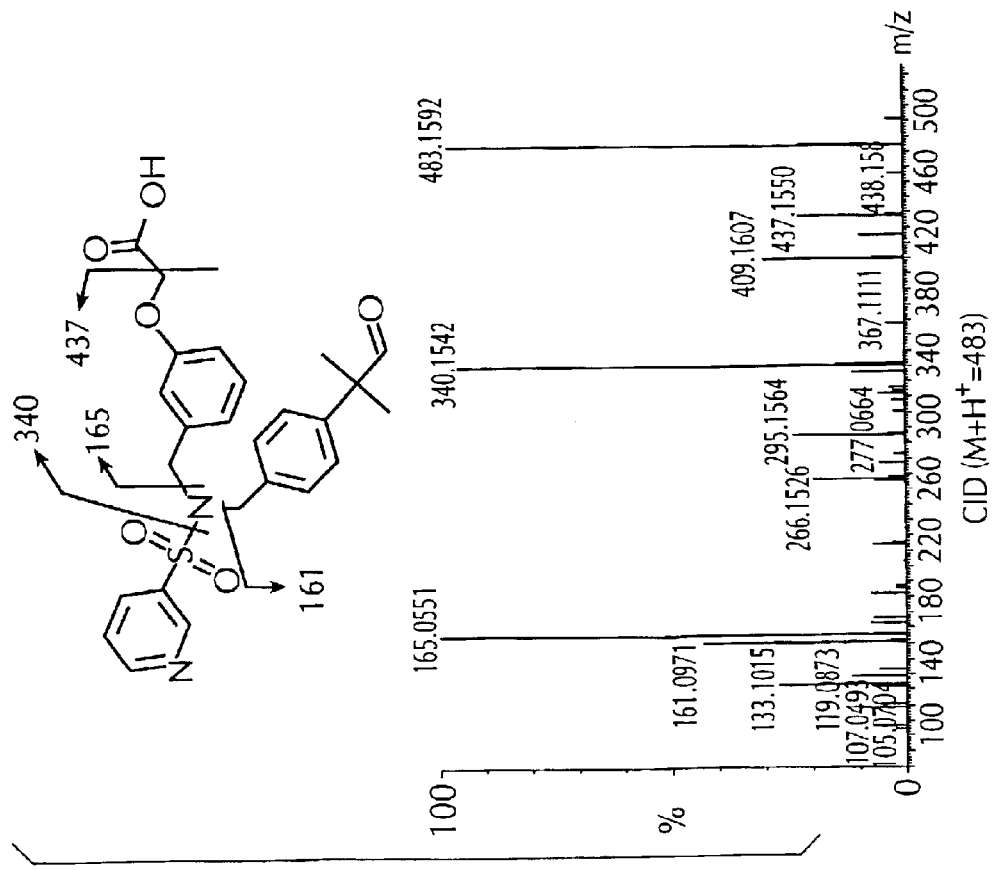

Metabolite M24; (3-{[[4-(1,1-dimethyl-2-oxo-ethyl)-benzyl]-(pyridine-3-sulfonyl)-amino]-methyl}-phenoxy)-acetic acid Metabolite M24 had a retention time of 18.6 min on HPLC and a protonated molecular ion at m/z 483 (14 amu lower than the parent compound). The CID product ion spectrum of M24 showed prominent fragment ions at m/z 483, 437, 409, 340, 165 and 161 (FIG. 16). The ions at m/z 423, 340 and 161 were 14 amu higher than those observed in the spectrum of the parent drug, suggesting an addition of an atom of oxygen with a concomitant loss of two hydrogen atoms. High resolution mass spectra obtained for this metabolite produced a molecular weight of 483.1590 and an empirical formula of $C_{25}H_{27}N_2O_6S$. Based on these data and supporting LC-NMR data, M24 was identified as (3-{[[4-(1,1-dimethyl-2-oxo-ethyl)-benzyl]-(pyridine-3-sulfonyl)-amino]-methyl}-phenoxy)-acetic acid.

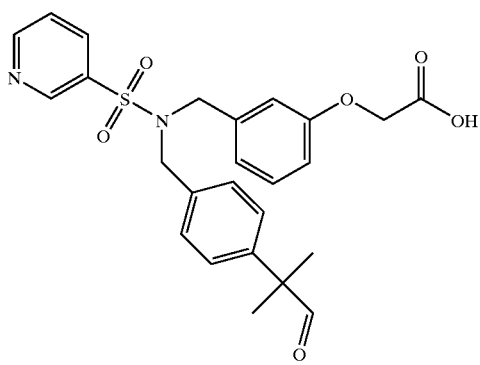

Figure 17B:
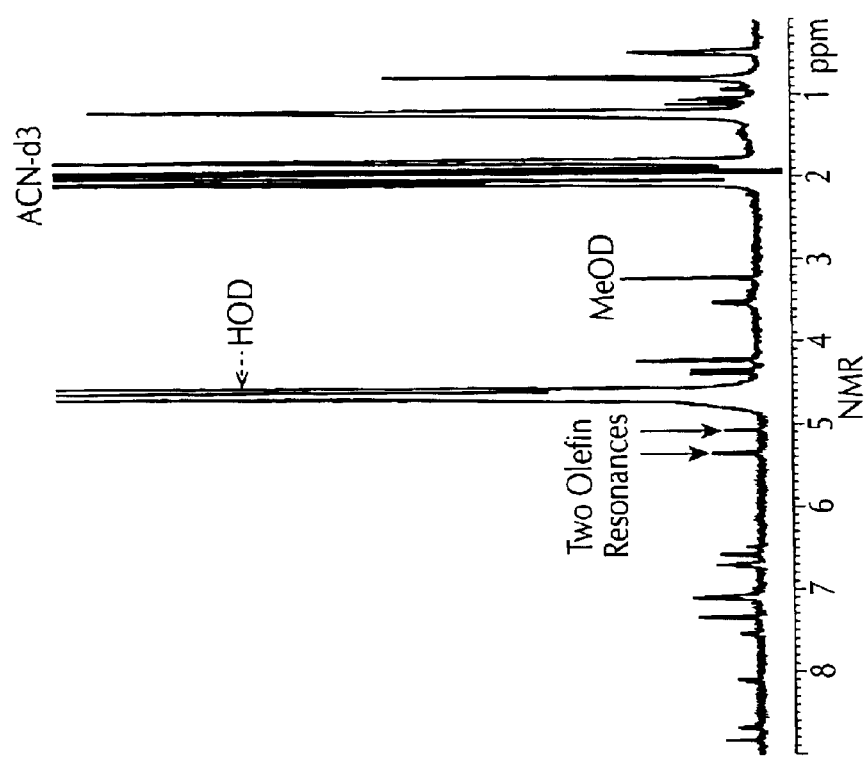
FIG. 17. CID product ion spectrum and $^1$H NMR of metabolite M26 (m/z 453).
Figure 17A:
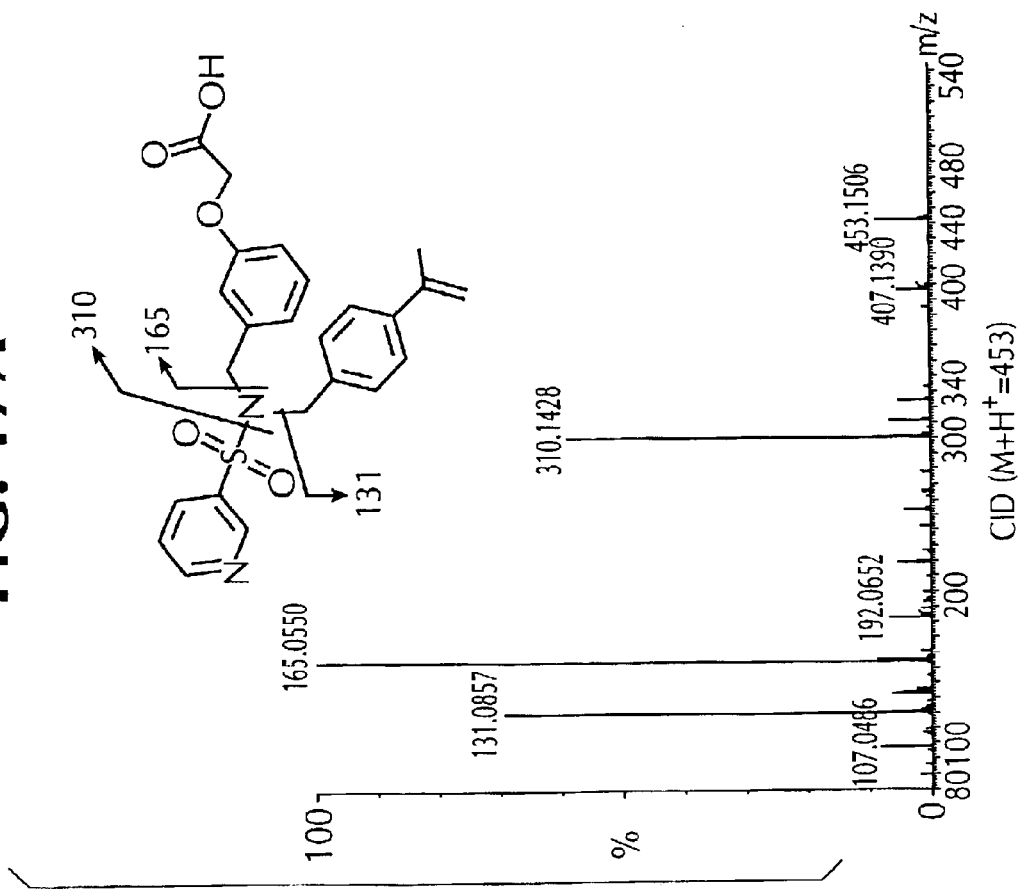

Metabolite M26; (3-{[(4-isopropenyl-benzyl)-(pyridine-3-sulfonyl)-amino]-methyl}-phenoxy)-acetic acid Metabolite M26 had a retention time of 22 min on HPLC and a protonated molecular ion at m/z 453 (16 amu lower than the parent compound). The CID product ion showed prominent fragment ions at m/z 453, 407, 310, 165, and 131 (FIG. 17). The ion at m/z 165 was similar to that observed in the parent compound, suggesting that the phenoxy acetic acid moiety was unchanged. The ions at 407, 310 and 131 were 16 amu lower than the ions observed in the spectrum of parent compound, suggesting that 16 mass units were lost from the t-butyl moiety. High resolution mass spectra obtained for this metabolite produced a molecular weight of 453.1487 and a suggested empirical formula of $C_{24}H_{25}N_2O_5S$. These data combined with the LC-NMR for this metabolite are consistent with the formation of a terminal olefin group as (3-{[(4-isopropenyl-benzyl)-(pyridine-3-sulfonyl)-amino]-methyl}-phenoxy)-acetic acid.

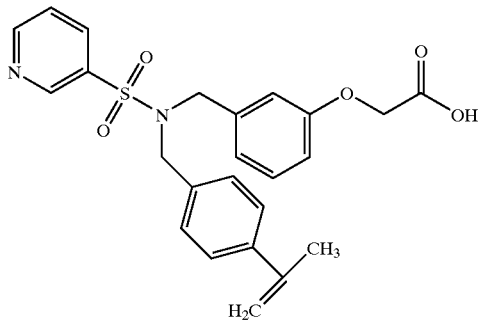

Synthetic Protocols

The following preparations relate to the synthesis of intermediates used in the synthesis of the compounds of Examples 1 and 2.

Preparation 1

{3-[(Pyridine-3-sulfonylamino)-methyl]-phenoxy}-acetic acid tert-butyl ester

Step A (3-Formyl-phenoxy)-acetic acid tert-butyl ester. To a solution of 3-hydroxybenzaldehyde (5.00 g, 40.9 mmol) in DMF (40 mL) was added 1M potassium tert-butoxide in tert-butanol (40.9 mL, 40.9 mmol). The reaction was stirred for 2 minutes and tert-butyl bromoacetate (6.61 mL, 40.9 mmol) was added. The reaction was stirred for 1 hour and was quenched with 200 mL of water. The product was extracted into EtOAc and the organic solution was washed with water, dried over $MgSO_4$, filtered and concentrated in vacuo. Purification via flash chromatography on silica gel (9:1 hexanes:EtOAc) afforded the title compound as a clear oil (3.53 g). $^1H$ NMR (400 MHz, $CDCl_3$) δ 9.94 (s, 1H), 7.48 (m, 2H), 7.32 (s, 1H), 7.21 (m, 1H), 4.56 (s, 2H), 1.45 (s, 9H).

Step B

[3-(Hydroxyimino-methyl)-phenoxy]-acetic acid tert-butyl ester. To a solution of (3-formyl-phenoxy)-acetic acid tert-butyl ester (2.05 g, 8.68 mmol) in MeOH (30 mL) was added $NH_2OH \cdot HCl$ (0.66 g, 9.54 mmol) and pyridine (3.5 mL, 43.4 mmol) and the reaction was stirred for 2 hours. The MeOH was removed in vacuo and the residue was diluted with EtOAc and 1N HCl. The layers were separated and the aqueous solution was washed with EtOAc. The combined organic layers were dried over $MgSO_4$, filtered and concentrated in vacuo to afford the title compound (1.99 g). $^1H$ NMR (400 MHz, $CDCl_3$) δ 8.07 (s, 1H), 7.23–7.28 (m, 2H), 7.12 (m, 1H), 6.93 (d, 1H), 4.51 (s, 2H), 1.46 (s, 9H).

Step C (3-Aminomethyl-phenoxy)-acetic acid tert-butyl ester. To a solution of [3-(hydroxyimino-methyl)-phenoxy]-acetic acid tert-butyl ester (2.25 g, 5.96 mmol) in EtOH (10 mL) was added Raney Nickel (about 1 g, washed with water followed by EtOH) in 100 mL ethanol. Additional EtOH (90 mL) was required for the transfer. Ammonium hydroxide (10 mL) was added and the mixture was shaken under 45 psi of $H_2$ for 4 hours. The catalyst was removed via filtration through Celite® (diatomaceous earth) and the solution was concentrated to a clear oil. Purification via flash chromatography on silica gel (96.5/3.5/0.1 to 9/1/0.1 $CH_2Cl_2$/MeOH/$NH_4OH$) afforded the title compound as a yellow oil. $^1H$ NMR (400 MHz, $CDCl_3$) δ 7.23 (m, 1H), 6.92 (m, 2H), 6.72 (d, 1H), 4.50 (s, 2H), 3.82 (s, 2H), 1.96 (m, 2H), 1.46 (s, 9H); MS 238 (M+1).

Step D

{3-[(Pyridine-3-sulfonylamino)-methyl]-phenoxy}-acetic acid tert-butyl ester. To a solution of (3-aminomethyl-phenoxy)-acetic acid tert-butyl ester (296 mg, 1.25 mmol) in $CH_2Cl_2$ at 0° C. was added pyridine-3-sulfonyl chloride hydrochloride (279 mg, 1.31 mmol) followed by $Et_3N$ (0.36 mL, 2.6 mmol). The reaction was stirred at room temperature for 24 h and was quenched with a 1:1 solution of water and saturated aqueous $NaHCO_3$. The aqueous solution was washed with $CH_2Cl_2$ (3×). The combined organic solutions were dried ($MgSO_4$), filtered, and concentrated. Medium pressure chromatography (1:1 hexanes:EtOAc) provided the title compound as a white solid (369.5 mg). $^1H$ NMR (400 MHz, $CDCl_3$) δ 9.04 (s, 1H), 8.75 (m, 1H), 8.09 (d, 1H), 7.44 (m, 1H), 7.15 (m, 1H), 6.76 (m, 3H), 5.23 (bs, 1H), 4.44 (s, 2H), 4.16 (d, 2H), 1.47 (s, 9H); MS 379 (M+1).

Preparation 2

2-(4-Bromomethyl-phenyl)-2-methyl-propionic acid ethyl ester

Step A

2-Methyl-2-p-tolyl-propionic acid ethyl ester. NaH (60% by weight in oil, 3.9 g, 98.2 mmol) was washed with DMF and fresh DMF (175 mL) was added. The mixture was cooled to 0° C. and MeI (6.1 mL, 98.2 mmol) followed by a solution of p-tolyl-acetic acid ethyl ester (5.0 g, 28.05 mmol) in DMF (15 mL) were added. The reaction was stirred at room temperature for 48 h. Water was added and the aqueous solution was washed with EtOAc (3×). The combined organic solutions were washed with water (4×) and saturated aqueous $NaHCO_3$ (1×). The organic solution was dried ($MgSO_4$), filtered and concentrated. Medium pressure chromatography (95:5 hexanes:EtOAc) provided 2-methyl-2-p-tolyl-propionic acid ethyl ester (1.2 g). $^1H$ NMR (400 MHz, $CDCl_3$) δ 7.21 (d, 2H), 7.11 (d, 2H), 4.10 (q, 2H), 2.31 (s, 3H), 1.54 (s, 6H), 1.17 (t, 3H).

Step B
2-(4-Bromomethyl-phenyl)-2-methyl-propionic acid ethyl ester. To a solution of 2-methyl-2-p-tolyl-propionic acid ethyl ester (263 mg, 1.27 mmol) and N-bromosuccinimide (272 mg, 1.53 mmol) in $CCl_4$ (15 mL) was added 1,1'-azobis (cyclohexanecarbonitrile) (15.5 mg, 0.06 mmol). The reaction was heated at reflux for 1 h and was diluted with water and $CH_2Cl_2$. The layers were separated and the aqueous layer was washed with $CH_2Cl_2$ (3×). The combined organic solutions were dried ($MgSO_4$), filtered, and concentrated. Medium pressure chromatography (95:5 hexanes:EtOAc) provided 2-(4-bromomethyl-phenyl)-2-methyl-propionic acid ethyl ester (354 mg). $^1$H NMR (400 MHz, $CDCl_3$) δ 7.31 (m, 4H), 4.47 (s, 2H), 4.10 (q, 2H), 1.54 (s, 6H), 1.17 (t, 3H).

Preparation 3
[2-(4-Bromomethyl-phenyl)-2-methyl-propoxy]-tert-butyl-dimethyl-silane
Step A
2-Methyl-2-β-tolyl-propan-1-ol. To a solution of 2-methyl-2-p-tolyl-propionic acid ethyl ester (510 mg, 2.47 mmol) in THF (10 mL) at 0° C. was added lithium aluminum hydride (1M in $Et_2O$, 2.6 mL, 2.6 mmol). The reaction was stirred for 0.5 h and the reaction was quenched by consecutive addition of water (0.1 mL), 15% NaOH (0.1 mL), and water (0.3 mL). The reaction was diluted with EtOAc, dried ($MgSO_4$), filtered and concentrated to yield 2-methyl-2-p-tolyl-propan-1-ol (405 mg). $^1$H NMR (400 MHz, $CDCl_3$) δ 7.27 (d, 2H), 7.15 (d, 2H), 3.58 (s, 2H), 2.32 (s, 3H), 1.31 (s, 6H); MS 165 (M+1).
Step B
tert-Butyl-dimethyl-(2-methyl-2-p-tolyl-propoxy)-silane. To a solution of 2-methyl-2-p-tolyl-propan-1-ol (405 mg, 2.46 mmol) in DMF (5 mL) was added imidazole (335 mg, 4.92 mmol) followed by tert-butyldimethylsilyl chloride (465 mg, 3.08 mmol). The reaction was stirred for 24 h and water was added. The aqueous solution was washed with EtOAc (3×). The combined organic solutions were washed with water (4×). The organic solution was dried ($MgSO_4$), filtered and concentrated. Medium pressure chromatography (hexanes) provided tert-butyl-dimethyl-(2-methyl-2-p-tolyl-propoxy)-silane (619 mg). $^1$H NMR (400 MHz, $CDCl_3$) δ 7.26 (d, 2H), 7.10 (d, 2H), 3.49 (s, 2H), 2.31 (s, 3H), 1.27 (s, 6H), 0.85 (s, 9H), −0.06 (s, 6H).
Step C
[2-(4-Bromomethyl-phenyl)-2-methyl-propoxy]-tert-butyl-dimethyl-silane. The title compound was prepared following the procedure described in Preparation 2, Step B using tert-butyl-dimethyl-(2-methyl-2-p-tolyl-propoxy)-silane (398 mg, 1.42 mmol) as the starting material. The reaction time was 24 h and the compound was purified via medium pressure chromatography using hexanes as the eluant. $^1$H NMR (400 MHz, $CDCl_3$) δ 7.31 (m, 4H), 4.46 (s, 2H), 3.48 (s, 2H), 1.26 (s, 6H), 0.81 (s, 9H), −0.10 (s, 6H).

EXAMPLE 1
2-(4-{[(3–Carboxymethoxy-benzyl)-(pyridine-3-sulfonyl)-amino]-methyl}-phenyl)-2-methyl-propionic acid
Step A
2-(4-{[(3-tert-Butoxycarbonylmethoxy-benzyl)-(pyridine-3-sulfonyl)-amino]-methyl}-phenyl)-2-methyl-propionic acid ethyl ester. NaH (60% by weight in oil, 23 mg, 0.55 mmol) was washed with DMF (5 mL) and fresh DMF (5 mL) was added. The reaction was cooled to 0° C. and a solution of {3-[(pyridine-3-sulfonylamino)-methyl]-phenoxy}-acetic acid tert-butyl ester (184 mg, 0.486 mmol) in DMF (1 mL) was added. The reaction was stirred for 1 h and 2-(4-bromomethyl-phenyl)-2-methyl-propionic acid ethyl ester (145 mg, 0.51 mmol) in DMF (1 mL) was added. The reaction was warmed to room temperature and was heated at 100° C. for 2 h. Water was added and the aqueous solution was washed with EtOAc (3×). The combined organic solutions were washed with water (5×), dried ($MgSO_4$), filtered and concentrated. Flash chromatography (2:1 hexanes:EtOAc) provided 2-(4-{[(3-tert-butoxycarbonylmethoxy-benzyl)-(pyridine-3-sulfonyl)-amino]-methyl}-phenyl)-2-methyl-propionic acid ethyl ester (138 mg). $^1$H NMR (400 MHz, $CDCl_3$) δ 9.01 (s, 1H), 8.76 (m, 1H), 7.97 (m, 1H), 7.40 (m, 1H), 7.19 (d, 2H), 7.13 (m, 1H), 7.02 (d, 2H), 6.76 (m, 1H), 6.67 (m, 2H), 4.41 (s, 2H), 4.33 (s, 4H), 4.10 (q, 2H), 1.52 (s, 6H), 1.49 (s, 9H), 1.17 (t, 3H).
Step B
2-(4-{[(3–Carboxymethoxy-benzyl)-(pyridine-3-sulfonyl)-amino]-methyl}-phenyl)-2-methyl-propionic acid ethyl ester
To a solution of 2-(4-{[(3-tert-butoxycarbonylmethoxy-benzyl)-(pyridine-3-sulfonyl)-amino]-methyl}-phenyl)-2-methyl-propionic acid ethyl ester (138 mg, 0.237 mmol) in MeOH (5 mL) was added aqueous NaOH (2N, 0.36 mL, 0.72 mmol). The reaction was heated at 100° C. for 1 h and was cooled to room temperature. The reaction was concentrated in vacuo and was diluted with water and EtOAc. The pH was adjusted to about 5 with 1N HCl. The aqueous solution was washed with EtOAc (3×). The combined organic solutions were dried ($MgSO_4$), filtered, and concentrated. Sodium chloride was added to the aqueous solution and the solution was washed with EtOAc (3×). The combined organic solutions were dried ($MgSO_4$), filtered, and concentrated. The combined title compound (104 mg) was used in the next step without further purification. MS 527 (M+1).
Step C
2-(4-{[(3–Carboxymethoxy-benzyl)-(pyridine-3-sulfonyl)-amino]-methyl}-phenyl)-2-methyl-propionic acid. To a solution of 2-(4-{[(3-carboxymethoxy-benzyl)-(pyridine-3-sulfonyl)-amino]-methyl}-phenyl)-2-methyl-propionic acid ethyl ester (83 mg, 0.157 mmol) in THF (10 mL) was added water (1 mL) and $LiOH.H_2O$ (66 mg, 1.58 mmol). The reaction was heated at reflux for 24 h. Additional $LiOH.H_2O$ (66 mg, 1.58 mmol) in water (2 mL) was added and the reaction was heated at reflux for 30 h. The mixture was concentrated in vacuo and to the residue was added THF (3 mL) and water (1.5 mL). The reaction was heated at reflux for 24 h and was cooled to room temperature. The solution was diluted with water and the pH was adjusted to about 5 by addition of 1N HCl. Sodium chloride was added and the aqueous solution was washed with EtOAc (3×). The combined organic solutions were dried ($MgSO_4$), filtered, and concentrated to provide the title compound (74 mg). $^1$H NMR (400 MHz, $CDCl_3$) δ 8.94 (s, 1H), 8.73 (s, 1H), 8.13 (d, 1H), 7.55 (m, 1H), 7.23 (d, 2H), 7.11 (m, 3H), 6.78 (d, 1H), 6.73 (d, 1H), 6.68 (s, 1H), 4.90 (s, 2H), 4.39 (s, 2H), 3.30 (s, 2H), 1.50 (s, 6H); MS 497 (M−1).

EXAMPLE 2
(3-{[[4-(2-Hydroxy-1,1-dimethyl-ethyl)-benzyl]-(pyridine-3-sulfonyl)-amino]-methyl}-phenoxy)-acetic acid
Step A
(3-{[{4-[2-(tert-Butyl-dimethyl-silanyloxy)-1,1-dimethyl-ethyl]-benzyl}-(pyridine-3-sulfonyl)-amino]-methyl}-phenoxy)-acetic acid tert-butyl ester. The title compound was prepared by alkylation of {3-[(pyridine-3-sulfonylamino)-methyl]-phenoxy}-acetic acid tert-butyl ester (122 mg, 0.322 mmol) with [2-(4-bromomethyl-phenyl)-2-methyl-propoxy]-tert-butyl-dimethyl-silane (121 mg, 0.339 mmol) following the procedure described for Example 1, Step A. The reaction time was 1 h. The crude product (238 mg) was used in the next step without purification. MS 655 (M+1).

Step B (3-{[[4-(2-Hydroxy-1,1-dimethyl-ethyl)-benzyl]-(pyridine-3-sulfonyl)-amino]-methyl}-phenoxy)-acetic acid tert-butyl ester. To a solution of (3-{[{4-[2-(tert-butyl-dimethyl-silanyloxy)-1,1-dimethyl-ethyl]-benzyl}-(pyridine-3-sulfonyl)-amino]-methyl}-phenoxy)-acetic acid tert-butyl ester (210 mg, 0.321 mmol) in THF (2 mL) was added tetrabutylammonium fluoride (1M in THF, 0.34 mL, 0.34 mmol). The reaction was heated at reflux for 1 h and additional tetrabutylammonium fluoride (1M in THF, 0.34 mL, 0.34 mmol) was added. The reaction was heated at reflux for 24 h and additional tetrabutylammonium fluoride (1M in THF, 0.34 mL, 0.34 mmol) was added. The reaction was heated for 45 minutes and was cooled to room temperature. Water and $CH_2Cl_2$ were added and the layers were separated. The aqueous solution was washed with $CH_2Cl_2$ (3×). The combined organic layers were dried ($MgSO_4$), filtered and concentrated. Medium pressure chromatography (1:1 hexanes:EtOAc to 3:2 EtOAc: hexanes) provided (3-{[[4-(2-hydroxy-1,1-dimethyl-ethyl)-benzyl]-(pyridine-3-sulfonyl)-amino]-methyl}-phenoxy)-acetic acid tert-butyl ester (108 mg). MS 541 (M+1).

Step C (3-{[[4-(2-Hydroxy-1,1-dimethyl-ethyl)-benzyl]-(pyridine-3-sulfonyl)-amino]-methyl}-phenoxy)-acetic acid. A solution of (3-{[[4-(2-hydroxy-1,1-dimethyl-ethyl)-benzyl]-(pyridine-3-sulfonyl)-amino]-methyl}-phenoxy)-acetic acid tert-butyl ester (108 mg, 0.199 mmol) in $CH_2Cl_2$ (2 mL) was cooled to 0° C. and trifluoroacetic acid (1 mL) was added. The reaction was stirred at room temperature for 1 h. The solution was concentrated in vacuo, by azeotroping with $CH_2Cl_2$ (3×). The residue was dissolved in THF and 1N HCl (0.4 mL) was added. The solution was concentrated in vacuo, azeotroping with $CH_2Cl_2$ (3×). Purification by radial chromatography using a solvent gradient ($CH_2Cl_2$ to 20% MeOH in $CH_2Cl_2$) provided the title compound (34 mg). $^1$H NMR (400 MHz, $CDCl_3$) δ 8.79 (s, 1H), 8.69 (s, 1H), 8.11 (d, 1H), 7.52 (m, 1H), 7.21 (d, 2H), 7.09 (m, 1H), 7.02 (d, 2H), 6.76 (d, 1H), 6.70 (m, 2H), 4.86 (s, 2H), 4.32 (m, 4H), 3.48 (s, 2H), 1.22 (s, 6H); MS 485.2 (M+1), 483.4 (M−1).

NMR spectra were recorded on a Varian Unity 400 spectrometer (Varian Co., Palo Alto, Calif.) at about 23° C. at 400 MHz for proton nuclei. Chemical shifts are expressed in parts per million. The peak shapes are denoted as follows: s, singlet; d, doublet; t, triplet; q, quartet; m, multiplet; bs, broad singlet. Atmospheric pressure chemical ionization (APCI) mass spectra were obtained on a Fisons Platform II Spectrometer (Micromass Inc., Beverly, Mass.). Where the intensity of chlorine or bromine-containing ions are described the expected intensity ratio was observed (approximately 3:1 for $^{35}$Cl/$^{37}$Cl-containing ions and 1:1 for $^{79}$Br/$^{81}$Br-containing ions) and the intensity of only the lower mass ion is given.

Medium pressure chromatography was performed using a Biotage purification system (Biotage, Dyax Corporation, Charlottesville, Va.) under nitrogen pressure. Flash chromatography was performed with either Baker Silica Gel (40 μm) (J. T. Baker, Phillipsburg, N.J.) or Silica Gel 60 (EM Sciences, Gibbstown, N.J.) in glass columns under low nitrogen pressure. Radial Chromatography was performed using a Chromatotron (model 7924T, Harrison Research, Palo Alto, Calif.). Dimethylformamide (DMF), tetrahydrofuran (THF), and dichloromethane ($CH_2Cl_2$) used as reaction solvents were the anhydrous grade supplied by Aldrich Chemical Company (Milwaukee, Wis.). The term "concentrated" refers to removal of solvent at water aspirator pressure on a rotary evaporator. The term "EtOAc" means ethyl acetate. The terms "dichloromethane" and "methylene chloride" are synonymous and are used interchangeably throughout this description and in the Examples and Preparations.

Rat $EP_2$ Recptor Binding Assay

Assay for Binding to Prostaglandin $E_2$ Receptors

The full length $EP_2$ receptor is made as disclosed in Nemoto et al., *Prostaglandins and other Lipid Mediators*, 1997, 54, 713–725. This full length receptor is used to prepare 293S cells expressing the $EP_2$ receptor.

293S cells expressing the rat $EP_2$ prostaglandin $E_2$ receptor are generated according to methods known to those skilled in the art. Typically, PCR (polymerase chain reaction) primers corresponding to the 5' and 3' ends of the published full length receptor are made according to the well known methods disclosed above and are used in an RT-PCR reaction using the total RNA from rat kidney as a source. PCR products are cloned by the TA overhang method into pCR2.1 (Invitrogen, Carlsbad, Calif.) and identity of the cloned receptor is confirmed by DNA sequencing. For expression, the confirmed cDNA is subcloned into the mammalian expression vector PURpCI, a vector generated by subcloning the selectable marker for puromycin resistance into the mammalian expression vector pCI (Promega, Madison, Wis.)

293S cells are transfected with the cloned receptor in PURpCi by lipid mediated transfection. Stable cell lines expressing the receptor are established following selection of transfected cells with puromycin.

Clonal cell lines expressing the maximal number of receptors are chosen following a whole cell $^3$H-$PGE_2$ binding assay using unlabeled $PGE_2$ as a competitor.

Membrane Preparation: All operations are performed at 4° C. Transfected cells expressing prostaglandin $E_2$ type 2 ($EP_2$) receptors are harvested and suspended to 2 million cells per ml in Buffer A [50 mM Tris-HCl (pH 7.4), 10 mM $MgCl_2$, 1 mM EDTA, 1 mM Pefabloc peptide, (Boehringer Mannheim Corp., Indianapolis, Ind.), 10 uM Phosporamidon peptide, (Sigma, St. Louis, Mo.), 1 uM pepstatin A peptide, (Sigma, St. Louis, Mo.), 10 uM elastatinal peptide, (Sigma, St. Louis, Mo.), 100 uM antipain peptide, (Sigma, St. Louis, Mo.)]. The cells are lysed by sonification with a Branson Sonifier (Branson Ultrasonics Corporation, Danbury, Conn.) in 2 fifteen second bursts. Unlysed cells and debris are removed by centrifugation at 100×g for 10 min. Membranes are then harvested by centrifugation at 45,000×g for 30 minutes. Pelleted membranes are resuspended to 3–10 mg protein per ml, protein concentration being determined of the method of Bradford [Bradford, M., Anal. Biochem., 72, 248 (1976)]. Resuspended membranes are then stored frozen at −80° C. until use.

Binding Assay: Frozen membranes prepared as above are thawed and diluted to 1 mg protein per ml in Buffer A above. One volume of membrane preparation is combined with 0.05 volume test compound or buffer and one volume of 3 nM $^3$H-prostaglandin $E_2$ (Amersham, Arlington Heights, Ill.) in Buffer A. The mixture (205 μL total volume) is incubated for 1 hour at 25° C. The membranes are then recovered by filtration through type GF/C glass fiber filters (Wallac, Gaithersburg, Md.) using a Tomtec harvester (Tomtec, Orange, Conn.). The membranes with bound $^3$H-prostaglandin $E_2$ are trapped by the filter, while the buffer and unbound $^3$H-prostaglandin $E_2$ pass through the filter into waste. Each sample is then washed 3 times with 3 ml of [50 mM Tris-HCl (pH 7.4), 10 mM $MgCl_2$, 1 mM EDTA]. The filters are then dried by heating in a microwave oven. To determine the amount of $^3H$-prostaglandin bound to the membranes, the dried filters are placed into plastic bags with scintillation fluid and counted in a LKB 1205 Betaplate reader (Wallac, Gaithersburg, Md.). $IC_{50}$ s are determined from the concentration of test compound required to displace 50% of the specifically bound $^3H$-prostaglandin $E_2$.

Example 1 rat $EP_2$ binding $IC_{50}$=750 nM
Example 2 rat $EP_2$ binding $IC_{50}$=170 nM The following abbreviations are used herein:

| | |
|---|---|
| I.V. | Intravenous |
| HPLC | High Pressure Liquid Chromatography |
| CPM | Counts Per Minute |
| min | Minute |
| MS | Mass Spectrometry |
| CID | Collision Induced Dissociation |
| AMU | Atomic Mass Unit |
| FBS | Fetal Bovine Serum |
| LC | Liquid Chromatography |
| DMF | Dimethylformamide |
| EtOAc | Ethyl Acetate |
| MeOH | Methanol |
| NMR | Nuclear Magnetic Resonance |
| $Et_3N$ | Triethylamine |
| THF | Tetrahydrofuran |
| H | Hours |

What is claimed is:

1. The compound 2-(4-{[(3-carboxymethoxy-benzyl)-(pyridine-3-sulfonyl)-amino]-methyl}-phenyl)-2-methyl-propionic acid, or a pharmaceutically acceptable salt thereof.

2. The compound (3-{[[4-(2-hydroxy-1,1-dimethyl-ethyl)-benzyl]-(pyridine-3-sulfonyl)-amino]-methyl}-phenoxy)-acetic acid, or a pharmaceutically acceptable salt thereof.

3. The compound (3-{[(4-tert-butyl-benzyl)-(pyridine-N-oxide-3-sulfonyl)-amino]-methyl}-phenoxy)-acetic acid, or a pharmaceutically acceptable salt thereof.

4. The compound (5-{[(4-tert-butyl-benzyl)-(pyridine-3-sulfonyl)-amino]-methyl}-hydroxy-phenoxy)-acetic acid, or a pharmaceutically acceptable salt thereof.

5. The compound:
2-{4-[pyridine-N-oxide-3-sulfonylamino)-methyl]-phenyl}-2-methyl-propionic acid;
(3-{[[4-(2-hydroxy-1,1-dimethyl-ethyl)-benzyl]-(pyridine-3-sulfonyl)-amino]-methyl}-phenoxy)-acetic acid glucuronide;
the sulfate conjugate of pyridine-N-oxide-3-sulfonic acid 4-(2-hydroxy-1,1-dimethyl-ethyl)-benzylamide;
the sulfate conjugate of (3-{[[4-(2-hydroxy-1,1-dimethyl-ethyl)-benzyl]-(pyridine-3-sulfonyl)-amino]-methyl}-phenoxy)-acetic acid;
the sulfate conjugate of pyridine-3-sulfonic acid 4-(2-hydroxy-1,1-dimethyl-ethyl)-benzylamide;
2-methyl-2-{4-[(pyridine-3-sulfonylamino)-methyl]-phenyl}-propionic acid;
(3-{[[4-(1,2-dihydroxy-1-methyl-ethyl)-benzyl]-(pyridine-3-sulfonyl)-amino]-methyl}-phenoxy)-acetic acid;
(3-{[[4-(1-hydroxy-1-methyl-ethyl)-benzyl]-(pyridine-3-sulfonyl)-amino]-methyl}-phenoxy)-acetic acid;
(3-{[[4-(1,1-dimethyl-2-oxo-ethyl)-benzyl]-(pyridine-3-sulfonyl)-amino]-methyl}-phenoxy)-acetic acid; or
(3-{[(4-isopropenyl-benzyl)-(pyridine-3-sulfonyl)-amino]-methyl}-phenoxy)-acetic acid;
or a pharmaceutically acceptable salt thereof.

6. A method of using a compound for determining if a patient has been administered (3-{[4-tert-butyl-benzyl)-(pyridine-3-sulfonyl)-amino]-methyl}-phenoxy)-acetic acid, the method comprising:
obtaining a plasma, urine, bile or fecal sample from the patient; and
determining the presence of one or more of said compound in said plasma, urine, bile or fecal sample;
wherein said compound is selected from the group consisting of
2-(4-{[(3-carboxymethoxy-benzyl)-(pyridine-3-sulfonyl)-amino]-methyl}-phenyl)-2-methyl-propionic acid;
(3-{[[4-(2-hydroxy-1,1-dimethyl-ethyl)-benzyl]-(pyridine-3-sulfonyl)-amino]-methyl}-phenoxy)-acetic acid;
2-{4-[pyridine-N-oxide-3-sulfonylamino)-methyl]-phenyl}-2-methyl-propionic acid;
(3-{[[4-(2-hydroxy-1,1-dimethyl-ethyl)-benzyl]-(pyridine-3-sulfonyl)-amino]-methyl}-phenoxy)-acetic acid glucuronide;
the sulfate conjugate of pyridine-N-oxide-3-sulfonic acid 4-(2-hydroxy-1,1-dimethyl-ethyl)-benzylamide;
the sulfate conjugate of (3-{[[4-(2-hydroxy-1,1-dimethyl-ethyl)-benzyl]-(pyridine-3-sulfonyl)-amino]-methyl}-phenoxy)-acetic acid;
the sulfate conjugate of pyridine-3-sulfonic acid 4-(2-hydroxy-1,1-dimethyl-ethyl)-benzylamide;
2-methyl-2-{4-[(pyridine-3-sulfonylamino)-methyl]-phenyl}-propionic acid;
(3-{[(4-tert-butyl-benzyl)-(pyridine-N-oxide-3-sulfonyl)-amino]-methyl}-phenoxy)-acetic acid;
(5-{[(4-tert-butyl-benzyl)-(pyridine-3-sulfonyl)-amino]-methyl}-hydroxy-phenoxy)-acetic acid;
(3-{[[4-(1,2-dihydroxy-1-methyl-ethyl)-benzyl]-(pyridine-3-sulfonyl)-amino]-methyl}-phenoxy)-acetic acid;
(3-{([[4-(1-hydroxy-1-methyl-ethyl)-benzyl]-(pyridine-3-sulfonyl)-amino]-methyl}-phenoxy)-acetic acid;
(3-{[[4-(1,1-dimethyl-2-oxo-ethyl)-benzyl]-(pyridine-3-sulfonyl)-amino]-methyl}-phenoxy)-acetic acid; and
(3-{[(4-isopropenyl-benzyl)-(pyridine-3-sulfonyl)-amino]-methyl}-phenoxy)-acetic acid.

7. A method of treating osteoporosis or aiding in healing a bone fracture, the method comprising administering to a patient in need thereof a therapeutically effective amount of a compound selected from:
2-(4-{[(3-carboxymethoxy-benzyl)-(pyridine-3-sulfonyl)-amino]-methyl}-phenyl)-2-methyl-propionic acid;
(3-{[[4-(2-hydroxy-1,1-dimethyl-ethyl)-benzyl]-(pyridine-3-sulfonyl)-amino]-methyl}-phenoxy)-acetic acid;
(3-{[(4-tert-butyl-benzyl)-(pyridine-N-oxide-3-sulfonyl)-amino]-methyl}-phenoxy)-acetic acid;
(5-{[(4-tert-butyl-benzyl)-(pyridine-3-sulfonyl)-amino]-methyl}-hydroxy-phenoxy)-acetic acid;
(3-{[[4-(1,2-dihydroxy-1-methyl-ethyl)-benzyl]-(pyridine-3-sulfonyl)-amino]-methyl}-phenoxy)-acetic acid;
(3-{[[4-(1-hydroxy-1-methyl-ethyl)-benzyl]-(pyridine-3-sulfonyl)-amino]-methyl}-phenoxy)-acetic acid;
(3-{[[4-(1,1-dimethyl-2-oxo-ethyl)-benzyl]-(pyridine-3-sulfonyl)-amino]-methyl}-phenoxy)-acetic acid; or
(3-{[(4-isopropenyl-benzyl)-(pyridine-3-sulfonyl)-amino]-methyl}-phenoxy)-acetic acid;
or a pharmaceutically acceptable salt thereof.

8. A pharmaceutical composition comprising one or more compound selected from
2-(4-{[(3-carboxymethoxy-benzyl)-(pyridine-3-sulfonyl)-amino]-methyl}-phenyl)-2-methyl-propionic acid;
(3-{[[4-(2-hydroxy-1,1-dimethyl-ethyl)-benzyl]-(pyridine-3-sulfonyl)-amino]-methyl}-phenoxy)-acetic acid;

2-{4-[pyridine-N-oxide-3-sulfonylamino)-methyl]-phenyl}-2-methyl-propionic acid;
(3-{[[4-(2-hydroxy-1,1-dimethyl-ethyl)-benzyl]-(pyridine-3-sulfonyl)-amino]-methyl}-phenoxy)-acetic acid glucuronide;
the sulfate conjugate of pyridine-N-oxide-3-sulfonic acid 4-(2-hydroxy-1,1-dimethyl-ethyl)-benzylamide;
the sulfate conjugate of (3-{[[4-(2-hydroxy-1,1-dimethyl-ethyl)-benzyl]-(pyridine-3-sulfonyl)-amino]-methyl}-phenoxy)-acetic acid;
the sulfate conjugate of pyridine-3-sulfonic acid 4-(2-hydroxy-1,1-dimethyl-ethyl)-benzylamide;
2-methyl-2-{4-[(pyridine-3-sulfonylamino)-methyl]-phenyl}-propionic acid;
(3-{[(4-tert-butyl-benzyl)-(pyridine-N-oxide-3-sulfonyl)-amino]-methyl}-phenoxy)-acetic acid;
(5-{[(4-tert-butyl-benzyl)-(pyridine-3-sulfonyl)-amino]-methyl}-hydroxy-phenoxy)-acetic acid;
(3-{[[4-(1,2-dihydroxy-1-methyl-ethyl)-benzyl]-(pyridine-3-sulfonyl)-amino]-methyl}-phenoxy)-acetic acid;
(3-{[[4-(1-hydroxy-1-methyl-ethyl)-benzyl]-(pyridine-3-sulfonyl)-amino]-methyl}-phenoxy)-acetic acid;
(3-{[[4-(1,1-dimethyl-2-oxo-ethyl)-benzyl]-(pyridine-3-sulfonyl)-amino]-methyl}-phenoxy)-acetic acid; or
(3-{[(4-isopropenyl-benzyl)-(pyridine-3-sulfonyl)-amino]-methyl}-phenoxy)-acetic acid;
or a pharmaceutically acceptable salt thereof.

* * * * *